(12) United States Patent
Friedman

(10) Patent No.: US 12,151,019 B2
(45) Date of Patent: Nov. 26, 2024

(54) COMPOSITIONS FOR BLOOD STORAGE AND TRANSFUSIONS

(71) Applicant: Albert Einstein College of Medicine, Bronx, NY (US)

(72) Inventor: Joel M. Friedman, West Orange, NJ (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 18/419,852

(22) Filed: Jan. 23, 2024

(65) Prior Publication Data

US 2024/0156720 A1     May 16, 2024

Related U.S. Application Data

(60) Continuation-in-part of application No. 18/051,266, filed on Oct. 31, 2022, which is a division of application No. 17/565,556, filed on Dec. 30, 2021, now Pat. No. 11,484,493, which is a continuation of application No. PCT/US2021/058611, filed on Nov. 9, 2021.

(60) Provisional application No. 63/235,880, filed on Aug. 23, 2021, provisional application No. 63/161,696, filed on Mar. 16, 2021, provisional application No. 63/111,160, filed on Nov. 9, 2020.

(51) Int. Cl.
| | | |
|---|---|---|
| *A61K 35/14* | (2015.01) | |
| *A61K 9/00* | (2006.01) | |
| *A61K 9/06* | (2006.01) | |
| *A61K 31/05* | (2006.01) | |
| *A61K 31/12* | (2006.01) | |
| *A61K 31/121* | (2006.01) | |
| *A61K 31/352* | (2006.01) | |
| *A61K 31/366* | (2006.01) | |
| *A61K 31/4375* | (2006.01) | |
| *A61K 31/593* | (2006.01) | |
| *A61K 47/10* | (2017.01) | |
| *A61K 47/12* | (2006.01) | |
| *A61P 7/00* | (2006.01) | |
| *A61P 37/06* | (2006.01) | |

(52) U.S. Cl.
CPC ............ *A61K 9/0014* (2013.01); *A61K 9/06* (2013.01); *A61K 31/05* (2013.01); *A61K 31/12* (2013.01); *A61K 31/121* (2013.01); *A61K 31/352* (2013.01); *A61K 31/366* (2013.01); *A61K 31/4375* (2013.01); *A61K 31/593* (2013.01); *A61K 47/10* (2013.01); *A61K 47/12* (2013.01); *A61P 7/00* (2018.01); *A61P 37/06* (2018.01)

(58) Field of Classification Search
CPC .................................. A61K 31/12; A61K 35/14
USPC .............................................. 424/579; 514/679
See application file for complete search history.

(56) References Cited

U.S. PATENT DOCUMENTS

| | | |
|---|---|---|
| 11,484,493 B2 | 11/2022 | Friedman |
| 2004/0054313 A1 | 3/2004 | Molan |
| 2008/0057088 A1 | 3/2008 | Blass et al. |
| 2009/0297634 A1 | 12/2009 | Friedman et al. |
| 2012/0052095 A1 | 3/2012 | Chaniyilparampu et al. |
| 2014/0017121 A1 | 1/2014 | Schoenfisch et al. |
| 2014/0105986 A1 | 4/2014 | Doxey et al. |
| 2014/0199391 A1 | 7/2014 | Birbara |
| 2015/0147396 A1 | 5/2015 | Nacharaju et al. |
| 2016/0374960 A1 | 12/2016 | DiMauro |
| 2017/0119814 A1 | 5/2017 | Friedman et al. |
| 2018/0256509 A1 | 9/2018 | Friedman et al. |
| 2019/0201478 A1 | 7/2019 | Benita et al. |
| 2022/0257642 A1 | 8/2022 | Munro et al. |
| 2023/0064665 A1 | 3/2023 | Friedman |
| 2023/0069711 A1 | 3/2023 | Friedman |
| 2023/0121214 A1 | 4/2023 | Friedman |

FOREIGN PATENT DOCUMENTS

| | | |
|---|---|---|
| JP | 2008520694 A | 6/2008 |
| JP | 2014504592 A | 2/2014 |
| WO | 2005/105059 A1 | 11/2005 |
| WO | 2009/131931 A1 | 10/2009 |
| WO | 2010/048724 A1 | 5/2010 |
| WO | 2010123547 A1 | 10/2010 |
| WO | 2013/169538 A1 | 11/2013 |
| WO | 2018/039752 A1 | 3/2018 |
| WO | 2020/245574 A1 | 12/2020 |
| WO | 2022099193 A1 | 5/2022 |

OTHER PUBLICATIONS

Soumya et al. "CUPRAC-BCS and antioxidant activity assays as reliable markers of antioxidant capacity in erythrocytes," Hematology, vol. 20(3), pp. 165-174 (2015) (Year: 2015).*
Tanner & Marks Skin Research and Technology 2008, 14: 249-260.
Australian Examination Report for Australian Patent Application No. 2021373079 dated Jun. 29, 2023, 3 pages.
Principles of Skin Therapy, Common types of topical formulations, www.dermweb.com/therapy/common.htm, downloaded Aug. 23, 2023.
Boscariol et al., Transdermal permeation of curcumin promoted by choline geranate ionic liquid: Potential for the treatment of skin diseases, Saudi Pharmaceutical Journal 30 (2022) 382-397.
'Viscosity Tables', V&P Scientific, Jan. 13, 2008 (Jan. 13, 2008), 3 pages.
Amalraj, A. et al. "A Novel Highly Bioavailable Curcumin Formulation Improves Symptoms and Diagnostic Indicators in Rheumatoid Arthritis Patients: A Randomized, Double-Blind, Placebo-Controlled, Two-Dose, Three-Arm, and Parallel-Group Study", J Med Food. Oct. 2017;20(10):1022-1030.

(Continued)

*Primary Examiner* — Raymond J Henley, III

(74) *Attorney, Agent, or Firm* — Fox Rothschild LLP

(57) ABSTRACT

Formulations comprising one or more active agents for blood storage and transfusions are provided. Also provided methods for prolonging viability of blood and enhancing efficacy of blood transfusion.

20 Claims, No Drawings

(56) References Cited

OTHER PUBLICATIONS

Anand, P. et al. "Curcumin and cancer: an "old-age" disease with an "age-old" solution", Cancer Lett. Aug. 18, 2008;267(1):133-164.
Babaei, F. et al. "Curcumin (a constituent of turmeric): New treatment option against COVID-19", Food Sci Nutr. Sep. 6, 2020;8(10):5215-5227.
Banez, M. J. et al. "A systemic review on the antioxidant and anti-inflammatory effects of resveratrol, curcumin, and dietary nitric oxide supplementation on human cardiovascular health", Nutr Res. Jun. 2020;78:11-26.
Belcaro, G. et al. A controlled study of a lecithinized delivery system of curcumin (Meriva®) to alleviate the adverse effects of cancer treatment. Phytother Res. Mar. 2014;28(3):444-450.
Boonla, O. et al. "Curcumin improves endothelial dysfunction and vascular remodeling in 2K—1C hypertensive rats by raising nitric oxide availability and reducing oxidative stress", Nitric Oxide. Nov. 15, 2014;42:44-53.
Carter, A. "Curry compound fights cancer in the clinic", J Natl Cancer Inst. May 7, 2008;100(9):616-617.
Chen, R. et al. "Curcumin attenuates cardiomyocyte hypertrophy induced by high glucose and insulin via the PPAR?/Akt/NO signaling pathway", Diabetes Res Clin Pract. May 2015;108(2):235-242.
Choudhuri, T. et al. "Curcumin induces apoptosis in human breast cancer cells through p53-dependent Bax induction", FEBS Lett. Feb. 13, 2002;512(1-3):334-340.
Debata, P.R. et al. "A novel curcumin-based vaginal cream Vacurin selectively eliminates apposed human cervical cancer cells", Gynecol Oncol. Apr. 2013;129(1):145-153.
Dhandapani, K.M. et al. "Curcumin suppresses growth and chemoresistance of human glioblastoma cells via AP-1 and NFkappaB transcription factors", J Neurochem. Jul. 2007;102(2):522-538.
Dhar, S. et al. "Promising role of curcumin against viral diseases emphasizing COVID-19 management: A review on the mechanistic insights with reference to host-pathogen interaction and immunomodulation", J Funct Foods. Jul. 2021;82:104503, 12 pages.
Fang, W. et al., "The role of NO in COVID-19 and potential therapeutic strategies". Free Radic Biol Med. Feb. 1, 2021;163:153-162.
Farhangkhoee, H. et al. "Differential effects of curcumin on vasoactive factors in the diabetic rat heart", Nutr Metab (Lond). Jul. 18, 2006;3:27, 8 pages.
Forte, M. et al. "Targeting Nitric Oxide with Natural Derived Compounds as a Therapeutic Strategy in Vascular Diseases", Oxid Med Cell Longev. 2016;Article ID:7364138, 20 pages.
Hajavi, J. et al. "Curcumin: A Naturally Occurring Modulator of Adipokines in Diabetes", J Cell Biochem. Dec. 2017;118(12):4170-4182.
Hedayati-Moghadam, M. et al. "The Role of Chemokines in Cardiovascular Diseases and the Therapeutic Effect of Curcumin on CXCL8 and CCL2 as Pathological Chemokines in Atherosclerosis", Adv Exp Med Biol. 2021;1328:155-170.
Hickey, M.A. et al. "Improvement of neuropathology and transcriptional deficits in CAG 140 knock-in mice supports a beneficial effect of dietary curcumin in Huntington's disease", Mol Neurodegener. Apr. 4, 2012;7:12, 16 pages.
Holte, P. ten, et al. "HDAC inhibition in cancer therapy: an increasingly intriguing tale of chemistry, biology and clinical benefit," Cancer. Springer, Berlin, Heidelberg, 2007. 293-331.
International Search Report and Written Opinion mailed Dec. 12, 2022, in International Application No. PCT/US2022/075651, 16 pages.
Jeengar, M.K. et al. "Emu oil based nano-emulgel for topical delivery of curcumin", Int J Pharm. Jun. 15, 2016;506(1-2):222-236.
Kahkhaie, K.R. et al. "Curcumin: a modulator of inflammatory signaling pathways in the immune system", Inflammopharmacology. Oct. 2019;27(5):885-900.
Kanai, M. "Therapeutic applications of curcumin for patients with pancreatic cancer", World J Gastroenterol. Jul. 28, 2014;20(28):9384-9391.
Kanai, M. et al. "A phase I/II study of gemcitabine-based chemotherapy plus curcumin for patients with gemcitabine-resistant pancreatic cancer", Cancer Chemother Pharmacol. Jul. 2011;68(1):157-164.
Karakas et al. "NO-Releasing Nanoparticles Decrease Detrusor Overactivity in DNOS-/-Knockout and Transgenic Sickle Cell Mice", PD19-06, The Journal of Urology, vol. 199, No. 4S, Supplement, May 19, 2018, e397, 1 page.
Karakus et al. "NO-Releasing Nanoparticles Ameliorate Detrusor Overactivity in Transgenic Sickle Cell Mice via Restored NO/ROCK Signaling", J Pharmacol Exp Ther. May 2020;373(2):214-219. doi: 10.1124/jpet.119.264697. Epub Mar. 6, 2020., 6 pages.
Kim, T. et al. "Curcumin activates AMPK and suppresses gluconeogenic gene expression in hepatoma cells", Biochem Biophys Res Commun. Oct. 16, 2009;388(2):377-382.
Lawrence, G.D. "Dietary fats and health: dietary recommendations in the context of scientific evidence", Adv Nutr. May 1, 2013;4(3):294-302.
Lim, G.P. et al. "The curry spice curcumin reduces oxidative damage and amyloid pathology in an Alzheimer transgenic mouse", J Neurosci. Nov. 1, 2001;21(21):8370-8377.
Lin, L. et al. "Targeting colon cancer stem cells using a new curcumin analogue, GO-Y030", Br J Cancer. Jul. 12, 2011;105(2):212-220.
Liu, Z. et al. "The Inhibitory Effect of Curcumin on Virus-Induced Cytokine Storm and Its Potential Use in the Associated Severe Pneumonia", Front Cell Dev Biol. Jun. 12, 2020;8:479, 10 pages.
Margel et al. "Nitric oxide charged catheters as a potential strategy for prevention of hospital acquired infections", PLoS One. Apr. 14, 2017;12(4):e0174443. doi: 10.1371/journal.pone.0174443. PMID: 28410367; PMCID: PMC5391919, 17 pages.
Miao, Y. et al. "Curcumin pretreatment attenuates inflammation and mitochondrial dysfunction in experimental stroke: The possible role of Sirt1 signaling", Brain Res Bull. Mar. 2016;121:9-15.
Mukherjee, S. et al. "Liposomal TriCurin, A Synergistic Combination of Curcumin, Epicatechin Gallate and Resveratrol, Repolarizes Tumor-Associated Microglia/Macrophages, and Eliminates Glioblastoma (GBM) and GBM Stem Cells", Molecules. Jan. 18, 2018;23(1):201, 21 pages.
Mukherjee, S. et al. "Unique synergistic formulation of curcumin, epicatechin gallate and resveratrol, tricurin, suppresses HPV E6, eliminates HPV+ cancer cells, and inhibits tumor progression", Oncotarget. Mar. 29, 2017;8(37):60904-60916.
Nakmareong, S. et al. "Antioxidant and vascular protective effects of curcumin and tetrahydrocurcumin in rats with L-NAME-induced hypertension", Naunyn Schmiedebergs Arch Pharmacol. May 2011;383(5):519-529.
Nakmareong, S. et al. "Tetrahydrocurcumin alleviates hypertension, aortic stiffening and oxidative stress in rats with nitric oxide deficiency", Hypertens Res. Apr. 2012;35(4):418-425.
Oliviero, F. et al. "Anti-inflammatory effects of polyphenols in arthritis",. J Sci Food Agric. Mar. 2018;98(5):1653-1659.
Purkayastha, S. et al. "Curcumin blocks brain tumor formation", Brain Res. Apr. 17, 2009;1266:130-138.
Rattis, B.A.C et al. "Curcumin as a Potential Treatment for COVID-19", Front Pharmacol. May 7, 2021;12:675287, 14 pages.
Rungseesantivanon et al. "Curcumin supplementation could improve diabetes-induced endothelial dysfunction associated with decreased vascular superoxide production and PKC inhibition", BMC Complementary and Alternative Medicine 2010, 10:57; 9 pages.
Satheesh A. et al., "Penetration enhancer accelerated solubilization of curcumin by poly(vinylpyrrolidone)", J. Indian Chem. Soc., vol. 96, Jan. 2019, pp. 14-18.
Sui, Z. et al. "Inhibition of the HIV-1 and HIV-2 proteases by curcumin and curcumin boron complexes", Bioorg Med Chem. Dec. 1993;1(6):415-422.
Turmeric Curcumin Topical Patches—30 Days Supply—USA Made by Live To Shine, —Amazon.com: Turmeric Curcumin Topical Patches—30 Days Supply USA Made by Live To Shine : Health & Household <https://www.amazon.com/Turmeric-Curcumin-Topical-

(56) References Cited

OTHER PUBLICATIONS

Patches-Supply/dp/B07G94GHNV/ref=sr_1_5?crid=AICY5YTKFKLJ&keywords=curcumin+patch&qid=1647009345&sprefix=curcumin+patch%2Caps%2C69&sr=8-5>, 1 page.

Turmeric Max Patch—30 Patches—Omni Global Labs, Amazon.com: Turmeric Max Patch—30 Patches : Health & Household <https://www.amazon.com/Turmeric-Max-Topical-Patch-Patches/dp/B07K4W17NC/ref=sr_1_6?crid=AICY5YTKFKLJ&keywords=curcumin+patch&qid=1647009345&sprefix=curcumin+patch%2Caps%2C69&sr=8-6>, 3 pages.

Xu, PH. et al. "The relaxant effect of curcumin on porcine coronary arterial ring segments", Vascul Pharmacol. Jul. 2007;47(1):25-30.

Yang et al., 'Novel nitric oxide-generating platform using manuka honey as an anti-biofilm strategy in chronic rhinosinusitis', International Forum of Allergy & Rhinology, vol. 10, issue 2, Dec. 13, 2019 (13.21.2019), p. 223-232.

Yang, F. et al. "Curcumin inhibits formation of amyloid beta oligomers and fibrils, binds plaques, and reduces amyloid in vivo", J Biol Chem. Feb. 18, 2005;280(7):5892-5901.

Zendedel, E. et al. "Impact of curcumin on sirtuins: A review", J Cell Biochem. Dec. 2018;119(12):10291-10300.

\* cited by examiner

COMPOSITIONS FOR BLOOD STORAGE AND TRANSFUSIONS

CROSS-REFERENCE TO RELATED APPLICATIONS

This application is a continuation-in-part application of U.S. application Ser. No. 18/051,266, filed on Oct. 31, 2022, which is a divisional application of U.S. Pat. No. 11,484, 493, which is a Continuation of International Application No. PCT/US2021/058611 filed on Nov. 9, 2021, which claims the benefit priority to Provisional Application Nos. 63/111,160, filed Nov. 9, 2020; 63/161,696 filed Mar. 16, 2021; and 63/235,880 filed Aug. 23, 2021, the disclosures of all of which are hereby incorporated by reference in their entireties.

TECHNICAL FIELD

Disclosed herein are formulations comprising curcuminoids for blood storage and transfusions. Also provided methods for prolonging viability of blood and enhancing efficacy of blood transfusion.

BACKGROUND

Delivery of many therapeutic agents remains a challenge due to bioavailability issues that preclude achieving therapeutic levels either systemically or locally at a targeted site. Poor bioavailability arises from various factors including low solubility, low uptake from the gut, and rapid elimination from the circulation due to rapid breakdown by the liver (first pass limitations). As a result, many promising therapeutics with the appropriate activity cannot be directly delivered in an effective manner to afflicted sites such as the lungs, arthritic joints, inner ear, sinuses etc. Meanwhile, oral or IV routes of administration often do not provide adequate therapeutic levels at the targeted local site.

Nitric oxide (NO) has known systemic benefits including the capability of reversing inflammation, preventing and reversing endothelial dysfunction, repolarizing activated macrophages, deactivating activated platelets, protecting/restoring the endothelial lining of blood vessels (glycocalyx) and antimicrobial/antiviral activity. Proinflammatory insults result in enhanced production of reactive oxygen species (ROS) which drives the development and continuation of endothelial dysfunction. The enhanced levels of ROS set in motion multiple events that cause dysregulation of the vasculature. The ROS degrades the glycocalyx which results in loss of vascular integrity, enhanced access of circulating cells (monocytes, red blood cells, neutrophils and platelets) to and adhesion to the endothelial surface, loss of sheer stress mediated NO production and loss of superoxide dismutase which limits ROS. Enhanced ROS causes endothelial nitric oxide synthase (eNOS) to stop production of NO in endothelium and actually start generating more ROS. Enhancing NO levels either with direct supplementation or enhanced production can dramatically reverse this cycle and restore vascular homeostasis. However, systemic delivery of NO is a challenge due to the short lifetime of the NO molecule and limited access to the circulation.

CD38 plays a pivotal role in multiple organ systems and tissues. CD38 is the main enzyme for nicotinamide adenine dinucleotide (NAD) degradation in mammalian cells. Decreased NAD levels are closely related to metabolic syndromes and aging-related diseases. In the vasculature and apropos of treating endothelial dysfunction, lowering CD38 levels significantly alleviated angiotensin II (Ang II)-induced vascular remodeling in mice, as shown by decreased blood pressures; reduced vascular media thickness, media-to-lumen ratio, and collagen deposition; and restored elastin expression. Lowering CD38 levels remarkably mitigated Ang II-induced vascular senescence by suppressing the biogenesis, secretion, and internalization of senescence-associated small extracellular vesicles (SA-sEVs), which facilitated the senescence of neighboring non-damaged VSMCs. Furthermore, the protective effects of CD38 deficiency on VSMC senescence were related to restoration of lysosome dysfunction, particularly with respect to the maintenance of sirtuin-mediated mitochondrial homeostasis and activation of the mitochondria-lysosomal axis in VSMCs. Therefore, CD38 activity and the resulting associated intracellular NAD decline are critical for Ang II-induced VSMC (vascular smooth muscle cell) senescence and vascular remodeling thus CD38 and its associated intracellular NAD decline are critical for Ang II-induced VSMC senescence and vascular remodeling which can result in cardiovascular disease and renal failure. Similar results are reported for the centrality of CD38/NAD+ activity in other disease states including osteoarthritic, lupus, neuropathies and age related decline in physical and cognitive function. The central role of CD38 arises in part due to any of multiple pro-inflammatory triggers including a build up of senescent cells resulting in its overexpression in the activated immune cells such as macrophages and microglial cells as well as on the activated endothelial lining of all blood vessels.

SUMMARY

This patent document provides a transdermal formulation for the delivery of one or more active agents to a subject in the treatment of diseases or conditions associated with elevated CD38 levels that in turn causes a drop in NAD+ levels. Low NAD+ promotes mitochondrial dysfunction and limits activity of the SIRTUINs. Sirtuin activity is needed to maintain NO production in the endothelium and shut down oxidative and nitrosative stress generated by activate immune cells such as the M1 populations of macrophages and microglial cells. CD38 is expressed on the surface of macrophages, microglial cells and other immunoactive leucocytes as well as on the endothelial lining of blood vessels. Increased levels of CD38 is triggered by diseases or conditions such as trauma, inflammation, infection, radiation, chemotherapy and excess amounts of senescent cells. The enhanced levels on CD38 in turn promotes further cell senescence, inflammation and oxidative stress which further stimulated more CD38 production creating a cycle of ongoing inflammation that is hard to break.

The transdermal formulations disclosed herein lead to reduction of CD38 ectoenzyme activities such as NADase activity; thereby enhancing NAD+ levels and promoting the activity of the NAD+ dependent sirtuins. In so doing this approach provides new methods of both preventing and treating various diseases including those stemming from endothelial dysfunction following either an acute or chronic pro-inflammatory insult, age related decline in physical and cognitive skills, age associated changes in cardiac tissues, vascular hypertrophy, osteoarthritis, peripheral neuropathy and long COVID. Additionally this approach overcomes negative consequences of CD38 overproduction with respect to the ability of stem cells to differentiate into mature cells, which is at least in part responsible for the anemia of chronic inflammation and the lack of efficacy of intrinsic stem cells and stem cell therapy to repair damaged tissues.

The formulations disclosed herein for topical delivery results in direct delivery into both the plasma and blood cells thus bypassing the gut and first pass elimination by the liver. Furthermore, red blood cells loaded with the active agent can act as stealth delivery vehicles that are invisible to the immune system and the liver. Additionally, uptake of deliverables into activated CD38 loaded (M1 population) circulating macrophages and other immunoactive leucocytes can result in rapid repolarization (back to M2 population) which rapidly decreases the levels of CD38 and the production of pro-inflammatory cytokines. This strategy should also decrease the senescent cell burden. By combining potent anti-inflammatory agents (curcuminoids) that both repolarize M1 macrophages (thus lowering CD38 levels) and promote sirtuin activity, with senolytic agents (e.g. quercetin, apigenin, fisetin, luteolin), the prospects for both breaking the inflammatory cycle in chronic diseases and promoting tissue repair by allowing for stem cell differentiation and proliferation are significantly maximized.

An aspect of the patent document discloses a transdermal formulation for enhancing systemic nitric oxide (NO) through the CD38/NAD+ pathway, comprising:

(a) an effective amount of one or more curcuminoids and an effective amount of at least one senolytic flavonoid, wherein the curcuminoids include for example one or more of curcumin, desmethoxycurcumin, and bisdesmethoxycurcumin and the flavonoid from senolytic agents include one or more of quercetin, fisetin, apigenin, luteolin, and rapamycin;

(b) a polyol in an amount sufficient to dissolve the effective amount of the curcuminoid and the flavonoids; and optionally (c) fatty acid, wherein the polyol and the fatty acid are in a ratio ranging from about 10:1 to about 50:1 by weight, wherein the amounts of the polyol and the fatty acid are selected so that upon administration the effective amount of the active agent(s) is(are) delivered transdermally or transmucosally following topical application.

In some embodiments, the curcuminoid is curcumin. In some embodiments, the other active is least either one flavonoid from one of the following: quercetin, apigenin, fisetin, luteolin or another small biocompatible senolytic agent such as rapamycin. In some embodiments, the formulation includes combinations of curcuminoids with senolytic agents such as quercetin and apigenin.

The formulation and kit disclosed herein can be applied to the treatment of various conditions or diseases. Examples include transdermal treatment of acute and chronic inflammatory conditions, transdermal prevention and reversal of endothelial dysfunction, risk reduction of cytokine storm or cytokine storm phenomena (release of an abnormal level or a higher than normal level of pro-inflammatory cytokines) in patients with conditions that create underlying endothelial dysfunction, for example COVID-19 or SARS-CoV-2 infection, topical treatment of dermatological conditions, anti-aging skin treatments, ophthalmological conditions, aerosol based treatments of pulmonary conditions, topical treatments of infections, treatment of red blood cells to improve storage properties and reverse storage lesions thus improving safety and efficacy of stored red blood cells, loading red blood cells with therapeutic agents prior to transfusion, stabilizing red blood cells via intravenous (IV) delivery of RBC stabilizing agents, IV interventions to treat cytokine storm phenomena and related acute inflammatory crises, aerosol treatment and prevention of acute respiratory distress syndrome (ARDS) and other conditions that destroy lung tissue through excessive oxidative damage and the ensuing inflammation, and loading medical sponges with therapeutic agents for use, for example in the ear, nose, mouth, rectum, and vagina. Sustained transdermal systemic delivery can also be achieved to harness the therapeutic potential of NO for various chronic diseases and conditions.

The formulation may additionally include polyphenols, flavonoids, stilbenoid, secosteroid and other phytochemicals and natural products which promote formation of NO. In some embodiments, the NO booster comprises at least one of an agent selected from the group consisting of polyphenol, flavonoid, stilbenoid, secosteroid, and natural products of the like. In some embodiments, the curcuminoids include at least one of curcumin, desmethoxycurcumin, bisdesmethoxycurcumin, quercetin, berberine, resveratrol and vitamin D.

In some embodiments, the polyol is polyethylene glycol having a molecular weight ranging from 100 to about 1000. In some embodiments, the fatty acid is myristic acid.

In some embodiments, the formulation provides continued release of the NO booster or the NO releasing agent from the NO precursor (e.g. S-nitrosothiol-containing molecule) over a period of about 8, about 10, about 15, about 20, about 24 or about 48 hours.

In some embodiments, the formulation further includes a thickener which keeps the transdermal formulation in a semi-solid or solid form. In some embodiments, the thickener is petroleum jelly, cocoa butter or polyalkylene glycol of MW of more than 2k Da.

Another aspect of this invention provides a kit or transdermal delivery system, incorporating the transdermal formulation disclosed herein. In some embodiments, the transdermal delivery system is a kit or nebulizer.

Another aspect of this invention provides a blood sample preparation method for slowing the onset or progression of storage lesion of red blood cells ex vivo in the sample in comparison with an untreated reference during storage. The method includes mixing the red blood cells with a solution comprising an effective amount of a curcuminoid and optionally a flavonoid. In some embodiments, more than 60%, more than 70%, more than 80%, more than 90%, or more than 95% of the red blood cells remain viable after 10, 15, 20, 30, 40, 50, 60, 80 days or longer.

In some embodiments, the effective amount is selected such that inflammation, hemolysis or microparticle formation is reduced by at least 20% in comparison with an untreated reference over the same period of time. In some embodiments, the effective amount is selected such that adenosine triphosphate (ATP) and/or 2,3-diphosphoglycerate (2,3-DPG) levels reduces by less than 5%, less than 10%, less than 20%, less than 30% or less than 40% in a specified period of time. In some embodiments, the effective amount is selected such that adenosine triphosphate (ATP) and/or 2,3-diphosphoglycerate (2,3-DPG) levels are higher than that of an untreated reference or control over the same period of time by more than 5%, more than 10%, more than 20%, more than 30%, or more than 40% over the same specified period of time. In some embodiments, the specified period of time is 10, 15, 20, 30, 40, 50, 60, 80 days or longer.

In some embodiments, the sample is maintained at a temperature ranging from about −30° C. to about 37° C. the sample is harvested from a healthy individual.

In some embodiments, the concentration of the curcuminoid in the solution ranges from about 1 mM to about 10 M, from about 10 mM to about 10 M, from about 100 mM to about 10 M, from about 1 M to about 10 M or from about 5 M to about 10 M prior to mixing with the red blood cells. In some embodiments, the solution has a pH ranging from about 5.5 to about 7.0, from about 6 to about 7.0, or from about 6.5 to about 7.0. In some embodiments, the solution further comprises a fatty acid. In some embodiments, the fatty acid is myristic acid.

In some embodiments, the concentration of the curcuminoid in the sample ranges from about 0.2 to about 20, from about 0.5 to about 10, from about 1 to about 10, or from about 1 to about 5 mM in the sample.

In some embodiments, the method includes depleting oxygen and/or carbon dioxide in the sample.

In some embodiments, the solution comprises a solvent selected from the group consisting of polyethylene glycol, ethanol, acetone, ethyl acetate, acetonitrile, DMF, THF, DMSO, isopropanol, 1-butanol, xylenes, n-hexane, n-heptane and any combination thereof. In some embodiments, the solvent comprises polyethylene glycol. In some embodiments, the solvent consists essentially of PEG. In some embodiments, the solvent and the curcuminoid are in a ratio ranging from about 5:1 to about 40:1, from about 5:1 to about 30:1, from about 5:1 to about 20:1, or from about 5:1 to about 10:1 by weight. In some embodiments, the curcuminoid is curcumin. In some embodiments, the solution is substantially free from water.

Another aspect of this invention provides an ex vivo blood sample comprising red blood cells, an agent comprising a curcuminoid and optionally a flavonoid in a solvent, wherein the agent is in an effective amount to prolong the viability of the red blood cells or slow the onset or progression of storage lesion of red blood cells ex vivo in the sample, and wherein the solvent is sufficient to keep the agent dissolved in the sample. The ex vivo blood sample can be provided with the method described herein. In some embodiments, the concentration of the agent in the sample ranges from about 0.2 to about 20, from about 0.5 to about 10, from about 1 to about 10, or from about 1 to about 5 mM in the sample. In some embodiments, the agent comprises curcumin. In some embodiments, the agent comprises curcumin and at least a flavonoid.

A related aspect provides a method of transfusing blood to a subject in need thereof. The method includes transfusing the blood sample disclosed herein to the subject.

Another aspect provides a method of enhancing the efficacy of transfusion of blood, comprising administering to a subject in need thereof a transdermal formulation, wherein the transdermal formulation comprises
  (a) an effective amount of a curcuminoid, wherein the curcuminoid is selected from the group consisting of curcumin, desmethoxycurcumin, and bisdesmethoxycurcumin;
  (b) a polyol in an amount sufficient to dissolve the effective amount of the curcuminoid; and optionally
  (c) fatty acid, wherein the polyol and the fatty acid are in a ratio ranging from about 10:1 to about 50:1 by weight,
wherein the amounts of the polyol and the fatty acid are selected so that upon administration the effective amount of the NO booster is delivered transdermally.

In some embodiments, the curcuminoid is curcumin. In some embodiments, the transdermal formulation further comprises at least a flavonoid is selected from quercetin, apigenin, fisetin, luteolin, and rapamycin. In some embodiments, the transdermal formulation comprises curcumin and further comprises at least one of quercetin and apigenin. In some embodiments, the transdermal formulation comprises curcuminoids ranging from about 3% to about 10% by weight.

In some embodiments, the transdermal formulation further comprises at least one flavonoid, wherein the curcuminoid and the at least one flavonoid are in a ratio ranging from about 1:1 to about 10:1. In some embodiments, the transdermal formulation includes quercetin and apigenin in a ratio ranging from about 1:1 to about 10:1.

In some embodiments, the transdermal formulation comprises myristic acid. In some embodiments, the polyol is selected from the group consisting of polyethylene glycol, polypropylene glycol, ethylene glycol, propylene glycol, and glycerol. In some embodiments, the polyol is polyethylene glycol having a molecular weight ranging from 200 to about 600. In some embodiments, the polyol and the curcuminoid are in a ratio ranging from about 8:1 to about 12:1.

In some embodiments, the blood is the ex vivo blood sample disclosed herein, which exhibited prolonged viability of the red blood cells or slowed onset or progression of storage lesion. In some embodiments, the transdermal formulation is administered prior to the transfusion of the blood.

DETAILED DESCRIPTION OF THE INVENTION

Embodiments of this disclosure provide transdermal formulations and methods of enhancing systemic NO levels. Also provided are formulations and methods for enhancing viability of red blood cells ex vivo and improving efficacy of blood transfusion. Because NO has known systemic benefits including the capability of reversing inflammation, preventing and reversing endothelial dysfunction, repolarizing activated macrophages, deactivating activated platelets, protecting the endothelial lining of blood vessels and antimicrobial/antiviral activity, the formulations of this disclosure can be applied to the treatment of various diseases and conditions. In some embodiments, the treatment is based on transdermal delivery of agents that can either improve nitric oxide production in the endothelium or directly release NO from appropriate S-nitrosothiol containing molecules. The formulations disclosed herein are capable of enhancing endothelial production of NO and decreasing ROS levels through the lowering of CD38 levels.

The transdermal formulations described herein have the advantage of reduced side effects in comparison with conventional oral administration of active agents. Oral curcumin for instance can result in GI upset (hypermotility, increased acid production in stomach) especially when chronically used. Delivery of the agent over skin or mucosa bypasses the GI tract and achieves desirable therapeutic effect while minimizing side effects.

While the following text may reference or exemplify specific embodiments of a formulation, a kit or a method relating to the treatment or prevention of a disease, it is not intended to limit the scope of the formulation, kit or method to such particular reference or examples. Various modifications may be made by those skilled in the art, in view of practical and economic considerations, such as the specific form of the formulation and the amount or frequency of administration of the formulation for treating or preventing a disease or condition.

The articles "a" and "an" as used herein refer to "one or more" or "at least one," unless otherwise indicated. That is, reference to any element or component of an embodiment by the indefinite article "a" or "an" does not exclude the possibility that more than one element or component is present.

The term "about" as used herein refers to the referenced numeric indication plus or minus 10% of that referenced numeric indication. In some embodiments, "about" refers to the referenced numeric indication plus or minus 5% of that referenced numeric indication.

The term "agent" or "active agent" refers to a molecule or compound that prevents, alleviates or ameliorates symptoms of disease, prolongs the survival of the subject being treated, or reaches a desirable/acceptable medical or sanitary condition. An agent in the NO booster increases systemic production of NO in a subject. An agent in the NO precursor releases NO or undergoes a reaction to generate another agent, which after being transdermally delivered into blood circulation releases NO.

The term "body cavity" includes any opening and/or surface area within the opening on a subject's body. Nonlimiting examples of body cavity include nose, nasal sinuses, mouth, ears, rectum, vagina, open wound, sore, buccal cavity and mucosal surface (e.g. gum).

The term $C_{1-30}$ alkyl includes, branched or nonbranched, alkyl groups having any number of carbons ranging from 1 to 30. Non-limiting examples include methyl, ethyl, propyl, and butyl.

The term "cytokine storm" refers to dysregulated abnormal systemic release of pro-inflammatory cytokines leading to diseases and has also been referred to as "cytokine release syndrome" or "inflammatory cascade". Often, a cytokine storm or cascade is referred to as being part of a sequence because one cytokine typically leads to the production of multiple other cytokines that can reinforce and amplify the immune response. Generally, these pro-inflammatory mediators have been divided into two subgroups: early mediators and late mediators. Early mediators, such as e.g., tumor-necrosis factor, interleukin-1, interleukin-6, are not sufficient therapeutic targets for re-establishing homeostatic balance because they are resolved within the time frame of a patient's travel to a clinic to receive medical attention. In contrast, the so-called "late mediators" have been targeted because it is during this later "inflammatory cascade" that the patient realizes that he or she has fallen ill.

The term "ex vivo" in the context of a biological material (e.g. blood, tissue or organ) refers to the biological material being outside the living body.

The term "inflammatory disease or disorder" may refer to any disease, disorder or syndrome in which an excessive or unregulated inflammatory response results in a transient inflammatory condition, damage to host tissue, or loss of tissue function. "Inflammatory diseases" also refer to pathological conditions mediated by granulocyte influx and/or neutrophil chemotaxis and transient inflammatory conditions including "brain fog" due to chemotherapy and leaky gut syndrome.

The term "long Covid" refers to side effects or symptoms attributed to Covid that become manifest well after the seeming recovery from the primary infection. Nonlimiting examples of long Covid symptoms include brain fog, fatigue, achiness, clotting issues, myocarditis, and edema.

The term "NO booster" refers to an agent or a mixture of agents that increase systemic production of NO in a subject. The NO booster itself does not release NO.

The term "NO precursor" refers to an agent or a mixture that directly or indirectly through a derivative releases NO. The NO precursor may be or include an agent containing a NO releasing moiety and is transdermally delivered into blood circulation of a subject before releasing NO. Nonlimiting examples of such a NO releasing agent include S-nitroso-Glutathione (GSNO), S-nitroso-N-acetylcysteine (SNAC), S-Nitroso-N-acetylpenicillamine (SNAP), and S-nitroso-human serum albumin (SNO-HAS). Alternatively, a NO precursor may include an agent that leads to a derivative containing a NO releasing moiety, and the derivative releases NO after being transdermally delivered into blood circulation. Nonlimiting examples of agents that lead to NO releasing derivatives include glutathione, N-acetyl cysteine (NAC), N-acetylpenicillamine, and cysteine, which can be nitrosated at the thiol group to produces a S-nitrosothiol-containing derivative.

The term "semisolid" refers to a flexible and deformable solid form. Free flowing liquid and rigid solid forms are excluded from semisolid. Non-limiting examples include gels, ointments, creams, emulsions, microemulsions, nanoemulsions, pastes, balms, lotions, and mousses.

The term "subject" encompasses any animal, but preferably a mammal, e.g., a human, a non-human primate, a dog, a cat, a horse, a cow, or a rodent. More preferably, the subject is a human.

The term "pharmaceutically acceptable salts" means salts of compounds of the present invention which are pharmaceutically acceptable and possess the desired pharmacological activity. Non-limiting examples of such salts include acid addition salts formed with inorganic acids such as hydrochloric acid, hydrobromic acid, sulfuric acid, nitric acid, and phosphoric acid; or with organic acids such as 1,2-ethanedisulfonic acid, 2-hydroxyethanesulfonic acid, 2-naphthalenesulfonic acid, 3-phenylpropionic acid, 4,4'-methylenebis (3-hydroxy-2-ene-1-carboxylic acid), 4-methylbicyclo [2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, and trimethylacetic acid. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Non-limiting examples of acceptable organic bases include ethanolamine, diethanolamine, triethanolamine, tromethamine, and N-methylglucamine. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "therapeutically effective amount" or "effective amount" refers to an amount of an active agent effective to prevent, alleviate or ameliorate symptoms of disease, prolong the survival of the subject being treated, or reach a desirable/acceptable medical or sanitary condition. Determination of a therapeutically effective amount or effective amount is well within the capability of those skilled in the art, especially in light of the detailed disclosure provided herein. In the context of blood storage or transfusion the term "effective amount" as used herein also refers to the amount of an agent that will maintain the viability or function of the biological sample (e.g. cell, tissue, or organ).

The term "treating" or "treatment" of any disease or condition refers, in some embodiments, to ameliorating the disease or disorder (i.e., arresting or reducing the development of the disease or at least one of the clinical symptoms thereof). In some embodiments "treating" or "treatment" refers to ameliorating at least one physical parameter, which may not be discernible by the subject. In some embodiments, "treating" or "treatment" refers to modulating the disease or disorder, either physically, (e.g., stabilization of a discernible symptom), physiologically, (e.g., stabilization of a physical parameter), or both. In some embodiments, "treating" or "treatment" refers to delaying the onset of the disease or disorder, or even preventing the same. For instance, a treatment can be a "prophylactic treatment" is to be construed as any mode of treatment that is used to prevent progression of the disease or is used for precautionary purpose for persons at risk of developing the condition.

The term "transdermal" or "transdermally" refers to delivery, administration or application of a formulation containing an active agent by means of direct contact with skin or mucosa and then transport of the agent through the skin or mucosa into blood circulation of a subject. Such delivery, transport, administration or application is also known to include dermal, percutaneous, transmucosal and buccal path. As used herein, "dermal" includes skin and mucosa, which includes oral, buccal, nasal, rectal and vaginal mucosa. In some embodiments, the term also refers to delivery and transport of an agent through a cell wall (e.g. red blood cell wall) into the cell.

The term "transdermal formulation" refers to a composition or formulation of an agent that upon application to the skin or mucosa delivers the agent or a derivative (e.g. a S-nitrosothiol-containing molecule derived from a thiol-containing molecule) of the agent across the skin or mucosa (or any other surface noted above). A transdermal formulation may be in the form of a solution, suspension, gel, ointment, cream, emulsion, microemulsion, nanoemulsion, paste, balm, magma, lotion, mousse, wax, or liposome. A kit or transdermal delivery system incorporating the transdermal formulation may be in the form of, for example, a patch, a swab, a nebulizer, a sprayer, a sponge or a pouch.

The terms "viable cell(s)," "viable tissue(s)," and "viable organ(s)" refers to one or more cells, tissues, and/or organs, respectively, that comprise at least a first population of living cells that are capable of surviving and substantially maintaining their extant biological function provided that they are harvested, stored, maintained, cultured, transported, and/or transplanted under the necessary biological conditions (e.g., nutrients, incubation temperature, etc.) effective to maintain the viability of such cells, tissues or organs sufficient for implantation into a suitable recipient host. When x % (e.g. 60% or 80%) of blood cells in a treated blood sample remain viable after a certain period of time, the percentage value refers to the blood cells that maintain their viability ex vivo out of the original total population of the blood cells. Alternatively, when x % (e.g. 60% or 80%) of blood cells remains in a treated blood sample after a specified time period, the percentage refers to the transfused cells that remain in the circulation for the specified time period.

Transdermal Formulation

An aspect of this disclosure provides a transdermal formulation, which delivers a therapeutically effective amount of an agent transdermally. The formulation generally includes
(a) an effective amount of an active agent such as a CD38 inhibitor, an sirtuin-1 (SIRT1) activating agent, an NO booster and/or an NO precursor, wherein the NO booster increases systemic production of NO, and wherein the NO precursor comprises an NO releasing agent or derives a NO releasing agent,
(b) a solvent in an amount sufficient to dissolve the effective amount of the NO booster or the NO precursor; and optionally
(c) a fatty acid,
wherein upon administration, the effective amount of active agent (e.g. the sirtuin-1 (SIRT1) activating agent, the NO booster and/or the NO releasing agent) is delivered transdermally. In some embodiments, the active agent is delivered into blood vessels for the active agent to enter systemic circulation from arteries or veins. In some embodiments, the active agent is delivered into deep layers of the skin (e.g. the upper epidermal layers or the lower epidermal layers below the stratum corneum).

In some embodiments, the agent in the transdermal formulation is a flavonoid or a curcuminoid, or a combination thereof. One or more flavonoids and/or one or more curcuminoids can be included in the formulation. For instance, the formulation may contain one or two flavonoids such as quercetin and apigenin, optionally in combination with curcumin, wherein each of the ingredients or components is in a therapeutically effective amount.

In some embodiments, the transdermal formulation includes one or more flavonoids or a curcuminoid. Nonlimiting examples include a combination of quercetin and apigenin, a combination of quercetin and curcumin, a combination of curcumin and apigenin, and a combination of quercetin and apigenin and curcumin. Whether the combination contains one or more flavonoids or one or more curcuminoids, the ratio by weight between each of the flavonoid and each of the curcuminoid may range independently from about 1:100 to about 100:1, from about 5:100 to about 100:5, from 1:10 to about 10:1, from 2:10 to about 10:2, from 3:10 to about 10:3, from 4:10 to about 10:4, from 5:10 to about 10:5, from 6:10 to about 10:6, or from 8:10 to about 10:8. Nonlimiting examples of the ratio include about 100:1, about 80:1, about 50:1, about 40:1, about 30:1, about 20:1, about 10:1, about 8:1, about 5:1, about 4:1, about 3:1, about 2:1, about 1:1, about 1:2, about 1:3, about 1:4, about 1:5, about 1:8, about 1:10, about 1:20, about 1:30, about 1:40, about 1:50, about 1:60, about 1:80, about 1:100, and any range between any two of the aforementioned values. In some embodiments, the combination contains curcumin and one or both of quercetin and apigenin, wherein ration by mass between curcumin and each of the one or both of quercetin and apigenin independently ranges from about 1:5 to about 10:1, from about 1:5 to about 3:1, from about 1:2 to about 3:1, or from about 1:2 to about 2:1.

When the formulation contains two or more flavonoids (e.g. quercetin, apigenin, fisetin, luteolin, and rapamycin), the ration by weight between two flavonoids may independently range from about 1:100 to about 100:1, from about 5:100 to about 100:5, from 1:10 to about 10:1, from 2:10 to about 10:2, from 3:10 to about 10:3, from 4:10 to about 10:4, from 5:10 to about 10:5, from 6:10 to about 10:6, or from 8:10 to about 10:8. Nonlimiting examples of the ratio include about 100:1, about 80:1, about 50:1, about 40:1, about 30:1, about 20:1, about 10:1, about 8:1, about 5:1, about 4:1, about 3:1, about 2:1, about 1:1, about 1:2, about 1:3, about 1:4, about 1:5, about 1:8, about 1:10, about 1:20, about 1:30, about 1:40, about 1:50, about 1:60, about 1:80, about 1:100, and any range between any two of the aforementioned values. In some embodiments, the formulation includes quercetin and apigenin in a ratio ranging from about 1:1 to about 10:1, from about 2:1 to about 10:1, from about 5:1 to about 10:1, from about 1:1 to about 1:10, from about 1:1 to about 1:5, or from about 1:1 to about 1:2.

The level of NO in a subject can be measured using known technology as disclosed in for example, U.S. Pat. Nos. 9,044,182 and 8,425,428. In some embodiments, an effective amount is an amount sufficient to have a measurable effect on a disease including for example hypertension, inflammation, osteoarthritis, endothelial dysfunction, dermatological condition, ophthalmological condition, bacterial infection, viral infection, ischemia reperfusion injury, hypoxia reoxygenation injury, cytokine storm phenomena, cerebral malaria, Chagas disease, and hemoglobinopathies such as Sickle Cell Disease and HbE/betaThalassemia, type 2 diabetes, and Lupus. In some embodiments, an effective amount is an amount sufficient to have a measurable positive effect on blood flow and/or vasodilation, and/or a measurable negative effect on blood pressure. In some embodiments, the effect on blood flow and/or vasodilation is observed local to the site of topical application. In some embodiments, an effective amount is an amount sufficient to have a measurable effect on an inflammatory disease, e.g., an inflammatory dermatosis, inflammatory bowel disease and inflammation of the general vasculature including the blood brain barrier due to chemotherapy as evidenced by an appropriate clinical parameter, e.g., an improvement in Physician's Global Assessment after treatment with the formulation. In some embodiments, an effective amount is an amount sufficient to obtain a systemic or local level of nitric oxide to have a desired effect, e.g., have a measurable positive effect on blood flow and/or vasodilation, have a measurable negative effect on blood pressure, and/or have a measurable effect on an inflammatory dermatosis disease, e.g., an inflammatory dermatosis as evidenced by an appropriate clinical parameter.

Non-limiting examples of the SIRT1 activating agent the active agent include polyphenol, flavonoid, stilbenoid, secosteroid, and other phytochemicals or natural products which promote formation of NO.

After the NO booster or NO precursor is delivered transdermally, it leads to generation of NO in the body of a subject. The NO booster or NO precursor is in an amount effective to increase NO systemically or locally to a level high enough to achieve the objective of treating a disease or condition. In some embodiments, the NO booster comprises polyphenol, flavonoid, stilbenoid, secosteroid, or natural products that promote NO production. In some embodiments, the NO precursor comprises a S-nitrosothiol-containing molecule, or a thiol-containing molecule and a nitrite source. In some embodiments, the NO booster contains one or more of curcuminoids, flavonoids, berberine, resveratrol, vitamin D source and their pharmaceutically acceptable salts and derivatives. Curcuminoids are linear diarylheptanoids and include for example curcumin, desmethoxycurcumin, and bisdesmethoxycurcumin. Flavonoids have a 3-hydroxyflavone backbone and include for example apigenin, 3-hydroxyflavone, azaleatin, fisetin, galangin, gossypetin, kaempferol, kaemferol, isorhamnetin, morin, myricetin, natsudaidain, pachypodol, quercetin, rhamnazin, and rhamnetin. Non-limiting examples of vitamin D source includes vitamin D2 and vitamin D3, and any precursors to vitamin D. Nonlimiting examples of polyphenols including plant extracts, brazilin, and theaflavins (e.g. theaflavin (TF-1), theaflavin-3-gallate (TF-2a), theaflavin-3'-gallate (TF-2b), and theaflavin-3, 3'-digallate (TF-3)).

In some embodiments, the NO booster consists essentially of curcumin, desmethoxycurcumin, bisdesmethoxycurcumin, quercetin, berberine, resveratrol, vitamin D source and any combination thereof.

In some embodiments, the formulation contains both a NO booster and a NO precursor. For instance, the combination of curcumin and an NO releasing agent (e.g. S-nitrosothiol-containing molecule or thiol-containing agent) in the polyol/fatty acid system can be a potent formulation for treating localized inflammation and infections and at the same time provide the systemic benefits of curcumin to control systemic inflammation.

Additional examples of curcuminoids include methylcurcumin, demethoxy curcumin, bisdesmethoxycurcumin, sodium curcuminate, dibenzoylmethane, acetylcurcumin, feruloyl methane, tetrahydrocurcumin, 1,7-bis(4-hydroxy-3-methoxyphenyl)-1,6-heptadiene-3,5-dione (curcumin1), 1,7-bis(piperonyl)-1,6-heptadiene-3,5-dione (piperonyl curcumin) 1,7-bis(2-hydroxy naphthyl)-1,6-heptadiene-2,5-dione (2-hydroxyl naphthyl curcumin) and 1,1-bis(phenyl)-1,3,8,10 undecatetraene-5,7-dione. In some embodiments the NO booster is curcumin, or a synthetic curcumin that is 80%, 85%, 90% or 98% pure diferuloylmethane.

In some embodiments, the transdermal formulation includes, as an active ingredient for treating a disease or condition, one or more curcuminoids and optionally one or more of polyphenol, flavonoid, stilbenoid, secosteroid, or natural products that promote NO production. In some embodiments, the transdermal formulation includes one or both of curcumin and quercetin, and optionally one or more of one or more of polyphenol, flavonoid, stilbenoid, and secosteroid.

The NO precursor is either S-nitrosothiol-containing molecule or a mixture containing a thiol-containing molecule and a nitrite source. When in contact with an acid source, the nitrite source gives rise to nitrous acid, which can then nitrosate the reactive thiol of the thiol-containing molecule. The S-nitrosothiol-containing molecule releases NO to the subject in need thereof.

Various thiol-containing molecules can be used as a precursor. Examples include glutathione, N-acetyl cysteine (NAC), N-acetylpenicillamine, cysteine, and their derivatives. The amino group of either cysteine or NAC can be acetylated with acetyl or other carbonyl of different carbon length (e.g. $COC_{2-30}$ alkyl). By adjusting the length of the carbon chain, the solubility and lipophilicity of the molecule can be modified. Similarly, the carboxylic group of cysteine can be converted into an ester (e.g., ethyl ester, or other substituted or unsubstituted $C_{3-30}$ alkyl ester) or an amide having $NR_2$ moiety (wherein each R is independently H or other substituted or unsubstituted $C_{3-30}$ alkyl). Variation of the carbon chain allows for modulation of the properties of the molecule.

Various inorganic compounds can serve as a nitrite source. Nonlimiting examples of the nitrite source include an alkali metal nitrite, an alkaline earth metal nitrite, a transition metal nitrite and an ammonium nitrite. In some embodiments, the nitrite source is potassium nitrite, sodium nitrite, rubidium nitrite, strontium nitrite, barium nitrite, calcium nitrite, copper nitrite, zinc nitrite, or mixtures thereof. The nitrite can also comprise a natural source such as extracts of lettuce and spinach. In some embodiments, the nitrite source is saturated in the polyol solvent. The nitrite source can also be comprised of nitrite loaded nanoparticles.

Nitrite loaded nanoparticles can be prepared by techniques known in the art including for example procedures report in U.S. Pat. No. 8,333,997, the entire disclosure of which is hereby incorporated by reference. To limit NO release from the nanoparticles during production, the medium should maintain a pH above 7.5 or so throughout the preparation. The nitrite loaded nanoparticles can then be mixed with solvent system of polyol and fatty acid (e.g. PEG400 and myristic acid) and remain stable until exposed to an aqueous environment. In the presence of thiol containing molecules, the nitrite loaded nanoparticles will allow for the formation of S-nitrosothiols when the mixture is exposed to an acid source or slightly acid aqueous environment on the skin.

The use of the nitrite loaded nanoparticles allows for the use of high concentrations of nitrite under hydrophobic conditions. The combination of the nitrite loaded nanoparticles with the solvent system of polyol and fatty acid (e.g. PEG400 and myristic acid) regardless of the other included deliverables, allows for a stable mixture that will both release NO and S-nitrosate thiols when exposed to an aqueous environment. There is no release of nitrite or production of NO in the viscous solvent until water or an acid source is introduced.

The acid source may be separately packed from the mixture containing a thiol-containing molecule and a nitrite source and mixed with the nitrite prior to administration. For instance, the nitrite source and the acid source can be separately enclosed in permeable or frangible pouches. The amount and concentration of the acid can be adjusted depending on the amounts of other agents and the nature of the acid. Nonlimiting examples of the acid include acetic acid, oxalic acid, and citric acid.

Nonlimiting examples of S-nitrosothiol-containing molecules include S-nitroso-Glutathione (GSNO), S-nitroso-N-acetylcysteine (SNAC), S-Nitroso-N-acetylpenicillamine (SNAP), and S-nitroso-human serum albumin (SNO-HAS) Similar to a thiol-containing molecule, these S-nitrosothiol-containing molecules can be modified by varying the carbon chain in the respective ester, amide, or N-acyl moiety to fine tune their properties.

A solvent such as a polyol suitable for the delivery system allows for high concentrations of poorly soluble agents. In addition, it should be biocompatible with a profile as safe for biomedical applications. Moreover, it will ideally facilitate skin and mucosal permeation to allow for transdermal delivery. Nonlimiting examples of polyols include polyethylene glycol, polypropylene glycol, ethylene glycol, propylene glycol, and glycerol. In some embodiments, the polyol is polyethylene glycol (PEG). In some embodiments, the PEG has a molecular weight ranging from about 100 to about 2000, from about 100 to about 1000, from about 100 to about 800, from about 100 to about 600, from about 200 to about 600, or from about 200 to about 400 daltons. In some embodiments, the formulation is substantially free from water.

Other examples of solvents for formulations disclosed herein may include glycol, ethanol, acetone, ethyl acetate, acetonitrile, DMF, THF, DMSO, isopropanol, 1-butanol, xylenes, n-hexane, n-heptane, PEG and any combination thereof. For instance, the solvent may include PEG with one or more of acetone, tetrahydrofuran, and n-hexane. In further examples, the solvent may be a combination of acetone and tetrahydrofuran, a combination of acetonitrile and tetrahydrofuran, or a combination of n-hexane and tetrahydrofuran.

In some embodiments, the solvent of the formulation consists essentially of the polyol. In some embodiments, the formulation may include one or more additional solvents. Nonlimiting examples include mineral oil, petrolatum, castor oil, essential oils such as eugenol, menthol, cineole, or rose oil, n-methyl pyrrolidone, vegetable oils, oleyl alcohol, dipropylene glycol, polyoxyethylene derivative of sorbitan esters, saturated polyglycolized $C_{8-10}$ glycerides, polyoxyethylated fatty acid glycerides, oleic acid, dimethylsulfoxide (DMSO), fatty alcohol, isopropyl myristate (IPM), triacetin, ethyl oleate, isostearic acid, medium chain fatty acid and other fatty acids, and mixtures thereof. In addition to dissolving the agent, these solvents can also serve as plasticizer so that the formulation can be flexible, stretchable, moldable and/or otherwise skin friendly.

In some embodiments, the polyol solvent is low molecular weight polyethylene glycol (PEG) with a molecular weight ranging from about 50 to about 2000, from about 50 to about 1000, from about 100 to about 1000, from about 100 to about 800, from about 100 to about 700, from about 100 to about 600, from about 200 to about 800, from about 200 to about 600, or from about 200 to about 400 daltons. Nonlimiting examples of the molecular weight of the polyol solvent include about 100, include about 200, include about 300, include about 400, include about 500, include about 600, include about 800, and include about 1000. Short chain PEG molecules such as PEG200 and PEG400 that are liquid at ambient temperatures are particularly useful.

Other solvents that may be used alone or in combination with the polyol for dissolving curcuminoid or flavonoid include deep eutectic solvents (DES) and natural deep eutectic solvents (NADES). Nonlimiting examples of NADES include sugars (e.g. glucose, sucrose, fructose), organic acids (e.g. lactic, malic, citric acids), urea and choline chloride. NADES can also be used in combinations including derivatives of organic acids (e.g. emalic acid, proline, betaine), choline chloride (e.g. choline chloride, d(−) fructose; choline chloride, A-1 rhamnose; choline chloride, lactic acid), different sugars (fructose, sucrose; glucose, sucrose, fructose) and other combinations (betaine, sucrose; betaine, d-(+) glucose, proline).

The solvent may also be based on a colloidal delivery system, which includes for example micelles (e.g. produced from surfactants with a hydrophobic core for encapsulation of curcumin), microemulsions (e.g. produced from aqueous and organic phases stabilized by surfactants suitable for curcumin incorporation in the hydrophobic core), conventional emulsions and nanoemulsions (organic phase (oil) surrounded by hydrophilic emulsifier; encapsulation of curcumin in the core oil phase), pickering emulsions (oil in water emulsions stabilized by nanoparticles appropriate for encapsulation of curcumin in the core oil), multilayered emulsions (e.g. prepared by layer-by-layer deposition (lbl) layers of charged emulsifiers surrounding an interior oil phase incorporating curcumin), solid lipid nano/microparticles (slns/slms) (e.g. produced by cooling oil in water emulsions to form crystallized lipid particles that can incorporate lipophilic curcumin), liposomes and nano-liposomes (e.g. particles with hydrophilic core and hydrophobic shell prepared with phospholipids that can encapsulate curcumin), hydrogels (micro/nano-gels) (e.g. porous network of biopolymer networks suitable for encapsulating curcumin).

Other solvents include dimethyl sulfoxide (DMSO), ethanol (EtOH), polyethylene glycol 400 (PEG 400), dimethyl acetamide (DMA), N-Methyl-2-pyrrolidone (NMP), dimethyl sulfoxide (DMSO), dimethyl isosorbide (DMI), propylene glycol, glycerin, propylene carbonate, ethanol, acetone, ethyl acetate, acetonitrile, isopropanol, 1-butanol, xylenes, n-hexane, n-heptane, and any combination thereof. The aforementioned solvents can be used alone or in combination and their amounts can be readily adjusted using routine procedures without undue experiments.

The fatty acid serves as a permeation enhancer. Nonlimiting examples of fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, myristic acid and any combinations thereof. In some embodiments, the fatty acid is myristic acid. Mid-sized fatty acids such myristic acid and/or other fatty acids of comparable size/molecular weight are particularly useful. In some embodiments, the formulation does not contain fatty acid or contains only a trace or an insignificant amount of fatty acid.

In some embodiments, the permeation enhancer consists essentially of a fatty acid or ester thereof. In some embodiments, the formulation may contain one or more additional permeation enhancers. Non-limiting examples include surfactants, alcohols, fatty alcohols and glycol, esters, fatty acid esters and fatty alcohol esters, esters of long chain fatty acids with methyl, ethyl, isopropyl alcohols, esters of fatty alcohols with acetic acid, lactic acid as well as oleic acid, diethanolamine, essential oils, terpene and terpenoids, amides, urea, polyoxyethylene fatty alcohol ethers, polyoxyethylene fatty acid esters, sulfoxide, ether alcohol, pyrrolidones, transcarbam, capsaicin derivatives, dimethylamino acid esters, peptides, iminosulfuranes, dicarboxylic acid esters, nanocarriers, triglycerides, hydrocarbons, phospholipids either alone or in combinations thereof.

By adjusting the amount and ratio of the polyol, the fatty acid, and the NO booster or the NO precursor, the solubility of the fatty acid and the agent in the NO booster or the NO precursor as well as the physical state (e.g. liquid or gel or semisolid) of the formulation and the release profile of the active agent can be controlled. The ratio between the polyol and the fatty acid impacts the form of the solution and generally ranges from about 5:1 to about 500:1, from about 5:1 to about 100:1, from about 1:1 to about 100:1, from about 20:1 to about 100:1, from about 30:1 to about 100:1, from about 20:1 to about 80:1, from about 20:1 to about 60:1, from about 50:1 to about 10:1, or from about 30:1 to about 50:1 from about 40:1 to about 10:1, from about 40:1 to about 10:1, from about 20:1 to about 60:1, from about 20:1 to about 15:1, from about 18:1 to about 12:1 by weight. In some embodiments, the concentration of the fatty acid in the polyol ranges from about 0.01 M to about 1 M, from about 0.01 M to about 0.8 M, from about 0.01 M to about 0.6 M, from about 0.01 M to about 0.4 M, from about 0.01 M to about 0.2 M, from about 0.01 M to about 0.15 M, from about 0.01 M to about 0.1 M, from about 0.02 M to about 0.2 M, from about 0.02 M to about 0.1 M, from about 0.04 M to about 0.08 M, or from about 0.06 M to about 0.1 M. In further exemplary embodiments, the concentration of the fatty acid in the polyol is about 0.01 M, about 0.02 M, about 0.03 M, about 0.04 M, about 0.06 M, about 0.08 M, about 0.1 M or about 0.12 M. In some embodiments, the fatty acid is saturated in the polyol. In some embodiments, the polyol is PEG. In some embodiments, the fatty acid is myristic acid.

The scope and amount of polyol and fatty acid are as described above and can be modified by one of ordinary skill in the art in view of the practical needs without undue experiments. In some embodiments, the fatty acid is selected from myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, caprylic acid, capric acid, lauric acid, myristic acid, palmitic acid, stearic acid, arachidic acid, behenic acid, lignoceric acid, cerotic acid, and any combinations thereof. In some embodiments, the polyol is selected from the group consisting of polyethylene glycol, polypropylene glycol, ethylene glycol, propylene glycol, glycerol, and combinations thereof. In some embodiments, the polyol is polyethylene glycol having a molecular weight ranging from 200 to about 600. In some embodiments, the polyol and the fatty acid are in a ratio ranging from about 5:1 to about 100:1 by weight.

The fatty acid may range from about from about 0.1% to about 30%, from about 0.5% to about 20%, from about 1% to about 15%, from about 1% to about 10%, from about 1% to about 5%, from about 2% to about 8%, or from about 4% to about 8% of the total weight of the NO booster or NO precursor, the polyol and the fatty acid (if present) or the total weight of the formulation. Nonlimiting examples of the amount of the fatty acid include about 1%, about 3%, about 5%, about 7%, about 8%, or about 10% by weight.

Water may cause aggregation and microparticle formation. In some embodiments, the transdermal formulation is anhydrous or substantially free from water. Minimizing or eliminating water from the formulation can help with maintaining uniform distribution of the fatty acid and/or the active ingredient (e.g. NO booster or NO precursor) in the polyol (e.g. PEG). In some embodiments, water in the transdermal formulation is less than 5%, less than 2%, less than 1%, less than 0.5%, less than 0.1%, or less than 0.01% by weight.

In some embodiments, the transdermal formulation includes at least one water repelling agent, also referred to as a water repellant. Examples of water repelling agents include silicones, such as cyclomethicone, dimethicone, simethicone, $C_{26-28}$ alkyl dimethicone, $C_{26-28}$ alkyl methicone, polyphenylsisquioxane, trimethylsiloxy silicate and crosspolymers of cyclopentasiloxane and dimethicone/vinyltrimethylsiloxysilicate, and blends thereof. The water repelling agent may be particularly useful in embodiments where the topical vehicle is used with a water-reactive agent, such as a nitric oxide-releasing agent whereby the nitric oxide is released in the presence of water (e.g., a diazeniumdialate or sodium nitrite). In other cases, such as when the active agent is not water sensitive, a water repelling agent may or may not be included.

Depending on the therapeutic goal of the formulation, the active agent in the formulation (e.g. CD38 inhibitor, NO booster or NO precursor or mixtures thereof) ranges from about 0.05% to about 80%, from about 0.05% to about 50%, from about 0.05% to about 35%, from about 0.05% to about 30%, from about 0.05% to about 20%, from about 0.05% to about 10%, from about 0.1% to about 20%, from about 0.1% to about 10%, from about 0.1% to about 5%, from about 0.5% to about 20%, from about 0.5% to about 10%, from about 0.5% to about 5%, from about 1% to about 20%, from about 1% to about 10%, or from about 1% to about 5% of the total weight of the NO booster or NO precursor, the polyol and the fatty acid (if present) or the total weight of the formulation. Nonlimiting examples of the amount of the active agent in the formulation include about 1%, about 3%, about 5%, about 7%, about 8%, about 10%, about 12%, and about 15% by weight in the formulation. In some embodiments, the amount of each active agent in the formulation or in a dosage unit of the formulation independently ranges from about 0.001 mg to about 20 g, about 0.002 mg to about 20 g, about 0.004 mg to about 20 g, about 0.006 mg to about 20 g, about 0.008 mg to about 20 g, about 0.01 mg to about 20 g, from about 0.05 mg to about 20 g, from about 0.1 mg to about 20 g, from about 0.1 mg to about 5 g, from about 0.1 mg to about 2 g, from about 0.1 mg to about 1 g, from about 1 mg to about 5 g, from about 1 mg to about 1 g, from about 10 mg to about 100 mg, from about 5 mg to about 50 mg, or from about 10 mg to about 30 mg in a dosage unit of the formulation. A dosage unit can be a physically distinct package form (e.g. a capsule, a patch, a vial). A dosage unit can also be a predetermined portion of the formulation for each individual administration. For instance, a suitable amount as a dosage unit of the formulation can be taken out of a container for direct topical application or for loading onto a patch or any suitable carrier before being applied topically. The amount or size of the dosage unit can be readily adjusted depending on the intended use and the area of application. Nonlimiting examples of the amount of each active agent in a dosage unit independently include about 0.001 mg, about 0.002 mg, about 0.004 mg, about 0.006 mg, about 0.008 mg, about 0.01 mg, about 0.02 mg, about 0.04 mg, about 0.06 mg, about 0.08 mg, about 0.1 mg, about 0.2 mg, about 0.4 mg, about 0.06 mg, about 0.08 mg, about 1 mg, about 2 mg, about 5 mg, about 10 mg, about 20 mg, about 30 mg, about 40 mg, about 50 mg, about 60 mg, about 80 mg, about 100 mg, about 200 mg, about 300 mg, about 400 mg, about 500 mg, about 600 mg, about 800 mg, about 1 g, about 2 g, about 5 g, about 10 g, about 15 g, about 20 g, about 25 g, about 30 g, about 35 g, about 40 g, about 50 g, about 60 g, about 80 g, about 100 g, and any range between any two of the aforementioned values. In some embodiments, each active agent in a dosage unit independently ranges from about 0.01 to about 1 mg, from about 0.01 to about 0.5 mg, or from about 0.1 to about 0.5 mg. In some embodiments, the agent is curcuminoids, which is selected from one, two or three of curcumin, desmethoxycurcumin, and bisdesmethoxycurcumin, optionally in combination with one or more flavonoids as described above. The dosage unit can be administered once, twice, three times a day or as needed. In some embodiments, the dosage unit is administered once every day, every two days, every three days, every four days, every five days, every six days, every seven days, or every ten days.

In some embodiments, the ratio between each active agent and the polyol independently ranges from about 1:5 to about 1:100, from about 1:5 to about 1:50, from about 1:5 to about 1:30, from about 1:5 to about 1:20, from about 1:8 to about 1:15, or from about 1:10 to about 1:15 by weight. In some embodiments, the polyol is PEG. In some embodiments, the fatty acid is myristic acid. In some embodiments, the formulation is substantially free from piperine. Depending on the disease or condition to be treated and the location of administration, the ratio and amount of the PEG, fatty acid and active agent may be selected so that the resulting formulation is a liquid, a gel or other suitable form. Additional agents may be added to control the physical state of the formulation.

In some embodiments, the transdermal formulation contains PEG, myristic acid and/or other fatty acids of comparable size/molecular weight, and one or more active agents. In some embodiments, the transdermal formulation contains PEG, myristic acid and/or other fatty acids of comparable size/molecular weight, an active agent and a secondary agent. In some embodiments, the transdermal formulation contains PEG, myristic acid, and an active agent selected from at least one of curcumin, desmethoxycurcumin, bis- desmethoxycurcumin, quercetin, berberine, resveratrol and vitamin D. In some embodiments, the transdermal formulation contains PEG, myristic acid, and one or more an active agent selected from at least one of curcumin, desmethoxycurcumin, bisdesmethoxycurcumin, quercetin, berberine, resveratrol and vitamin D, and an NO precursor or secondary agent. In some embodiments, the transdermal formulation contains PEG having a molecular weight ranging from about 200 to about 500 (e.g. PEG 200, PEG300, PEG 400, or PEG 500). The ratio between the PEG and the myristic acid (and/or other fatty acids of comparable size/molecular weight) ranges from about 5:1 to about 100:1 (e.g. 6:1, 8:1, 10:1, 12:1, 15:1, 18:1, 20:1, 25:1, 30:1, 40:1, 50:1, 60:1, or 80:1) by weight. The ratio between the PEG and the NO booster (e.g. curcumin) ranges from about 5:1 to about 100:1 by weight. Nonlimiting examples of the ratio between the PEG and the NO booster include 6:1, 8:1, 10:1, 12:1, 15:1, 18:1, 20:1, 25:1, 30:1, 40:1, 50:1, 60:1, 80:1, and any range between any two of the aforementioned values. In some embodiments, the formulation contains curcumin. In some embodiments, the formulation contains curcumin, desmethoxycurcumin, bisdesmethoxycurcumin, or any combination thereof. In some embodiments, the formulation contains vitamin D. In some embodiments, the concentration of an individual active ingredient in the formulation ranges from about 0.01 M to about 1 M, from about 0.05 M to about 0.5 M, from about 0.05 M to about 0.3 M, or from about 0.1 M to about 0.2 M. Nonlimiting examples of the concentration of an active ingredient (e.g. curcumin) in the polyol (e.g. PEG) include about 0.06 M, about 0.08 M, about 0.1 M, about 0.12 M, about 0.14 M, about 0.16 M, about 0.18 M, about 0.20 M, about 0.25 M, about 0.30 M, about 0.40 M, about 0.60 M, and about 0.80 M.

The transdermal formula has an extended shelf life with minimum amount of decomposition of the active ingredient(s). In some embodiments, the active ingredient(s) of the formulation remain stable by more than 95% or more than 99% for a period of a least 1 month, at least 3 months, at least 6 months, or at least 12 months. In some embodiments, the transdermal formulation includes one or more curcuminoids, myristic acid and PEG. The one or more curcuminoid ranges from about 2% to about 10%, from about 3% to about 8% or from about 4% to about 6% in the formulation by weight. Myristic acid ranges from about 1% to about 10%, from about 1% to about 8%, from about 2% to about 8% or from about 4% to about 6% in the formulation by weight. PEG ranges from about 60% to about 95%, from about 70% to about 90%, from about 80% to about 90% or from about 95% to about 90% in the formulation by weight. In some embodiments, the PEG is PEG400.

In some embodiments, the formulation further includes a gelling agent or thickener which keeps it in a semi-solid form or solid form. Nonlimiting examples of gelling agents or thickeners include carbomers, methyl cellulose, hydroxypropylmethyl cellulose, poloxamers, polyacrylic acid, alginate, chitosan, xanthan gum, gellan gum, xyloglucan, paraffins, silicone, petroleum jelly, cocoa butter and polyalkylene glycol of high molecular weight. Additional examples include polyethylene oxide, ammonia methacrylate, carrageenan, cellulose acetate phthalate aqueous such as CAPNF from Eastman, carboxy methyl cellulose Na, carboxy polymethylene, cellulose, cellulose acetate (microcrystalline), cellulose polymers, divinyl benzene styrene, ethyl cellulose, ethylene vinyl acetate, silicone, polyisobutylene, shellac (FMC BioPolymer), guar gum, guar rosin, cellulose derivatives such as hydroxy ethyl cellulose, hydroxy methyl cellulose, hydroxy propyl cellulose, hydroxypropyl methyl cellulose, carboxymethyl cellulose, and methyl cellulose, hypromellose phthalate (hydroxypropyl methylcellulose phthalate), methyl acrylate, microcrystalline wax, polyvinyl alcohol, polyvinyl acetate, polyvinyl acetate phthalate such as Suretic from Colorcon, PVP ethyl cellulose, polyvinylpyrrolidone (PVP), acrylate, PEG/PVP, trimethyl siloxysilicate, maleic acid/anhydride copolymers, polacrilin, poloxamer, poly glactic acid/poly-1-lactic acid, terpene resin, locust bean gum, prolamine (Zein), acrylic copolymers, polyurethane dispersions, gelatin (both type A and type B from various sources such as pig, cattle, and fish), dextrin, starch, polyvinyl alcohol-polyethylene glycol copolymers, methacrylic acid-ethyl acrylate copolymers such as BASF's Kollicoat polymers, methacrylic acid and methacrylate based polymers such as poly(methacrylic acid) copolymers and methylmethacrylate copolymers, including Rohm and Haas' Eudragit polymers (Eudragit (E, L, NE, RL, RS, S100)), Esters of polyvinylmethylether/maleic anhydride copolymer such as Gantrez ES-425, Gantrez ES-225 available from ISP, and mixtures thereof. Nonlimiting examples of polyalkylene glycol of high molecular weight include PEG and polypropylene glycol (PPG). The polyalkylene glycol may have a molecular weight of more than 1k, more than 2k, more than 3k, more than 4k, more than 6k, more than 8k, more than 10k, more than 15k, more than 20k, more than 25k, or more than 30k Daltons. Without limiting in scope the semisolid formulation can be in the dosage form of an ointment, gel, cream, emulsion, paste, lotion or liposome.

In some embodiments, the formulation includes a combination of small and large polyalkylene glycols, which have a MW difference ranging from 500 to 5000, from 1000 to 3000, from 1000 to 2000, or from 1500 to 2000 Daltons. By adjusting the ratio between the two or more polyalkylene glycols, viscosity and rate/extent of both skin penetration and uptake by the circulation can be controlled. For instance, the combination may include one or both of PEG and PPG each having a MW ranging from 100 to 2000, from 200 to 2000, from 400 to 1000, or from 500 to 800 Daltons. The combination may also include one or both of PEG and PPG each having a higher MW ranging from 800 to 5000, from 1000 to 3000, or from 1000 to 2000 Daltons. In further exemplary embodiments, one of polyalkylene glycols has MW of 100, 200, 400, 600, or 800, and another of the polyalkylene glycols has MW of 1000, 1500, 2000, 2500, or 3000. In some embodiments, the combination include a PEG of 400 and a PEG of 2000 Daltons. In some embodiments, the ratio between the low MW polyalkylene glycol and the high MW polyalkylene glycol ranges from about 10:1 to about 1:10, from about 5:1 to about 1:5, from about 2:1 to about 1:2 by weight. Further exemplary ratios between the low MW polyalkylene glycol (e.g. PEG and/or PPG) and the high MW polyalkylene glycol (e.g. PEG and/or PPG) include 10:1, 8:1, 6:1, 4:1, 2:1, 1:1, 1:2, 1:4, 1:6, 1:8 and 1:10.

In some embodiments, the formulation does not include additional therapeutic agent other than the NO booster or NO precursor. In some embodiments, the active agent in the formulation consists essentially of the NO booster and/or NO precursor described herein. In some embodiments, the formulation may include an additional therapeutic agent including for example an antioxidant, an antibiotic, antiviral and/or antifungal agent.

The formulation may include other components including, for example, solubilizers, skin immersion enhancers, surfactants, cosolvents, thickener or viscosifying agents, preservatives, isotonizing agents, isoosmotizing agents, absorption enhancers of the agent, mucoadhesive polymers, non-mucoadhesive polymers, chelants, stabilizers, antioxidants, and mixtures thereof.

In some embodiments, the thickener is selected from one or more of carbomers, methyl cellulose, hydroxypropylmethyl cellulose, poloxamers, polyacrylic acid, alginate, chitosan, xanthan gum, gellan gum, xyloglucan, paraffins, silicone, petroleum jelly, and cocoa butter.

Nonlimiting examples of solubilizers include, but are not limited to, diethylene glycol monoethyl ether (ethoxydiglycol, commercially available as Transcutol®) and diethylene glycol monoethyl ether oleate (Soficutol®). Commercially available under the tradename of Poly™); polyethylene castor oil derivatives such as polyoxy 35 castor oil, polyoxy 40 hydrogenated castor oil; polyethylene glycol, especially low molecular weight polyethylene glycols; Polyethylene glycol derivatives such as caprylic/capric acid glycerides (commercially available as Labrasol®); alkylmethyl sulfoxides such as DMSO; pyrrolidones such as 2-pyrrolidone and N-methyl-2-pyrrolidone; and DMA. Many solubilizers can also function as absorption enhancers. A single solubilizer can be incorporated into the formulation, or a mixture of solubilizers can be incorporated into the formulation.

Nonlimiting examples of skin immersion enhancers help to facilitate the passage of therapeutic levels of active agents to pass through reasonably sized areas of unbroken skin. Suitable enhancers are well known in the art and include, for example, lower alcohols such as methanol, ethanol and 2-propanol; alkylmethyls such as dimethylsulfoxide (DMSO), decylmethylsulfoxide (C 10 MSO) and tetradecylmethylsulfoxide. sulfoxides; urea; 2-pyrrolidone, N-methyl-2-pyrrolidone and N-pyrrolidone such as -(hydroxyethyl) pyrrolidone N, N-diethyl-m-toluamide; C 2-C 6 alkane diols; dimethylformamide (DMF), N,N-dimethylacetamide (DMA) and miscellaneous solvents such as tetrahydrofurfuryl alcohol; and 1-substituted azacycloheptan-2-ones, especially 1-n-dodecylazacycloheptan-2-one (laurocapram. Available from Whitby Research Incorporated, Richmond, Va. under the tradename Azone®).

Among surfactants there may be mentioned, for example, polyethoxylated glycerides, polysorbates, poloxamers, sodium lauryl sulphate, phospholipids, such as phosphatidylcholine or phosphatidylglycerol and their derivatives, polyoxyethylenated hydrogenated castor oil, polyoxyethylenated fatty acids, mixtures of mono-, di-, and triglycerides of fatty acids optionally polyoxyethylenated, and mixtures thereof.

Among preservatives there may be mentioned, for example, benzalkonium chloride, boric acid, benzoic acid, C1-4 alkyl esters of p-hydroxybenzoic acid, chlorobutanol, benzyl alcohol, phenylethyl alcohol, organometallic derivatives of mercury, polyquaternium such as polyquaternium 1, and mixtures thereof.

Among isotonizing and isoosmotizing agents there may be mentioned, for example, inorganic salts such as sodium chloride, dextrose, trehalose, mannitol, amino acids, and mixtures thereof.

Among mucoadhesive polymers there may be mentioned, for example, hyaluronic acid, polygalacturonic acid, polyacrylic acid, carboxymethyl amylose, carboxymethyl chitin, chondroitin sulphate, methyl cellulose, gelatin, hydroxymethyl cellulose, hydroxypropyl cellulose, hydroxypropylmethyl cellulose, sodium carboxymethyl cellulose, xanthan gum, chitosan, carbopol, polycarbophil, gellan gum, carrageenan, alginates, pectin, poloxamer, and mixtures thereof. Among non-mucoadhesive polymers there may be mentioned, for example, polyvinyl alcohol. Among chelants there may be mentioned, for example, disodium edetate, and disodium cromoglycate. Among antioxidants there may be mentioned, for example, sodium metabisulfite, sodium bisulfite, acetylcysteine, ascorbic acid, and mixtures thereof.

By adjusting the amount and ratio of the polyol, the fatty acid, and the one or more active agents, the solubility of the fatty acid and the active agent as well as the physical state of the formulation and the release profile of the active agent can be controlled. In some embodiments, the polyol, the fatty acid, the active ingredient and other necessary components are configured in a ratio such that the formulation provides a rapid onset of action within about 5 minutes, within about 10 minutes, within about 15 minutes, or within about 30 minutes.

The transdermal formulation disclosed herein can provide extended or continued release of the agent (e.g. CD38 inhibitor, NO booster or the S-nitrosothiol-containing molecule). In some embodiments, the formulation provides extended release of the agent (transdermal delivery into blood circulation) for a period of 30 minutes, 1 hour, 2 hours, 4 hours, 8 hours, 10 hours, 12 hours, 15 hours, 18 hours, 24 hours, about 2 days, about 3 days, about 5 days, or about 7 days. By selecting the polyol solvent and the fatty acid in a suitable ratio, the rate of the release can also be controlled. In some embodiments, one, two or three of the following parameters can be achieved for the formulation:

(a) less than 15%, less than 20%, less than 25%, less than 30%, or less than 35% of the agent is delivered into blood circulation within about 30 minutes, within about 1 hour, about 2 hours, about 3 hours, about 4 hours, or about 5 hours;

(b) from about 25% to about 90%, from about 30% to about 85%, from about 35% to about 70%, from about 40% to about 70%, from about 50% to about 60%, from about 35% to about 50%, from about 40% to about 60% or from about 35% to about 80% of the agent is delivered into blood circulation within about 6 hours, about 8 hours, about 10 hours, about 12 hours, or about 14 hours; and (c) more than 60%, more than 70%, or more than 80% of the agent is delivered into blood circulation in about 16 hours, about 18 hours, about 20 hours, about 22 hours, about 24 hours, about 36 hours, or about 48 hours.

In some embodiments, the active agent and the carriers (e.g. polyol or fatty acid) and their amounts in the formulation are selected so that a window of therapeutic effect is maintained for about 30 minutes, about 1 hour, about 2 hours, about 4 hours, about 6 hours, about 8 hours, about 10 hours, about 12 hours, about 14 hours, about 24 hours, about 2 days, about 3 days, about 5 days, or about 7 days, wherein the plasma concentration of the active agent varies by less than 5%, less than 10%, less than 15%, less than 20%, less than 25%, less than 30% or less than 40% during such a window. In some embodiments, the window starts within about 10 minutes, within about 20 minutes, within about 30 minutes, within about 1 hour, or within about 2 hours after the formulation is administered.

The formulation may include a secondary agent. Examples of secondary agents include hypertension agents, antimicrobial agents, anti-inflammatory agents, analgesic agents, anesthetic agents, antihistamine agents, antiseptic agents, immunosuppressants, antihemorrhagic agents, vasodilators, wound healing agents, anti-biofilm agents and mixtures thereof. Alternatively, the secondary agents can be in a separate formulation and/or is separately administered from the transdermal formulation described herein.

Examples of anti-inflammatory agents include nonsteroidal anti-inflammatory agents (NSAIDs); propionic acid derivatives such as ibuprofen and naproxen; acetic acid derivatives such as indomethacin; enolic acid derivatives such as meloxicam, acetaminophen; methyl salicylate; monoglycol salicylate; aspirin; mefenamic acid; flufenamic acid; indomethacin; diclofenac; alclofenac; diclofenac sodium; ibuprofen; ketoprofen; naproxen; pranoprofen; fenoprofen; sulindac; fenclofenac; clidanac; flurbiprofen; fentiazac; bufexamac; piroxicam; phenylbutazone; oxyphenbutazone; clofezone; pentazocine; mepirizole; tiaramide hydrochloride; steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

In some embodiments, the formulation contains an antiviral agent such as acyclovir, trifluridine, idoxuridine, penciclovir, famciclovir, cidofovir, gancyclovir, valacyclovir, podofilox, podophyllotoxin, ribavirin, abacavir, delavirdine, didanosine, efavirenz, lamivudine, nevirapine, stavudine, zalcitabine, zidovudine, amprenavir, indinavir, nelfinavir, ritonavir, saquinavir, amantadine, interferon, oseltamivir, ribavirin, rimantadine, zanamivir, and combinations thereof. Anti-viral treatment may be used to treat both localized and systemic viral infections, such as Covid-19, cold sores or genital herpes.

Examples of antimicrobial agents include penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenen, amikacin, netilmicin, fosfomycin, gentamycin, ceftriaxone, Ziracin, Linezolid, Synercid, Aztreonam, and Metronidazole, Epiroprim, Sanfetrinem sodium, Biapenem, Dynemicin, Cefluprenam, Cefoselis, Sanfetrinem celexetil, Cefpirome, Mersacidin, Rifalazil, Kosan, Lenapenem, Veneprim, Sulopenem, ritipenam acoxyl, Cyclothialidine, micacocidin A, carumonam, Cefozopran and Cefetamet pivoxil.

Examples of antihistamine agents include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetic agents include dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine and dyclonine hydrochloride.

Examples of antiseptic agents include alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of analgesic agents include alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include alcohols such as phenol; benzyl benzoate; calamine; chloroxylenol; dyclonine; ketamine; menthol; pramoxine; resorcinol; troclosan; procaine drugs such as benzocaine, bupivacaine, chloroprocaine; cinchocaine; cocaine; dexivacaine; diamocaine; dibucaine; etidocaine; hexylcaine; levobupivacaine; lidocaine; mepivacaine; oxethazaine; prilocaine; procaine; proparacaine; propoxycaine; pyrrocaine; risocaine; rodocaine; ropivacaine; tetracaine; and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of antihemorrhagic agents include thrombin, phytonadione, protamine sulfate, aminocaproic acid, tranexamic acid, carbazochrome, carbaxochrome sodium sulfanate, rutin and hesperidin. Additional examples of secondary or additional agents include chemotherapeutics (tyrosine kinase inhibitor, immune checkpoint inhibitor, VEGF inhibitor, etc) and glucose lowering medications (e.g. Metformin).

Additional examples of secondary agents include daunorubicin, daunomycin, dactinomycin, doxorubicin, epirubicin, idarubicin, esorubicin, bleomycin, maphosphamide, ifosfamide, cytosine arabinoside, bischloroethyl-nitrosourea, Busulfan, mitomycin C, actinomycin D, mithramycin, prednisone, hydroxypregesterone, testosterone, tamoxifen, dacarbacine, procarbazine, hexamethylmelamine, pentamethylmelamine, mitoxantrone, amsacrine, chlorambucil, methylcyclohexylnitrosourea, nitrogen mustard, Melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-Fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol. In some embodiments, secondary agents that can be used in combination with the formulation disclosed herein or incorporated into the same transdermal formulation include anti-inflammatory agents, analgesics, antibacterial agents, antifungal agents, antibiotics, vitamins, and antioxidants. In some embodiments, the secondary agent is selected from piperine, anthranilic acid, benzophenone, camphor derivatives, cinnamic acid esters (for example, octyl methoxycinnamate), dibenzoylmethane (for example, butyl-methoxydibenzoylmethane), p-aminobenzoic acid (PABA) and its derivatives, salicylic acid esters, and PDE5 inhibitors (e.g. sildenafil (Viagra), tadalafil (Cialis), vardenafil (Levitra), and avanafil (Stendra)).

Any of the secondary agents described herein can be incorporated in the same transdermal formulation. Alternatively, in some embodiments of any method disclosed herein, a secondary agent can be administered separately from the transdermal formulation via any suitable route including oral, transdermal and parenteral routes.

In some embodiments, a combination of active agents in the transdermal formulation produces a synergistic therapeutic effect. For example, curcumin and a PDE5 inhibitor, when incorporated in the same transdermal formulation or administered sequentially in conjunction with each other can lead to early symptomatic recovery (fever, cough, sore throat, and breathlessness), less deterioration, fewer red flag signs in patients with viral infections (e.g. COVID-19).

Transdermal Delivery System

A kit or a transdermal delivery system may contain, in an amount sufficient for at least one agent, any combination of the components described herein, and may further include instructions recorded in a tangible form for use of the components. In some applications, one or more components may be provided in pre-measured single use amounts in individual, typically disposable, patches, tubes or equivalent containers.

The formulation disclosed herein can be incorporated into a transdermal delivery system or kit and used as a patch, swab, aerosol, cream, sponge, sprayer, nebulizer or via other suitable means. The transdermal delivery system may also include an instruction manual on the administration of the formulation and one or more of the treatment methods disclosed in this patent document. A liquid or semisolid formulation can be directly applied to the skin for example with a swab or a sponge. Alternatively, a transdermal delivery system may include a layer coated or impregnated with the liquid, semisolid, or solid transdermal formulation. For instance, a patch may have a layer impregnated with the liquid formulation or coated with a semisolid or solid formulation. A transdermal delivery system may also include an adhesive member for attaching it to the skin.

The transdermal delivery system or kit can be in any suitable shape for applying to a subject in need thereof. For example, a sponge loaded with the formulation disclosed herein can be shaped as a circular, cylindrical, cone, planar, tubular, and other symmetrical or asymmetrical shape) for inserting into a body cavity or attaching or applying to a target location, and may include an applicator or applicator portion. The sponge can be made from a material which absorbs liquid through capillary action. Alternatively, the material may be hydrophilic or hygroscopic or coated with a hydrophilic or hygroscopic layer that exhibits affinity for aqueous solution, especially water moisture for example from the site or body cavity where the reservoir is placed. A sponge with absorbent characteristics can be made from natural or synthetic materials, which include for example polyester, polyurethane, and vegetal cellulose.

In some embodiments, the formulation is incorporated into a liquid reservoir. The reservoir can be used independently, or it can be attached to or enclosed partially or completely in a sponge. Alternatively, the content of the liquid reservoir, after necessary processing or mixing with an additional agent, can be loaded to a sponge for application. In formulations involving a nitrite source that requires an acid to generate nitrous acid and NO, the acid can be added to the reservoir containing the nitrite prior to administration. Alternatively, a dual liquid reservoir system can be employed. For instance, a pouch contains thiol-containing molecule and nitrite in polyol solvent system and a separate pouch contains the acid source. Of course, additional pouches can be used to enclose the thiol-containing molecule or nitrite or fatty acid separately. Prior to administration or upon contact with the skin, the contents of the pouches are mixed to initiate the reaction between the acid and nitrite and subsequent nitration of the thiol-containing molecule. The pouches for enclosing the NO precursor or the acid source are generally frangible or permeable containers, which do not contact each other or are separated by a non-permeable and removable barrier prior to administration of the formulation. Upon administration, the acid and the NO precursor can permeate out of their respective pouches to mix with each other under pressing from the user after removal of the barrier. The acid and the NO precursor can also be mixed simply by breaking the pouches upon or prior to administration. In a further exemplary embodiment, the acid and the NO precursor are mixed in a container prior to administration. The resulting mixture is soaked up with a swab, a sponge, or an absorbing patch and then applied to the skin.

In some embodiments, the pouch has a permeable or semi-permeable membrane surface that is optionally coated with an adhesive for affixing the membrane to the skin. Instead of adhesive coating, the pouch can also be affixed to the skin by holding the pouch to the skin and then covering the pouch with an adhesive patch or enclosing sheet. Commercially available pouchstock material such as DuPont's SURLYN® can be also used for liquid reservoir. Additional examples include coextruded ethylene acrylic acid/low-density polyethylene (EAA/LDPE) material, or BAREX® from INEOS (acrylonitrile-methyl acrylate).

In some embodiments where the NO precursor is a mixture of thio-containing molecule and nitrite, the formulation can be incorporated into a patch. A layer of the patch is impregnated with the NO precursor in the polyol and fatty acid solvent system, whereas the acid source is disposed in a separate layer. The two layers do not come into contact with each other until attachment of the patch to skin or before administration. By applying pressure to the patch, contents of the different layers can be mixed. Alternatively, the patch includes a non-permeable barrier between the two layers and removal of the barrier before administration allows for mixing the nitrite and acid.

In some embodiments, the formulation is a solid which contains a thickener or solidifying material such as cocoa butter. In some embodiments, the formulation is a solid or semisolid which contains petroleum jelly. The solid or semisolid formulation can be applied to the skin or melt when rubbed with pressure on to the skin.

In some embodiments, the formulation is filled into a nebulizer or sprayer, which delivers the agent in aerosol form to the nose, mouth, or lung of a subject in need. Carbon dioxide or other suitable gas can be used as a propellant.

The systems or kits can comprise any number of additional reagents or substances that are useful for practicing a method of the invention. The kits or systems of the invention can be provided at any temperature. For example, for storage of kits including certain S-nitrosothiol-containing molecules in a liquid or gel, they may be provided and maintained at a suitable temperature, or around 0° C.

The kits or systems can also include instruction manuals and packaging materials for holding the container or combination of containers. Instructions, such as written directions or videotaped demonstrations detailing the use of the transdermal formulation for treating target diseases and conditions, can be included with the kit or systems. Typical packaging materials for such kits and systems include solid matrices (e.g., glass, plastic, paper, foil, and the like) that hold the components in any of a variety of configurations (e.g., in a pouch, tube, and the like).

Such kits or systems may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits or systems described herein can be provided, marketed and/or promoted to health providers, including physicians, nurses, pharmacists, formulary officials, and the like. Kits may also, in some embodiments, be marketed directly to the consumer.

Relating to the formulation disclosed herein and its impact to blood, an aspect of this patent document provides a biological material sample (e.g. a cell sample a tissue sample, an organ sample, and a blood sample) which comprises a biological material treated with the formulation disclosed herein. The sample can be prepared for testing, for storage, for transfusion, or for any other suitable purposes. Also provided herein is a kit including the biological material stored in a container. The container can be configured for storage, transportation, transfusion or any other use of the sample.

The biological sample can be prepared by for example washing, rinsing, mixing a biological sample with the formulation disclosed herein. In some embodiments, the biological sample comprises the formulation and an ex vivo biological material. In some embodiments, biological material is blood.

The biological material can be recovered from one animal and implanted into the same species of animal (allograft) or another species of animal (xenograft). The tissue may be from a whole or partial organ, such as a heart valve or an aorta, or from a specific location in the animal, such as cartilage or a tendon from the knee joint.

Exemplary types of mammalian cells which may be recovered, stored, and/or transported using one or more of the methods and formulations described herein include, but are not limited to: chondral cells, cartilaginous cells, osteochondral cells, islet cells, osteogenic cells, neural cells, bone cells, bone marrow cells, adipose cells, fibroblasts, muscle cells, blood, blood components, stem cells, and embryonic stem cells. In some embodiments, the biological material is blood.

Exemplary types of mammalian tissues which may be recovered, stored, and/or transported according to the present invention include, but are not limited to, skin, cartilage, tendons, ligaments; fascia, tibialis, patellas and other bones, heart valves, semi-tendinous tissues, blood vessels, vertebral discs, corneas, lenses, meniscus, hair, adipose tissue, fibrous tissue, neural tissue, connective tissue, and striated, smooth, or cardiac muscle tissue. The cells or tissues may be recovered from human or animal subjects and are then processed and/or cryopreserved (frozen) for later implantation. Allograft tissues, including, but not limited to, heart valves and portions of heart valves, aortic roots, aortic walls, connective tissues including fascia and dura, vascular grafts (including arterial, venous, and biological tubes), and orthopedic soft tissues, such as boned- or non-boned tendons or ligaments, are often subjected to cryogenic preservation. In this manner, a ready supply of these valuable tissues can be made available for later implantation into mammals, especially humans. In addition, viable xenograft tissues from transgenic animals or tissues developed from human or non-human cells that may include differentiated cell types, stem cells, or genetically-modified cells of various origins may be appropriately processed, cryopreserved, and stored for later implantation. Additional examples include engineered cells of tissues or tissue engineered constructs.

Explanted animal tissues, cell populations, and recovered mammalian organs stored or maintained by any one of the methods or processes disclosed herein, or any explanted mammalian cells, tissue, or organ stored in one or more of the disclosed compositions are preferably suitable for implantation into a selected recipient animal, and particularly into a selected recipient mammal Examples of mammalian species into which the explanted tissue may be transplanted, include, but are not limited to, humans, cattle, horses, sheep, pigs, goats, rabbits, dogs, cats, and non-human primates.

In some embodiment of any method disclosed herein, the cell types may include chondral, cartilaginous, osteochondral, islet, osteogenic, neural, bone, bone marrow, adipose, fibroblast, muscle, blood, and stem cells; the animal tissues may include skin, bone, cartilage, tendon, ligament, vertebral disc, cornea, lens, meniscus, hair, striated muscle, smooth muscle, cardiac muscle, adipose tissue, fibrous tissue, neural tissue, and connective tissue; or the mammalian organs may include cochlea, testis, ovary, stomach, lung, heart, liver, pancreas, kidney, intestine, and eye.

Cell populations, tissues and organs prepared by the processes provided herein may be of any origin, although those of animal origin and of mammalian origin in particular, are preferable. Exemplary explanted biological materials may be obtained from one or more animals, including, but not limited to, bovines, canines, caprines, equines, felines, gallines, humans, lapines, leporines, lupines, murines, ovines, porcines, vulpines, or non-human primates.

Due to their high affinity for red blood cells, curcuminoids (e.g. curcumin) and/or flavonoids when loaded to red blood cells are expected to additionally act as a therapeutic agent through enhanced production and release of either nitric oxide or nitric oxide producing/releasing small molecule-s (nitrosothiols and ferro-NO free heme). Meanwhile, curcuminoid (as well as other botanicals) loaded into red blood cells are expected to exhibit improved pharmacokinetics because they do not readily trigger elimination by the immune system or the liver.

Because the formulation is directly admixed with the blood cells in the blood sample, the amount of the solvent will be increased accordingly to keep the curcuminoid and/or flavonoid dissolved in the mixture or prevent the precipitation of the agent. As described above, the solvent may contain one or more components. The ratio between the solvent and the one or more agents may range from about 5:1 to about 500:1, from about 10:1 to about 200:1, from about 20:1 to about 200:1, from about 20:1 to about 100:1, or from about 50:1 to about 100:1 by weight. Non-limiting examples of the ratio include about 5:1, about 8:1, about 10:1, about 15:1, about 20:1, about 30:1, about 50:1, about 80:1, about 100:1, about 150:1, about 200:1, about 400:1, and any range between any two of the aforementioned ratios. In some embodiments, each agent in the mixture or sample independently has a concentration ranging from about 0.001 to about 100, from about 0.01 to about 50, from about 0.01 to about 10, from about 0.05 to about 10, from about 0.05 to about 5, or from about 0.1 to about 1 µg/mL. Nonlimiting examples of the concentration include about 0.001 µg/mL, about 0.005 µg/mL, about 0.01 µg/mL, about 0.05 µg/mL, about 0.1 µg/mL, about 0.2 µg/mL, about 0.5 µg/mL, about 1 µg/mL, about 2 µg/mL, about 5 µg/mL, about 10 µg/mL, about 15 µg/mL, about 20 µg/mL, about 30 µg/mL, about 50 µg/mL, about 100 µg/mL, about 200 µg/mL, or any range between any two of the aforementioned concentrations. In some embodiments, the formulation disclosed herein has a concentration of the curcuminoid in the solution ranging from about 1 mM to about 10 M, from about 10 mM to about 10 M, from about 100 mM to about 10 M, from about 1 M to about 10 M or from about 5 M to about 10 M prior to prior to mixing with a blood sample.

The agent(s), the solvent and their amounts are selected so that more than 40% of the red blood cells remain substantially viable for the period of at least about 24 hours. In some embodiments, at least 50%, at least 60%, at least 80%, at least 90%, at least 95%, or at least 99% of the red blood cells remain viable for at least 1 day, at least two days, at least three days, at least five days, at least seven days, at least ten days, at least twenty days, at least thirty days, at least forty-five days, at least two months, at least three months, at least four months, or at least six months. In some embodiments, the agent is or consists essentially of curcumin.

In some embodiments, the agent(s), the solvent and their amounts are selected so that the blood sample show an enhanced increase in circulation time after being re-infused into a subject in comparison with a reference sample without being treating with the formulation under the same testing condition. The increase may range from about 2% to about 30%, from about 5% to about 20%, or from about 8% to about 15%. Nonlimiting examples of the increase in circulation time include about 3%, about 5%, about 8%, about 10%, about 12%, about 15%, about 20%, and any range between any two of the aforementioned values. The blood sample thus can serve as both physiological (oxygen delivery) and therapeutic agents (curcumin delivery) when transfused into patients with inflammation-related co-morbidities including for example hemorrhagic shock.

In animal studies, histopathology has shown significant reduction in vascular congestion and iron deposits in male HbSS compared to vehicle in the spleen and in % fields involved in hepatic infarcts and hepatic iron deposits. Together, decreased hemolysis and increased Hb, hematocrit and ATP, suggest red blood cell stabilization, and improved mitochondrial metabolism and reduced oxidative stress and organ damage resulting from the effect of the formulation disclosed herein.

Other biomarkers impacted by the formulation include enhanced ATP level, reduced protein carbonylation, reduction in vascular congestion and/or iron deposits, reduced global inflammatory marker serum amyloid-P, reduced inflammatory cytokines in the skin secretome with or without a concomitant reduction in interleukins, reduced monocyte chemoattractant protein 1 (MCP-1), reduced interferon-gamma (IFN-γ), reduced granulocyte macrophage-colony stimulating factor (GM-CSF), and regulated on activation, normal T-cell expressed and secreted protein (RANTES). In comparison with a reference blood sample with the same constituents except for not being admixed or treated with the formulation disclosed herein, each biomarker independently increases or decreases ranging from about 2% to about 50%, from about 5% to about 40%, from about 5% to about 30%, from about 10% to about 20%, or from about 10% to about 15%. Nonlimiting examples of the increase of decrease for each biomark independently include about 5%, about 10%, about 15%, about 20%, about 25%, about 30%, about 35%, about 40%, about 50%, or any range between any two of the aforementioned values.

These biomarkers are associated with various diseases or conditions. For instance, MCP-1 contributes to neuropathic pain, and inflammation; GM-CSF stimulates granulocyte differentiation and growth. Both RANTES and MCP-1 may also activate mast cells. The formulation disclosed herein thus lead to a significant decrease in cutaneous mast cell degranulation versus vehicle or a reference a sample in sickle subject. The formulation disclosed herein, by transdermal administration or by mixing with blood ex vivo, provides an anti-inflammatory effect by targeting the release of cytokines and inhibiting granulocyte activity.

The above effects on various biomarkers due to the mixing of the formulation and blood ex vivo can also be achieved via administration to a subject with the transdermal formulation disclosed herein. The administration of the transdermal formulation and the transfusion of the treated ex vivo blood sample disclosed herein can both significantly ameliorates hyperalgesia (chronic pain), inflammation, hemolysis, oxidative stress and organ damage, improves mitochondrial function and hematological parameters of SCD pathobiology, provides other disease modifying and anti-nociceptive effects.

The mixture or blood sample may contain additional components such as stabilizer, antibacterial agent and anti-inflammatory agent. For example, myristic acid and other medium sized fatty acids that have potential health can be included as an additive. Saturated fatty acids, such as lauric acid shown to possess antibacterial and anti-inflammatory properties against *P. acnes* can also be included in the blood sample.

Method of Use

Because the transdermal formulation introduces high levels of flavonoids, curcuminoids and/or other potent anti-inflammatory and/or anti-oxidant agents locally and/or systemically, it provides a rapid intervention for various diseases and conditions.

A physiologically natural method of enhancing endothelial production of NO and decreasing ROS levels is through the lowering of CD38 levels. High levels of CD38 creates low levels of NAD+ which in turn creates: i) mitochondrial dysfunction leading to overproduction of ROS; and ii) decreased activity of the Sirtuin proteins. Together, these CD38 consequences result in decreased production of NO from the endothelium and over production of ROS and peroxynitrite from activated macrophages and microglia which promotes endothelial dysfunction. Additionally, there is an interplay between senescent cells and CD38 with each promoting the buildup of the other. The build up of senescent cells in the endothelium not only prevents repair of the endothelial lining of blood vessels but also promotes ongoing endothelial dysfunction, including pathological vascular remodeling and the continued decrease in NO production.

The formulations for sustained transdermal delivery of active agents lead to reduction of CD38 ectoenzyme activities such as NADase activity; thereby enhancing NAD+ levels and promoting the activity of the NAD+ dependent sirtuins. In so doing this approach provides new methods of both preventing and treating various diseases, including for example, those stemming from endothelial dysfunction following either an acute or chronic pro-inflammatory insult, age related decline in physical and cognitive skills, age associated changes in cardiac tissues, vascular hypertrophy, osteoarthritis, peripheral neuropathy and long COVID. Additionally this approach overcomes negative consequences of CD38 overproduction with respect to the ability of stem cells to differentiate into mature cells, which is at least in part responsible for the anemia of chronic inflammation and the lack of efficacy of intrinsic stem cells and stem cell therapy to repair damaged tissues.

The transdermal formulation can be administered in any suitable route to deliver the active ingredient across the skin, mucosa, or membrane of a subject's body. Nonlimiting examples of suitable routes include for example topical (e.g. instillation and mucosal path including vaginal and rectal delivery), pulmonary (e.g. by inhalation or insufflation of powders or aerosols including by nebulizer), intratracheal, intranasal, and epithelial route. In some embodiments, the transdermal formulation includes one or both of curcumin and quercetin, and optionally one or more of one or more of polyphenol, flavonoid, stilbenoid, and secosteroid.

Without being limited to any particular theory, it is postulated that the transdermal formulation disclosed herein delivers an active agent transdermally to a subject and enhances the systemic or local NO level in the subject. In some embodiments, the formulation contains an effective amount of an NO booster to increase systemic or local NO level in the subject. In some embodiments, the formulation contains an effective amount of an NO precursor, wherein the method converts the NO precursor to for example the S-nitrosothiol-containing molecule, which releases NO transdermally to the subject. In some embodiments, the formulation may contain both an NO booster and an NO precursor. In some embodiments the formulation may also contain a secondary agent as defined above.

The transdermal formulation achieves NO enhancement through pathways including up-regulation of endothelial nitric oxide synthase (eNOS), enhancement of the activity of eNOS, and reduction of the levels of ROS. For example, ROS scavenges NO, causes eNOS decoupling resulting in the cessation of eNOS associated NO synthase and instead further production of ROS by eNOS. Meanwhile, loss of the endothelium results in: i) loss the flow mediated mechanotransduction mechanism for controlling NO production from eNOS; and in the loss of the cell free zone next to the endothelium which prevents NO scavenging by hemoglobin in the red blood cells. The transdermal formulation of this patent document provides an effective amount of the active agent the can enhances NO level in the endothelial lining of blood vessels by inhibiting ROS scavenges NO and limiting the degradation of the glycocalyx lining of the endothelium.

The transdermal formulation can be applied to the body surface or body cavity of a subject. For example, the method of enhancing systemic or local NO level or treating a disease or condition may involve inserting, between cheek and gum, a sponge loaded with the formulation disclosed herein.

In diseases or conditions associated with elevated CD38 levels, the transdermal formulation disclosed herein is able to decrease CD38 levels/activity and restore nicotinamide adenine dinucleotide (NAD) thus preventing and reversing many of those consequences of CD38 enhancement. NAD+ (NAD) is a critical coenzyme found in every cell in your body that is involved in hundreds of metabolic processes like cellular energy and mitochondrial health. It is needed for the activity of SIRT1 and SIRT3 which are critical for the control of inflammation, oxidative stress and cellular repair. CD38 is an enzyme found primarily but not exclusively on surface of macrophages and microglial cells. CD38 has NADase activity (breaks down NAD). The amount CD38 on macrophages and microglial cells increases with aging and the onset of acute and chronic inflammation, and as a result, the NAD levels drop resulting in loss of energy, fatigue, increase in inflammatory processes and an inability to restore damages cellular components including DNA. Because the transdermal formulation disclosed herein can effectively lower CD38 levels with little or no side effects, it serves to prevent and limit severe endothelial dysfunction following an acute pro-inflammatory insult, limit age related decline in physical and cognitive skills, reverse age associated changes in cardiac tissue, and stabilize red blood cells.

Certain flavonoids such as apigenin and quercetin in addition to the many anti-inflammatory, anti-oxidative stress properties similar to curcumin, have the added advantage over curcumin by virtue of their senolytic activity. Senescent cells induce increases in CD38 levels. By eliminating senescent cells, one can decrease CD38 levels and thus maintain or restore NAD levels. Additionally CD38 can be decreased when activate Nil macrophages are repolarized to M2 macrophages. Curcumin as well as the flavonoids have the capacity to repolarize macrophages. The uptake of these actives by circulating M1 macrophages via the transdermal/transmucosal route is proposed to be mechanism for rapid reduction of CD38 activity. A CD38 inhibitor can be an agent that repolarizes macrophages, which then lead to reduction of CD38 activities.

A disease or condition associated with an elevated CD38 level refers to those where the subject has been detected to have a higher than normal level of CD38. The normal level of CD38 can be readily obtained from healthy individuals using well-known procedures and statistically acceptable analysis.

Various diseases or conditions can be treated with the transdermal formulation disclosed herein. Nonlimiting examples of the diseases and conditions include age related physical and/or cognitive decline, lupus, rheumatoid arthritis, multiple sclerosis, leukemia's and multiple myeloma, cardiovascular disease, neurodegenerative diseases, COVID-19 symptoms, severity and persistence (long COVID), diabetes, hypertension, neuropathic pain, osteoarthritis, anemia of chronic illness, ALS, Parkinson's, ischemia reperfusion injury, hypoxia reoxygenation injury, transfusion induced injury, radiation induced injuries including dermatitis and neuroinflammation.

Other diseases or conditions treatable with the formulation disclosed herein include muscle structure disorder, neuronal activation disorder, muscle fatigue disorder, muscle mass disorder, metabolic disease, vascular disease, cular vascular disease, muscular eye disease, renal disease, hypertension, inflammation, endothelial dysfunction, dermatological conditions, ophthalmological conditions, bacterial infection, viral infection, ischemia reperfusion injury, hypoxia reoxygenation injury, cytokine storm phenomena, sickle cell disease, inflammatory consequences of an acute sickle cell crisis and other hemoglobinopathies including HbE/betaThalassemia, Chagas disease, type 2 diabetes, Lupus, and transient inflammatory conditions including "brain fog" due to chemotherapy and leaky gut syndrome.

In some embodiments, the disease or condition is a muscle structure disorder selected from Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, or stress urinary incontinence; the neuronal activation disorder is selected from amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder; the muscle fatigue disorder is selected from chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, or thyrotoxic myopathy; the muscle mass disorder is cachexia, cartilage degeneration, cerebral palsy, compartment syndrome, critical illness myopathy, inclusion body myositis, polymyositis, muscular atrophy (disuse), sarcopenia, steroid myopathy, and systemic lupus erythematosus; the beta oxidation disease is selected from systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of b-oxidation (RR-MADD); the metabolic disease is selected from hyperlipidemia, dyslipidemia, hyperchlolesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, Non-alcoholic fatty liver disease (NAFLD), Nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis; the cancer is selected from colon cancer, cancer of the large intestine, skin cancer, breast cancer, prostate cancer, ovarian cancer, and lung cancer; the vascular disease is selected from peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy; the ocular vascular disease is selected from age-related macular degeneration (AMD), stargardt disease, hypertensive retinopathy, diabetic retinopathy, retinopathy, macular degeneration, retinal haemorrhage, and glaucoma; the muscular eye disease is selected from strabismus, progressive external ophthalmoplegia, esotropia, exotropia, a disorder of refraction and accommodation, hypermetropia, myopia, astigmatism, anisometropia, presbyopia, a disorders of accommodation, and internal ophthalmoplegia; and the renal disease is selected from glomerulonephritis, glomerulosclerosis, nephrotic syndrome, hypertensive nephrosclerosis, acute nephritis, recurrent hematuria, persistent hematuria, chronic nephritis, rapidly progressive nephritis, acute renal failure, chronic renal failure, diabetic nephropathy, and Bartter's syndrome.

In some embodiments, the disease or condition is selected from genetic lipodystrophy, non-alcoholic fatty liver disease (NAFLD), non-alcoholic steatohepatitis (NASH), renal ischemia/reperfusion injury (IRI), cardiac ischemia/reperfusion injury, Duchenne & Becker muscular dystrophy, diabetes (type I or type II), obesity, and sarcopenia. the disease or condition is selected from genetic lipodystrophy, non-alcoholic fatty liver disease (NAFLD), non-alcoholic steatohepatitis (NASH), renal ischemia/reperfusion injury (IRI), cardiac ischemia/reperfusion injury, Duchenne & Becker muscular dystrophy, diabetes (type I or type II), obesity, and sarcopenia.

In some embodiments, the disease or condition is selected from Alpers's Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, Pearson Syndrome, platinum-based chemotherapy induced ototoxicity, Cockayne syndrome, xeroderma pigmentosum A, Wallerian degeneration, and HIV-induced lipodystrophy.

In some embodiments, the disease or condition is a neurodegenerative disease including dementia, Alzheimer's disease (AD), Parkinson's disease.

In some embodiments, the disease or condition is a tumor selected from glioblastomas, lung cancer, colon cancer, liver cancer, breast cancer, gastric cancer, bladder cancer, and melanoma.

In some embodiments, the disease or condition is an autoimmune disease selected from diabetes, rheumatoid arthritis (RA), multiple sclerosis (MS), a nd systemic lupus erythematosus (SLE);

In some embodiments, the disease or condition is an inflammatory disease selected from asthma, chronic obstructive pulmonary disease (COPD), pneumonia, and non-alcoholic steatohepatitis (NASH).

In further exemplary embodiments, the transdermal formulation and system can be used as a transdermal therapy for preventing, managing and reversing the clinical consequences of inflammatory diseases including diabetes, COVID-19 infection and sickle cell disease, providing topical treatment of hypertension or topical treatment of osteoarthritis, reversing acute inflammatory cascades (cytokine storm), improving the safety and efficacy of transfused stored red blood cells, treating cerebral malaria or Chagas disease, or treating other early stage acute inflammatory diseases.

Phytochemicals (e.g. curcuminoids) have been shown to have antiviral activity. For instance, it has recently been shown that the glycocalyx can prevent access of viruses to the ACE2 binding receptor on endothelial cells thus limiting uptake and replication. Underlying endothelial dysfunction degrades the glycocalyx thus increasing access of the virus to the ACE2 binding site. Curcumin and many of these other phytochemicals protect and preserve the glycocalyx by reducing ROS production and enhancing endothelial NO production (vide infra). These phytochemicals also reduce the pro-inflammatory insults due to diet and obesity by normalizing lipid and glucose metabolism including insulin production and utilization. For treating toxic chemical and metal triggered inflammation, curcumin and other phytochemicals can chelate and eliminate the toxics from the blood. It also limits the inflammatory response to inhaled toxic agents thus lowering the propensity for the progression towards ARDS. The phytochemicals stabilize red blood cells thus minimizing toxic agent-induced hemolysis which is a potent trigger of inflammation.

The formulations disclosed herein are capable of addressing pro-inflammatory insults including acute inflammatory insults triggered by certain viral infection (e.g. SARS CoV2, Dengue fever, and influenza), obesity and glucose induced inflammatory triggers, and inflammation triggered by exposure to toxic metals and chemicals. For example, in patients with long COVID, side effects attributed to COVID that become manifest well after the seeming recovery from the primary infection include brain fog, fatigue, achiness, clotting issues, myocarditis, edema and more. Most of these long COVID symptoms can be attributed to a continued imbalance between pro-inflammatory and anti-inflammatory factors that favor development of and persistence of endothelial dysfunction. The formulations and methods disclosed herein can be applied to the treatment of these clinical manifestations of long COVID.

In some embodiments of the treatment methods, the transdermal formulation disclosed herein is applied to treating diseases or conditions commonly associated with a "cytokine storm" including but not limited to: COVID-19 infection, sepsis, systemic inflammatory response syndrome (SIRS), cachexia, septic shock syndrome, traumatic brain injury (e.g., cerebral cytokine storm), graft versus host disease (GVHD), or the result of treatment with activated immune cells, e.g., IL-2 activated T cells, T cells activated with anti-CD19 Chimeric Antigen Receptor (CAR) T cells. Besides the impact on endothelial function, active agents such as curcumin at sufficient concentrations acts to efficiently block the binding of the spike protein on SARS CoV 2 to the ACE2 binding site on endothelial cells and pulmonary epithelial cells thus inhibiting viral replication in vulnerable subjects.

In some embodiments of the treatment methods disclosed herein, the transdermal formulation is administered to treat vascular leakage caused by a disease or condition. Nonlimiting exemplary diseases or conditions include vascular leak syndrome, infectious disease, inflammatory diseases, inter alia, sepsis, lupus, irritable bowel disease, inflammatory bowel disease and inflammation of the general vasculature including the blood brain barrier due to chemotherapy. Vascular leakage is characterized by hypotension, peripheral edema, and hypoalbuminemia. Vascular leakage can also be associated with diseases due to pathogens, inter alia, viruses and bacteria.

In some embodiments of the treatment methods disclosed herein, the transdermal formulation is administered to treat or reduce the risk of a cardiovascular disease associated with endothelial dysfunction. Endothelial cells are important constituents of blood vessels that play critical roles in cardiovascular homeostasis by regulating blood fluidity and fibrinolysis, vascular tone, angiogenesis, monocyte/leukocyte adhesion, and platelet aggregation. The occurrence of endothelial dysfunction disrupts the endothelial barrier permeability that is a part of inflammatory response in the development of cardiovascular diseases. Nonlimiting examples of cardiovascular diseases include coronary artery diseases (CAD) such as angina and myocardial infarction (commonly known as a heart attack), stroke, heart failure, hypertensive heart disease, rheumatic heart disease, cardiomyopathy, abnormal heart rhythms, congenital heart disease, valvular heart disease, carditis, aortic aneurysms, peripheral artery disease, thromboembolic disease, and venous thrombosis.

In some embodiments, the amount/dosage of the active agent(s) are selected and/or the administration schedule are configures so that the method increases or decreases the level of a biomarker associated with a cardiovascular disease in the subject by at least about 5%, at least about 10%, at least about 15%, at least about 20%, at least about 30%, at least about 40%, at least about 50%, or at least about 60% in comparison with a control (without treatment with the transdermal formulation) or the level prior to the treatment with the transdermal formulation disclosed herein. Nonlimiting examples of the biomarkers associated with cardiovascular diseases include white blood cell count (WBC), erythrocyte sedimentation rate (ESR), serum C-reactive protein (CRP), cardiac troponin, Creatinine kinase (CK), CK-MB and myoglobin. In some embodiments, the subject prior to the treatment has an abnormal level of one or more biomarkers associated with a cardiovascular disease, wherein the abnormal level of the one or more biomarkers is higher or lower than a normal level or the level of a healthy subject by at least about 5%, at least about 10%, at least about 15%, at least about 20%, at least about 30%, at least about 40%, at least about 50%, or at least about 60%.

Further examples of infectious diseases commonly associated with a "cytokine storm" or vascular leakage include but are not limited to, Coronaviruses (COV's including CoVid-19/(SARS-CoV-2) coronavirus infection), malaria, avian influenza, smallpox, pandemic influenza, adult respiratory distress syndrome (ARDS), severe acute respiratory syndrome (SARS). Certain specific infectious agents include but are not limited to Ebola, Marburg, Crimean-Congo hemorrhagic fever (CCHF), South American hemorrhagic fever, dengue, yellow fever, Rift Valley fever, Omsk hemorrhagic fever virus, Kyasanur Forest, Junin, Machupo, Sabia, Guanarito, Garissa, Ilesha, or Lassa fever viruses. In some embodiments, the infectious disease is caused by virus, bacteria, fungus, helminths, protozoan, or hemorrhagic infectious agents. In some embodiments, the infectious disease is caused by coronaviruses (cov's including covid-19) arenaviridae, filoviridae, bunyaviridae, flaviviridae, or rhabdoviridae virus. In some embodiments, the transdermal formulation and the methods described herein can be applied to the treatment of septic shock syndrome, a chronic inflammatory response to the infectious disease.

The methods disclosed herein can also be applied to the treatment of various types of pain including for example, neuropathic pain, surgery related pain, trauma, periodontal or other dental procedure related pain, and orthopedic or arthritic pain. For instance, pain related with periodontal or other dental procedure can be treated with sponge inserted into a subject's mouth at a suitable location such as between cheek and gum. The transdermal formulation can be administered before or after the onset of pain. For example, the formulation can be administered to a subject prior to a surgical procedure as a prophylactic method to mitigate the pain.

Conventional medications for neuropathic pain have various levels of side effects. The transdermal formulations disclosed herein can be used alone or in combination with conventional drugs, including for example gabapentinoids, tricyclic antidepressants, and/or selective serotonin-norepinephrine reuptake inhibitors as the first-line drugs, lidocaine, capsaicin, and/or tramadol as second-line drugs, and morphine, oxycodone, botulinum toxin-A, and other opioids as third-line treatments. As a result, the transdermal formulations provide the benefit of reduced reliance on conventional pain medication and minimized side effects.

The transdermal formulations can also be applied to postoperative pain management. For individuals undergoing surgeries, including for example, bypass, and thoracic surgery, coronary, groin hernia repair, and leg amputation, the transdermal formulations can serve as alternative therapeutics to treat these aforementioned pain conditions.

As described above, the formulation can be adminstered in any suitable form for the methods disclosed herein. In some embodiments of any formulation or method disclosed herein, the formulation is in a semisolid form or solid form and is rubbed or rolled on the skin or mucosal surface of the subject. In some embodiments, a patch is coated or impregnated with the formulation in a liquid, semisolid or solid form. In some embodiments, one or more of the NO booster, NO precursor and acid source are in a liquid reservoir prior to administration. In some embodiments, the formulation is administered via a sprayer or nebulizer. In some embodiments, the subject is a human. In some embodiments, the presence of symptoms, signs, and/or risk factors of a disease or condition to be treated is determined before beginning administration of the formulation.

The transdermal formulation of this patent document can be administered to activate NAD-dependent deacetylase sirtuin-1 (SIRT1) in a subject. Accordingly, various diseases or conditions associated with dysfunctional SIRT1 can be treated. The sirtuins are a class of NAD+-dependent protein deacetylase enzymes that regulate a wide variety of cellular activities that promote cell survival and extend lifespan in response to environmental stress. Sirtuins exert their effect by removing acetyl groups from certain target proteins in the presence of oxidized nicotinamide adenine dinucleotide (NAD+). For example, the yeast sirtuin enzyme Sir2 (silent information regulator 2), originally identified for its role in silencing transcription of DNA, has also been shown to promote cell survival in response to caloric restriction. Similarly, in *C. elegans*, the sirtuin enzyme SIR-2.1 has been shown to extend lifespan. In mammalian cells, the sirtuin enzyme SIRT1 (a homolog of the yeast Sir2 and *C. elegans* SIR-2.1 enzymes) deacetylates the tumor suppressor p53 to promote cell survival. SIRT1 has been reported to regulate various pathways, including for example, restoring angiogenic function and the secretion of proangiogenic factors in endothelial progenitor cell. Seminal papers have demonstrated that SIRT1 is involved in the protection against excessive inflammation and oxidative stress by deacetylating NFκB and Forkhead box O transcription factors. Furthermore, SIRT1 inhibits cellular senescence, promotes keratinocyte differentiation, and protects against UV-induced DNA damage. Several studies have also demonstrated that downregulated or dysfunctional SIRT1 is associated with various diseases such as in a diabetic milieu and that SIRT1 overexpression improves glucose intolerance and insulin sensitivity and protects against diabetes. Sirtuins therefore appear to be activated as part of a beneficial cellular response to stress, resulting in cell survival and extended lifespan.

Activators of sirtuins may therefore be beneficial in effecting fundamental cellular processes that protect cells from stress and prevent or treat various diseases or conditions, and lengthen healthy life.

Transdermal delivery of the active agent (e.g. NO enhancing and SIRT1 activating therapeutics) allows for facile combination with oral treatments that target other relevant disease pathways not effectively addressed through the transdermally delivered agents. The method includes administering to the subject in need thereof a transdermal formulation disclosed herein. In some embodiments, the formulation includes (a) a therapeutically effective amount of a SIRT1 activating agent; (b) a polyol solvent in an amount sufficient to dissolve the SIRT1 activating agent; and (c) a fatty acid. The SIRT1 activating agent can be one or more NO boosters described above. In some embodiments, the SIRT1 activating agent includes one or more of curcuminoids, berberine, quercetin, resveratrol, and fisetin. The amount of the activating agent can be adjusted depending on the nature of the agent and the disease or condition to be treated. In some embodiments, the activating agent ranges from about 0.05% to about 40% by weight in the formulation. In some embodiments, the formulation provides continued release of the activating agent over a period of about 15 hours.

Treatment of acute and chronic diseases or other conditions can benefit from enhanced systemic nitric oxide levels in the endothelium and/or activation of the SIRT1 and NRF2 signaling pathways. Non-limiting diseases or conditions include sickle cell disease, HbE/betaThalassemia and other thalassemias, diabetic retinopathies, glaucoma, dry eye syndrome, and surgery triggered inflammation.

In some embodiments, the method enhances SIRT1 activity in a subject. The scope and composition of the formulation are as described above. In some embodiments, the formulation includes (a) a therapeutically effective amount of a SIRT1 activating agent; (b) a polyol solvent in an amount sufficient to dissolve the SIRT1 activating agent; and optionally (c) a fatty acid. The SIRT1 activating agent can be one or more NO boosters described above. In some embodiments, the SIRT1 activating agent includes one or more of curcuminoids, berberine, quercetin, resveratrol, and fisetin. The amount of the activating agent can be adjusted depending on the nature of the agent and the disease or condition to be treated. In some embodiments, the activating agent ranges from about 0.05% to about 40% by weight in the formulation. In some embodiments, the formulation provides continued release of the activating agent over a period of about 1, about 2, about 4, about 8, about 10, about 15 or about 24 hours. In some embodiments, the disease or condition is selected from aging, chronic and acute inflammatory condition, chemically induced vascular inflammation, viral infection, bacterial infection, and fungal infection. In some embodiments, the subject the transdermal formulation, diagnosing the subject as having endothelial dysfunction or a disease or condition associated with endothelial dysfunction. In some embodiments, the subject has been diagnosed as having a disease or condition selected from the group consisting of neurodegenerative disease, diabetic kidney disease, diabetes, cardiovascular disease, endothelial dysfunction, muscular dystrophy, pain, neuroinflammatory condition, abnormal vascular homeostasis, and lupus.

The transdermal formulation of this patent document can be administered to promote the therapeutic effect or reduce adverse events of another therapy. In some embodiments of any method disclosed herein, the transdermal formulation of this patent document can be administered prior to, simultaneously with, or subsequent to another therapy, which includes for example orally administered medication, intravenous infusion, intramuscular infusion, topical medical treatment, and/or surgery. In some embodiments, the transdermal formulation is administered prior to an additional therapy for the disease or condition. For instance, topical pretreatment with the formulation disclosed herein before transfusions can maximize tissue perfusion and minimize transfusion associated inflammation. Topical pretreatment with the formulation or concomitant administration with another therapy can also reduce adverse events associated with the therapy (e.g. side effect associated with glucose lowering medications such as Metformin, skin rash, oral cavity mucositis/stomatitis associated with chemotherapeutics).

The transdermal formulation can also enhance endothelial function in a subject. Accordingly, various diseases or conditions associated with dysfunctional or imbalanced endothelial function can be treated. The endothelium has two interrelated major elements that are essential for vascular homeostasis: the glycocalyx and endothelial nitric oxide synthase (eNOS). The hair-like projections from the endothelium called the glycocalyx are responsible for: i) maintaining vascular integrity and thus limiting vascular leakage and access of macrophages and lipids into the deeper layers of the vascular wall (triggers for plaque formation); ii) controlling excessive production of reactive oxygen species (ROS) by acting as depot for superoxide dismutase (SOD) a potent antioxidant; iii) modulation of blood flow in response to physiological demands through sheer stress controlled production of nitric oxide by eNOS; iv) limiting access to and binding to the endothelium of blood borne cells (RBC's monocytes, leukocytes), platelets, and infectious agents; v) limit activation of platelets; vi) prevention of blood flow stagnation; vii) insuring continued NO production by eNOS by preventing eNOS decoupling as a result of excess ROS. In the decoupled state eNOS no longer generates NO but instead produces more inflammation generating ROS; viii) maintaining a cell free zone along the endothelial layer and thus preventing scavenging endothelial generated NO by RBC's in close proximity to the endothelial layer. Meanwhile, nitric oxide generated by endothelial nitric oxide synthase (eNOS) is essential for vascular homeostasis. The critical function of eNO include: i) maintain tissue perfusion/oxygenation; ii) prevent blood flow stagnation; iii) prevent a pro-coagulopathy environment; iv) repolarize activated macrophages and thus promote tissue repair and limit tissue damage; v) regulate pro and anti-inflammatory processes (balance between pro-inflammatory iNOS activity that generates damaging peroxynitrite and anti-inflammatory eNOS activity that produces eNO, activation of SIRT-1); vi) prevent inflammatory damage due to ischemia reperfusion and hypoxia reoxygenation; vii) prevent ROS induced damage including lipid peroxidation and glycocalyx degradation; viii) creates a depot of stored nitrosothiols within the endothelium and surrounding vascular layers that can rapidly provide NO under conditions requiring enhanced levels of NO as in the case of extreme muscular activity.

Endothelial dysfunction is a physiological dysfunction of normal biochemical processes carried out by the endothelium, the cells lining the inner surface of blood vessels. A hallmark of endothelial dysfunction is impaired endothelium-dependent vasodilation, which is mediated by nitric oxide (NO) produced by endothelial nitric oxide synthase (eNOS), a constitutive form of NOS that is principally expressed in endothelial cells. In healthy vasculature, NO produced by the endothelium diffuses to vascular smooth muscle cells (VSMC), where it activates guanylate cyclase and stimulates production of cyclic guanosine monophosphate (cGMP), thereby promoting relaxation of the VSMC and, consequently, vasodilation. Other functions of the endothelium (e.g., inhibition of platelet aggregation, inhibition of leukocyte adherence, and inhibition of VSMC proliferation) are also mediated by NO. In dysfunctional endothelium, NO production is impaired. Endothelial dysfunction can be detected clinically for example by elevations in the number of circulating endothelial cells (CECs).

Endothelial dysfunction is associated with various diseases including for example hypertension, coronary artery disease, heart failure, stroke, peripheral artery disease, diabetes, chronic renal failure, abnormal vascular smooth muscle cell proliferation and other cardiovascular diseases, Type 2 diabetes, insulin resistance and other metabolic syndrome, Lupus, HIV, inflammation resulting from radiation and drug treatments (e.g. chemotherapies), Hemoglobinopathies (Sickle cell disease, HbE/betaThalassemia, Cytokine storm associated conditions induced by viral diseases (e.g. SARS CoV 2, Dengue fever, influenza, hemorrhagic shock, hemorrhagic fevers), erectile dysfunction secondary to surgery induced inflammation, and inflammation associated with increased populations of senescent cells typically occurring with age. Moreover, endothelial dysfunction is thought to be a key event in the development of atherosclerosis and predates clinically obvious vascular pathology by many years. Endothelial dysfunction has also been shown to be of prognostic significance in predicting vascular events including stroke and myocardial infarctions. In addition, endothelial dysfunction was shown to be implicated in inflammation, infection, immune system dysfunction, sleep apnea, sepsis, chronic obstructive pulmonary disease, exposure to pro-inflammatory agents.

The methods disclosed herein are applicable to the treatment of acute consequences as well as chronic consequences of endothelial dysfunction. Examples of chronic consequences of endothelial dysfunction include diseases and conditions described above. In some embodiments, the method is applicable to treating acute consequences including, for example, cytokine storm and associated, physical activity or diet triggered hypoxic/ischemic organ damage (e.g. heart attack due to insufficient tissue perfusion/oxygenation), stroke, micro and macro emboli, pulmonary embolus, ischemia reperfusion injury, hypoxia reoxygenation injury, and long covid which is a consequence of ongoing chronic inflammation/endothelial dysfunction. In some embodiments, the method is applicable to treating chronic consequences including, for example, Cardiovascular disease (CVD), coronary artery disease (CAD), renal failure, cognitive decline and enhanced predisposition to dementia, hypertension, sexual dysfunction, slow healing wounds, accelerated stent failure/closure, coronary artery bypass failure, slow healing wounds, reduced tolerance for physical activity due to mitochondrial dysfunction, accelerated age related conditions, osteoarthritis, transient ischemic events, diabetic retinopathy, decreased insulin production due to inflammation initiated damage to pancreatic beta cells, HIV induced CVD, CVS and CAD secondary to ongoing periodic episodes of either sleep apnea and/or blood flow stagnation (e.g. sickle cell disease). Additional applications of the method include transfusions that include either RBC's or hemoglobin based oxygen carriers (HBOCs) and kidney dialysis.

The transdermal formulation can be administered to treat various local conditions associated endothelial dysfunction. For example, local conditions such as slow healing leg ulcers and erectile dysfunction are associated with underlying and often severe endothelial dysfunction which limits blood flow the damaged tissues. A method for treating slow healing leg ulcers includes sustained local delivery of nitric oxide to eliminate biofilms and infection that prevent therapeutic efficacy of agents that are designed to accelerate wound closure. In parallel transdermal delivery of an active agent such as curcumin will normalize the systemic vasculature thus promoting tissue oxygenation and allowing stem cell migration and development. The transdermal formulation can be administered in combination with an antibiotic agent or any suitable wound healing agent. For erectile dysfunction, the transdermal delivery of an agent such as curcumin can be used alone or in combination with topical nitric oxide and/or oral PD5 inhibitors to restore systemic vascular health and reduce systemic inflammation. Given that systemic NO booster (e.g. curcumin) enhances NO production in the endothelium and that oral supplementation with PD5 inhibitors extends the duration of action of NO, the combination of transdermally delivered active agent with oral PD5 inhibitors will accelerate recovery of the endothelium for patients with endothelial dysfunction including long covid and cytokine storm.

The transdermal formulation disclosed herein can also be administered to a subject in need thereof for decreasing ROS production, peroxynitrite production (via deactivation of iNOS activity) and/or increasing eNO production in the endothelium. Without being limited to any particular theory, it is postulated that the formulation provides pleiotropic effect of upregulation and/or activation of multiple anti-inflammatory and antioxidant enzymes and signaling pathways including for example Sirtuin 1 (SIRT1) and other inflammation modulating sirtuins, PPAR(gamma) (Peroxisome Proliferator Activated Receptor-Gamma), peroxisome proliferator-activated receptor-gamma coactivator (PGC)-1 alpha is a member of a family of transcription coactivators that plays a central role in the regulation of cellular energy metabolism. AMP-activated protein kinase (AMPK) is a phylogenetically conserved fuel-sensing enzyme that is present in all mammalian cells. When activated AMPK stimulates energy generating processes such as glucose uptake and fatty acid oxidation and decreases energy consuming processes such as protein and lipid synthesis. The transcription factor Nrf2 (nuclear factor erythroid 2-related factor 2), a major regulator of antioxidant and cellular protective genes, is primarily activated in response to oxidative stress. SIRT1/PGC-1α/PPAR-γ pathway, eNOS mediated enhancement of eNO production, PPARP's, Nrf2, Heme oxygenase, AMPK, and ACE2 (angiotensin-converting enzyme 2, or ACE2 "receptor," the protein provides the entry point for the coronavirus to hook into and infect a wide range of human cells. The formulation can also be applied to down regulation or inhibition of (toll like receptor 4 part of the triggering mechanism for inflammation) TLR4, NADPH oxidases (NADPH oxidase (nicotinamide adenine dinucleotide phosphate oxidase) is a membrane-bound enzyme complex that faces the extracellular space and generates reactive oxygen species), and ACE (ACE (Angiotensin I Converting Enzyme).

The transdermal formulation described herein can be applied to the treatment and management of acute pro-inflammatory insults as well as the chronic consequences of many pro-inflammatory conditions that can promote or relate to endothelial dysfunction (ED). Nonlimiting examples of diseases or conditions associated with endothelial dysfunction (ED) include cardiovascular disease, renal failure, cognitive decline, slow healing wounds, hypertension, stroke, microemboli, edema, sexual dysfunction, retinopathy, neuropathy, and neuropathic pain.

For acute diseases or conditions, the formulation is capable of rapidly initiating global anti-inflammatory and antioxidant activity to short circuit and limit the progression leading to the severe consequences of extreme ED. For example, a suitable patch or sponge loaded with the formulation provides extremely high concentration of NO stimulating agents such as curcumin and insert between the gums and cheeks for a to be determine time to insure rapid and sustained delivery of therapeutic levels of curcuminoids or other anti-inflammatory, anti-oxidant and NO stimulating agents. This safe approach eliminates concern over overdosing with NO directly and additionally activates the full repertoire of host based anti-inflammatory and antioxidant pathways. The use of transdermally delivered systemically or locally active agents such as curcuminoids can stimulate NO production in the vasculature and/or reducing the overproduction of reactive oxygen species (ROS). This combination of enhancing endothelial generated NO and shutting down ROS production is designed to prevent, limit and reverse ED and its consequences.

The transdermal formulation of this patent document can be administered to a subject in need thereof for treating diabetes and associated inflammation and other conditions. Inflammation in adipose tissue promotes insulin resistance and hyperglycemia, both of which cause and extend endothelial dysfunction. In addition, chronic untreated endothelial dysfunction generated and enhanced by hyperglycemia, excess ROS production and other diabetes associated factors is the common pathway through which type 2 diabetes and other pro-inflammatory triggers the end stage clinical symptoms including for example cardiovascular disease, renal failure, hypertension, stroke and microemboli, slow healing wounds, sexual and bladder dysfunction. neuropathic pain, and cognitive decline. By reducing blood glucose, reversing insulin resistance, reducing elevated blood glucose level or procedure-induced exaggerated and sustained rise in blood glucose, reducing levels of ROS, enhancing NO levels in the endothelium and restoring vascular homeostasis, the transdermal formulation of this patent document minimizes the negative and/or undesirable outcomes associated with surgery, transfusions, stent implants, dialysis and any other invasive procedure that can promote systemic inflammation. The formulation can upregulate Nrf2 and the associated antioxidant enzymes including the potent antioxidant heme oxygenase (HO-1) and reduces oxidative stress (thereby allowing for recovery of damaged endothelium, treating endothelial dysfunction and preventing the onset or the progression of endothelial dysfunction). Further, it limits the diabetes enhanced glucose response post-surgery and shortens the recovery time of the elevated glucose levels. Further, it can limit the extended and exaggerated stress-induced glucose spike in stressed (e.g. injuries, surgery and blood transfusion) diabetics, and the inflammatory consequences of the stress including urogenital dysfunction post prostatectomy.

The transdermal formulation can thus be administered to limit the negative clinical consequences associated with inflammation triggers in subjects with preexisting conditions or at risk of developing conditions that promote hyperglycemia and the ensuing endothelial dysfunction. In some embodiments, the formulation is administered prophylactically to a subject at risk of developing hyperglycemia. In some embodiments, the subject has been determined to have hyperglycemia.

In some embodiments, the amount/dosage of the active agent(s) are selected and/or the administration schedule are configures so that the method restores insulin sensitivity and/or reduces elevated blood glucose by at least about 5%, at least about 10%, at least about 15%, at least about 20%, at least about 30%, at least about 40%, at least about 50%, or at least about 60% in comparison with a control (without treatment with the transdermal formulation) or the level prior to the treatment with the transdermal formulation disclosed herein. In some embodiments, the subject has been diagnosed to have diabetes (e.g. type 2 diabetes), undergone invasive procedures such as surgery, blood transfusion, stent implants, and dialysis, or suffered injury. In some embodiments, the subject prior to the treatment has an abnormal level of blood glucose, wherein the abnormal level is higher or lower than a normal level or the level of a healthy subject by at least about 5%, at least about 10%, at least about 15%, at least about 20%, at least about 30%, at least about 40%, at least about 50%, at least about 60%, at least 80% or at least 100%.

The transdermal formulations disclosed herein are capable of reducing the level of pro-inflammatory cytokines. In some embodiments of the methods disclosed herein, the amount/dosage of the active agent(s) are selected and/or the administration schedule are configures so that one or more of biomarkers are reduced or modified by at least about 5%, at least about 10%, at least about 15%, at least about 20%, at least about 30%, at least about 40%, at least about 50%, at least about 60% or at least about 100% in comparison with a control or the level prior to the treatment with the transdermal formulation. Nonlimiting examples of the markers that can be reduced or modified by the transdermal formulations disclosed herein include TNF-α, TGFβ, MCP-1, IL-1α, IL-1β, IL-6, IL-10, IL-1, IL-18, MIF, TNF-β, MMP9, HIF-1, GLUT1, Hemox, PDK1, VEGF, CD11, EMR1, CXCR4, CCR5, IL-8, receptor for advanced glycation end products (RAGE), hsCRP, Total Antioxidant Capacity (TAC), Prostaglandins, leukotrienes, substance P, Phosphatidylserine surface presentation on RBCs, Selectins, laminins and Cahedrins, Immunoglobulin receptors, chondroitin sulfate, syndecan-1, IL-1a/b, TNF-α, IL-6, D-dimer and other markers that reflect propensity to abnormal blood clotting, emboli formation, thrombosis, C-reactive protein (CRP), Nrf2, NFkappa B, glutathione peroxidase (GPx), superoxide dismutase (SOD), Syndecan-1, HMW-hyaluronic acid (1,000-6,000 kDa), A disintegrin and metalloprotease with thrombospondin type 1 repeats-13, Protein C, Von Willebrand factor, Chondroitin sulfate, and sP-selectin. Additional examples include markers associated with blood pressure, vasodilation, lood flow dynamics, vascular leakage/edema, M1/M2 Macrophage polarization, Soluble platelet selectin, Heparan sulfate, and cell and tissue oxygenation. In some embodiments, the subject prior to the treatment has an abnormal level of one or more biomarkers or pro-inflammatory cytokines, wherein the abnormal level of the biomarkers or one or more cytokines is higher or lower than a normal level or the level of a healthy subject by at least about 5%, at least about 10%, at least about 15%, at least about 20%, at least about 30%, at least about 40%, at least about 50%, at least about 60% or at least about 100%.

In some embodiments of the methods disclosed herein, the subject has been diagnosed as having a disease or condition selected from the group consisting of aging, chronic and acute inflammatory condition, chemically induced vascular and/or pulmonary inflammation, viral infection, bacterial infection, and fungal infection.

Further examples of disease or condition that can be treated with methods disclosed herein include neurodegenerative disease, diabetic kidney disease, diabetes, cardiovascular disease, endothelial dysfunction, muscular dystrophy, pain, neuroinflammatory condition, abnormal vascular homeostasis, lupus, Parkinson's disease, Alzheimer's disease, Huntington's disease, amyotrophic lateral sclerosis, neurodegenerative consequences of traumatic brain injury or cerebral hemorrhage, hypertension, inflammation, osteoarthritis, rheumatoid arthritis, endothelial dysfunction, dermatological condition, ophthalmological condition, bacterial infection, viral infection, ischemia reperfusion injury, hypoxia reoxygenation injury, cytokine storm phenomena, cerebral malaria, Chagas disease, hemoglobinopathies, type 2 diabetes, coronavirus, skin/dermatological conditions, acne, inflammatory skin conditions, Raynaud's disease, post herpetic lesions, shingles, skin infections, wounds, burns, leg ulcers, sickle cell, diabetic, onychomycosis, peripheral vascular disease, infected and/or inflamed mucosal tissues, erectile dysfunction, female sexual dysfunction, vaginal infections/inflammation, catheter associated urinary tract infection, sinusitis, cystic fibrosis, acute respiratory distress syndrome, pulmonary fibrosis, chronic obstructive pulmonary disease (COPD), bronchiectasis, pulmonary infections including tuberculosis, pulmonary hypertension, and burns and other open wounds, inner ear infection, outer ear infection, gastric and intestinal diseases, and acute vascular inflammatory conditions. Further examples of diseases treatable with methods described herein include infectious disease is selected from the group consisting of Coronaviruses (including SARS-CoV-2), Ebola, Dengue fever, hemorrhagic shock, endotoxic shock, acellular hemoglobin toxicity due to hemolysis and/or the use of acellular hemoglobin based blood substitutes (HBOC's), Rift valley fever, Marburg, Crimean-Congo hemorrhagic fever (CCHF), South American hemorrhagic fever, dengue, yellow fever, Omsk hemorrhagic fever virus, Kyasanur Forest, Junin, Machupo, Sabia, Guanarito, Garissa, Ilesha, and Lassa fever viruses.

Further examples of diseases or conditions treatable with the formulations disclosed herein include neurodegenerative diseases or disorders (e.g. Alzheimer's disease (AD), Huntington's disease, Parkinson's disease, amyotrophic lateral sclerosis (ALS), multiple sclerosis and disorders caused by polyglutamine aggregation); skeletal muscle disease (e.g. Duchenne muscular dystrophy, skeletal muscle atrophy, Becker muscular dystrophy or myotonic Dystrophy); metabolic disorders (e.g. insulin resistance, diabetes, obesity, impaired glucose tolerance, high blood cholesterol, hyperglycemia, dyslipidemia and hyperlipidemia); adult-onset diabetes, diabetic nephropathy, neuropathy (e.g. sensory neuropathy, autonomic neuropathy, motor neuropathy, retinopathy); bone disease (e.g. osteoporosis), blood disease (e.g. leukemia); liver disease (e.g. due to alcohol abuse or hepatitis); Obesity; bone resorption, macular degeneration aging, AIDS-related dementia, ALS, Bell's palsy, atherosclerosis, heart disease (for example, arrhythmia, chronic congestive heart failure, ischemic stroke, coronary artery disease and cardiomyopathy), Chronic degenerative disease (e.g., myocardial disease), chronic renal failure, type 2 diabetes, ulcer, cataract, presbyopia, glomerulonephritis, Guillain-Barre syndrome, hemorrhagic stroke, rheumatoid arthritis, inflammatory bowel disease, SLE, Crohn's disease, Diseases or disorders associated with osteoarthritis, osteoporosis, chronic obstructive pulmonary disease (COPD), pneumonia, skin aging, urinary incontinence, mitochondrial dysfunction (e.g. mitochondrial myopathy, encephalopathy, Leber's disease, Lee encephalopathy, Pearson Disease, lactate acidosis, "mitochondrial encephalopathy, lactate acidosis and stroke-like symptoms" (MELAS), muscular diseases, including neuromuscular diseases, such as muscular dystrophy and myopathy, and diseases or disorders associated with neuronal death, aging, or other conditions characterized by unwanted cell loss. In some embodiments, the disease or condition is selected from Parkinson's disease, Alzheimer's disease, Huntington's disease, amyotrophic lateral sclerosis, and neurodegenerative consequences of traumatic brain injury or cerebral hemorrhage, sickle cell disease (including pain associated with sickle cell disease), thalassemias (e.g. HbE/beta Thalassemia), diabetic retinopathies, glaucoma, dry eye syndrome, and inflammation triggered by surgery, aging, chronic and acute inflammatory condition, chemically induced vascular and/or pulmonary inflammation, viral infection, bacterial infection, fungal infection, diabetic kidney disease, diabetes, cardiovascular disease, endothelial dysfunction, muscular dystrophy, pain, neuroinflammatory condition, abnormal vascular homeostasis, lupus, retinopathies including diabetic retinopathy, macular degeneration, peripheral vascular disease, long term systemic consequences of chemo and radiation therapy, brain fog, rheumatoid arthritis, soft tissue injuries (muscle, tendons and ligaments), surgery induced inflammatory sequelae (urogenital dysfunction), transfusion induced inflammation, inhibition of stent restenosis, limit inflammatory consequences of dialysis, post dental procedure inflammation and pain, neuropathic pain from any proinflammatory insult including peripheral neuropathy, spinal neuropathy, arthritic pain, cognitive dysfunction in children due to cerebral vascular damage due to sickle cell disease, cytokine storm due to corona virus, dengue fever, Ebola, rift valley fever and influenza, cerebral malaria, metastatic spread of tumors via dysfunctional blood vessels, systemic consequences of psoriasis, dementias including Alzheimer's disease and Pick's disease, post traumatic brain injury and hemorrhagic shock.

Autoimmune and immune related disorders and diseases can also be treated or prevented with methods described herein. Exemplary autoimmune diseases and immune related disorder include systemic lupus erythematosis, rheumatoid arthritis, osteoarthritis, juvenile chronic arthritis, a spondyloarthropathy, systemic sclerosis, an idiopathic inflammatory myopathy, Sjogren's syndrome, systemic vasculitis, sarcoidosis, autoimmune hemolytic anemia, autoimmune thrombocytopenia, thyroiditis, diabetes mellitus, immune-mediated renal disease, a demyelinating disease of the central or peripheral nervous system, idiopathic demyelinating polyneuropathy, Guillain-Barr syndrome, a chronic inflammatory demyelinating polyneuropathy, a hepatobiliary disease, infectious or autoimmune chronic active hepatitis, primary biliary cirrhosis, granulomatous hepatitis, sclerosing cholangitis, inflammatory bowel disease, gluten-sensitive enteropathy, Whipple's disease, an autoimmune or immune-mediated skin disease, a bullous skin disease, erythema multiforme, contact dermatitis, psoriasis, an allergic disease, asthma, allergic rhinitis, atopic dermatitis, food hypersensitivity, urticaria, an immunologic disease of the lung, eosinophilic pneumonias, idiopathic pulmonary fibrosis, hypersensitivity pneumonitis, systemic lupus erythematosus, scleroderma, and arthritis.

Non-limiting examples of neurological diseases that can be treated or the progression of which can be limited with methods of this patent document include neurodegenerative disorders include stroke, Alzheimer's disease (AD), Parkinson's disease (PD), Huntington's disease (HD), amyotrophic lateral sclerosis (ALS; Lou Gehrig's disease), diffuse Lewy body disease, chorea-acanthocytosis, primary lateral sclerosis, Multiple Sclerosis (MS), and Friedreich's ataxia, Periventricular leukomalacia (PVL), ALS-Parkinson's-Dementia complex of Guam, Wilson's disease, cerebral palsy, progressive supranuclear palsy (Steel-Richardson syndrome), bulbar and pseudobulbar palsy, diabetic retinopathy, multi-infarct dementia, macular degeneration, Pick's disease, diffuse Lewy body disease, prion diseases such as Creutzfeldt-Jakob, Gerstmann-Straussler-Scheinker disease, Kuru and fatal familial insomnia, primary lateral sclerosis, degenerative ataxias, Machado-Joseph disease/spinocerebellar ataxia type 3 and olivopontocerebellar degenerations, spinal and spinobulbar muscular atrophy (Kennedy's disease), familial spastic paraplegia, Wohlfart-Kugelberg-Welander disease, Tay-Sach's disease, multisystem degeneration (Shy-Drager syndrome), Gilles De La Tourette's disease, familial dysautonomia (Riley-Day syndrome), Kugelberg-Welander disease, subacute sclerosing panencephalitis, Werdnig-Hoffmann disease, synucleinopathies (including multiple system atrophy), Sandhoff disease, cortical basal degeneration, spastic paraparesis, primary progressive aphasia, progressive multifocal leukoencephalopathy, striatonigral degeneration, familial spastic disease, chronic epileptic conditions associated with neurodegeneration, Binswanger's disease, and dementia (including all underlying etiologies of dementia).

Insulin resistance disorders treatable with methods of this patent document include any disease or condition that is caused by or contributed to by insulin resistance. Examples include: diabetes, obesity, metabolic syndrome, insulin-resistance syndromes, syndrome X, insulin resistance, high blood pressure, hypertension, high blood cholesterol, dyslipidemia, hyperlipidemia, dyslipidemia, atherosclerotic disease including stroke, coronary artery disease or myocardial infarction, hyperglycemia, hyperinsulinemia and/or hyperproinsulinemia, impaired glucose tolerance, delayed insulin release, diabetic complications, including coronary heart disease, angina pectoris, congestive heart failure, stroke, cognitive functions in dementia, retinopathy, peripheral neuropathy, nephropathy, glomerulonephritis, glomerulosclerosis, nephrotic syndrome, hypertensive nephrosclerosis some types of cancer (such as endometrial, breast, prostate, and colon), complications of pregnancy, poor female reproductive health (such as menstrual irregularities, infertility, irregular ovulation, polycystic ovarian syndrome (PCOS)), lipodystrophy, cholesterol related disorders, such as gallstones, cholecystitis and cholelithiasis, gout, obstructive sleep apnea and respiratory problems, osteoarthritis, and prevention and treatment of bone loss, e.g. osteoporosis. Further application of methods of this patent document include promoting wound healing such as can also be used to promote wound healing and diabetes-impaired wound healing.

In some embodiments of any method disclosed herein, there also includes a step of determining a subject as having downregulated or dysfunctional SIRT1 in comparison with a normal standard or reference. In some embodiments, the methods disclosed herein further include, prior to administering to the subject the transdermal formulation, diagnosing the subject as having endothelial dysfunction or a disease or condition associated with endothelial dysfunction.

In some embodiments of the methods disclosed herein, there is included a step of determining the subject as having a systemic NO level or plasma nitrite and/or nitrate level lower than a normal level or a standard of heathy references by at least 5%, at least 10%, at least 15%, at least 20%, at least 25%, at least 30%, at least 40%, at least 50%, or at least 60%.

In any of the methods disclosed herein, the treatment regimen can be administered after a symptom is observed clinically or a clinical manifestation of a disease or condition has taken place. Alternatively, the method can be used prophylactically before the onset or observation of any clinical symptom. For instance, the methods disclosed herein are capable of addressing pro-inflammatory insults including acute inflammatory insults triggered by certain viral infection (e.g. SARS CoV2, Dengue fever, and influenza), obesity and glucose induced inflammatory triggers, and inflammation triggered by exposure to toxic metals and chemicals. The treatment can be administered when a symptom has been identified or prior to the onset or observation of any symptom. In further examples, the transdermal formulation can be administered prophylactically to prevent inflammatory consequences of surgery including post surgical inflammation induced pain or erectile dysfunction.

The methods disclosed herein can increase NO level systemically or locally. In some embodiments of any transdermal formulation or method of this patent document, the amounts of active ingredients in the transdermal formulation (e.g. the NO booster and/or the NO precursor, the polyol, the optional fatty acid, and/or other components) are selected so that it increases a subject's systemic or local NO level or plasma nitrite and/or nitrate level by at least 5%, at least 10%, at least 15%, at least 20%, at least 25%, at least 30%, at least 40%, at least 50%, at least 60% or more in comparison with a control or the NO level or plasma nitrite and/or nitrate level prior to administering the formulation. In some embodiments, the desired increase or change can be achieved within about 1 hour, within about 2 hours, within about 3 hours, within about 5 hours, or within about 8 hours. In some embodiments, the increase or change can be maintained for a period of about 1 day, about 3 days, about 5 days, about 7 days, about 10 days, about 15 days, about 30 days or more. Various methods can be used for measuring the NO level or plasma nitrite and/or nitrate level, including for example the colorimetric method using the Griess reagent and the chemiluminescence method.

In some embodiments of any transdermal formulation or method of this patent document, the amounts of the active ingredients in the transdermal formulation (e.g. the NO booster and/or the NO precursor, the polyol, the optional fatty acid, and/or other components) are selected so that the systolic pressure and/or diastolic pressure and/or mean arterial pressure of the subject is reduced by at least 2, at least 4, at least 6, at least 8, at least 10, at least 12, at least 14, about 18, at least 20, at least 25, at least 30, at least 35, at least 40 or more mm Hg over the above period of 1, 2, 3, 4, 5, 6, 7, 8, 9, 10 or more days in comparison with a control or the NO level or plasma nitrite and/or nitrate level prior to administering the formulation.

In some embodiments of any method disclosed herein, the subject has been diagnosed to have hypertension or is at risk of developing hypertension. The transdermal formulation disclosed herein can be administered once, twice, three time or as needed over a period of 1, 2, 3, 4, 5, 6, 7, 8, 9, 10 or more days. In some embodiments, the formulation in the form of for example a patch, cream, or gel is administered once every 1, 3, 5, 7, or 10 days.

Another aspect of this disclosure provides a method of reducing CD38 activity or reducing an elevated CD level, comprising contacting the transdermal formulation disclosed herein with a cell overexpressing CD38. The desirable effect is best achieved via a combination of macrophage/monocyte/microglia repolarization from an M1 to an M2 phenotype, reduction of senescence cell population and anti-inflammatory/antioxidant activity. In some embodiments, the CD38 is in a cell (on the surface of a cell or within a cell). In some embodiments, the contacting occurs in vitro. In some embodiments, the contacting occurs in vivo.

Another aspect of this disclosure provides a method of incorporating an agent into a cell by contacting the cell with the formulation disclosed herein. As a result of enhanced NO level, the method can stabilize the cells, improve storage properties and reverse storage lesions. In some embodiments, the cells are red blood cells. In some embodiments, the formulation is in a liquid form. In some embodiments, the formulation includes S-nitrosothiol-containing molecule.

A related aspect provides a method for prolonging or and enhancing the ex vivo viability of a biological material (e.g. cells, tissue, organ, body fluid sample or blood). The method includes contacting (e.g. rinsing, mixing, perfusing, irrigating, and/or infusing) the biological material with a formulation disclosed herein. The scope and amount of the solvent, the curcuminoid, the optional flavonoid and other components of the formulation are as disclosed above.

Besides mixing or contacting the biological material ex vivo with the formulation disclosed herein, the formulation (with adjustment in concentration and form) may be administered (e.g. transdermally) to the donor subject prior to the harvest of the cells, tissues, organs, or blood (either while the subject is still alive, or alternatively, postmortem). In some embodiments, the disclosed formulation is used as a wash solution to cleanse the freshly-recovered biological material from the donor subject prior to long-term storage, transport, or transplantation. In some embodiments, the formulation is a solution comprising an effective amount of a curcuminoid. In some embodiments, the method is directed to prolonging the viability of red blood cells ex vivo by mixing or contacting the red blood cells with the solution.

In the practice of the present invention, it is often desirable to maintain the cells, tissues, or organs in the composition essentially from a time immediately post-harvest until the explant material is readied for transplantation into a recipient subject. During the interval between harvest and implantation or transfusion, it is also desirable to monitor and control the environmental conditions, and storage parameters to maintain the integrity, viability, and biochemical activity of the recovered biological material.

During storage, red blood cells (RBCs) undergo several biochemical and biomechanical changes that reduce RBCs's survival and compromise the oxygen transporting function of blood. These changes are collectively referred to as the storage lesion, which is often characterized in terms of increased inflammation, hemolysis, microparticle formation, and/or shorter circulation time. Storage lesion may contribute to reduced RBCs' survival and compromised oxygen transporting function of blood. The solution formulation disclosed herein is capable of slowing the onset of storage lesion phenomena in the RBC and/or slowing the progression in changes associated with storage lesion. In comparison with a control or untreated reference sample (collected at the same time and/or from the same source as the target sample except being untreated with the formulation disclosed herein) over the same period of time, the target sample treated with the formulation is characterized by one or more of decreased inflammation, hemolysis, and microparticle formation, and increase circulation time, independently by at least 2%, at least 5%, at least 8%, at least 10%, at least 15%, at least 20%, at least 25%, at least 30%, at least 40%, at least 50%, at least 60%, at least 70%, at least 80%, at least 90%, at least 100%, at least 120%, at least 150%, at least 200%, or any range between any two of the aforementioned percentage values. In some embodiments, the biological material (e.g. blood sample) and the formulation or solution are in a ratio ranging from about 10,000:1 to about 5:1, from about 10,000:1 to about 50:1, from about 10,000:1 to about 500:1, from about 10,000:1 to about 1000:1, from about 8,000:1 to about 500:1, or from about 5,000:1 to about 500:1 by weight. Nonlimiting examples of the ratio by weight between the biological material (e.g. blood sample) and the formulation or solution include about 10,000:1, about 5,000:1, about 2,000:1, about 1,000:1, about 500:1, about 400:1, about 300:1, about 200:1, about 100:1, about 80:1, about 50:1, about 10:1, and any range between any two of the aforementioned values.

The solution formulation is capable of stabilizing red blood cells, preventing hemolysis of unstable red blood cells and generating circulating red blood cells that show biochemical and biophysical evidence of being stabilized. Accordingly, red blood cells treated with the formulation exhibits significantly slowed or reduced the oxidative damage that limits both shelf life and efficacy of red blood cells.

In some embodiments, the agent(s), the solvent and their amounts are selected so that more than 40% of the biological material (e.g. red blood cells) remain substantially viable for the period of at least about 24 hours. In some embodiments, at least 50%, at least 60%, at least 80%, at least 90%, at least 95%, or at least 99% of the red blood cells remain viable for at least 1 day, at least two days, at least three days, at least five days, at least seven days, at least ten days, at least twenty days, at least thirty days, at least forty-five days, at least two months, at least three months, at least four months, or at least six months.

In any embodiment disclosed herein, the viability of cells, tissues, or organs can be determined by assays that are known to those of skill in the relevant art. For example, the viability of cells is readily determined by using a microscopic assay that is commonly referred to in the art as a "live/dead assay". In one such assay, the biologic dyes 5-chloromethylfluorescein diacetate and propidium iodide (which differentially stain living and non-living cells) are employed and evaluated by a microscopy-based assay. Such dyes are typically fluorescent, and the fluorescence may be detected and used to produce dual-parameter fluorescence histograms, most typically using fluoromicroscopic techniques to distinguish the living vs. the non-living cells, in which the living and non-living cells each fluoresce at distinctly-different wavelengths.

In some embodiments, to determine the % viability of cells or tissues that have been stored as a function of time, a biological sample may be initially assayed for viability (typically within 10 minutes, within 30 minutes, within 1 hour, within 2 hours, within 4 hours, within 8 hours, within 12 hours, within 24 hours, within 48, or within 72 hours of harvest from the donor subject) to determine an "initial viability." Subsequent viability determinations are then made on the tissue over a period of time to determine "current viability." The % viability can therefore be determined at any time post-harvest using the following equation:

$$[(\text{current viability})/(\text{initial viability})] \times 100 = \text{Percent viability}$$

If desired, multiple samples may be analyzed and averaged both at initial assay, and/or during subsequent analyses to determine an "average viability" of the recovered tissue. Alternatively, the determination of tissue, cell, or organ viability may also include one or more biochemical or anatomical assays that are known in the art, and which provide qualitative and/or quantitation evidence of the biological activity or functionality of the explanted tissue once it is introduced into the recipient animal. Additional assays and detection methods are provided in U.S. Pat. No. 9,737,071, the entire disclosure of which is hereby incorporated by reference.

In some embodiments, the treatment (e.g. mixing or contacting as described above) of blood (freshly collected or aged) with the formulation disclosed herein allows for the transport and delivery of therapeutics (e.g. curcuminoid) loaded to red blood cells. With the red blood cells serving as a stealth pharmacological vehicle, therapeutics such as agent can be delivered to a subject in need via transfusion and restore or improve important parameters such as microvascular blood flow, permeability, glycocalyx, and oxygenation. The blood can be treated prior to transfusion by, for example, about 1 hour, about 2 hours, about 4 hours, about 6 hours, about 8 hours, about 10 hours, about 15 hours, about 24 hours, about 48 hours, about 3 days, about 4 days, about 6 days, or any range between the aforementioned values. The treatment can be performed at one or more time points (once or multiple times) prior to transfusion. The blood sample prepared from blood treatment approach can thus be applied to the treatment of various diseases and conditions.

In any embodiments disclosed herein, the components and their amounts of the formulation are configured so that the formulation can decrease or increase a parameter or biomarker, in reference to a control or untreated sample, by at least 2%, at least 5%, at least 8%, at least 10%, at least 15%, at least 20%, at least 25%, at least 30%, at least 40%, at least 50%, at least 60%, at least 70%, at least 80%, or any range between any two of the aforementioned percentage values.

In some embodiments, the method includes adding to the biological material (e.g. blood sample) one or more additional components such as stabilizer, antibacterial agent and anti-inflammatory agent. The additional components may also be dissolved in the formulation solution before mixing with the blood. In some embodiments, the additional component is myristic acid and other medium sized fatty acids that have potential health.

In some embodiments, the biological sample is stored at a temperature ranging from about −30° C. to about 37° C. nonlimiting examples of the temperature include about −30° C., about −20° C., about −10° C., about −5° C., about 0° C., about 5° C., about 10° C., about 15° C., about 20° C., about 25° C., and any range between any two of the aforementioned temperatures.

In some embodiments, the blood is collected from a healthy individual. In some embodiments, the blood is collected from an individual and after being treating with the formulation described herein and other necessary medical procedures is reinjected to the individual.

In some embodiments, the solution, prior to or after mixing with the blood, has a pH ranging from about 5.5 to about 7.0.

In some embodiments, the method includes depleting oxygen and/or carbon dioxide in the sample.

In some embodiments, the agent(s), the solvent and their amounts are selected so that adenosine triphosphate (ATP) and/or 2,3-diphosphoglycerate (2,3-DPG) levels reduces by less than 10%, less than 20%, less than 30%, less than 40%, less than 50%, less than 60%, or less than 80% in a period of 1, 2, 4, 6, 8, 10, 14, or 20 days in comparison with a control or an untreated sample.

In some embodiments, the concentration of the curcuminoid in the solution prior to mixing with the sample ranges from about 1.0 to about 500, from about 1.0 to about 350, from about 1.0 to about 200, from about 5.0 to about 300. from about 10 to about 300. from about 20 to about 300, from about 50 to about 200, from about 100 to about 200 µg/mL. Nonlimiting examples of the concentration of the curcuminoid in the solution include about 1.0, about 2.0, about 5.0, about 10, about 20, about 50, about 100, about 150, about 200, about 250, about 300, about 350, about 400, about 500 µg/mL, and any range between any two of the aforementioned values. In some embodiments, the concentration of the curcuminoid in the solution prior to mixing with the sample ranges from about 0.05 to about 30, from about 0.1 to about 10, from about 0.1 to about 5, from about 0.1 to about 1, from about 0.5 to about 1 mM, and nonlimiting examples of the concentration include about 0.1, about 0.2, about 0.5, about 0.6, about 0.8, about 1.0, about 1.5, about 2.0, about 3.0, about 5.0, about 8.0. about 10.0, about 15 mM and any range of any two of the aforementioned values. In some embodiments, the concentration of the curcuminoid in the blood sample ranges from about 0.2 to about 20, from about 0.5 to about 10, from about 1 to about 10, or from about 1 to about 5 mM in the sample. Nonlimiting examples of the concentration of the curcuminoid in the blood sample include a about 0.1, about 0.2, about 0.5, about 0.6, about 0.8, about 1.0, about 1.5, about 2.0, about 3.0, about 5.0, about 8.0. about 10.0, about 15 mM and any range of any two of the aforementioned values.

Treatment of cells (e.g. red blood cells) with the formulation described herein can delivery NO booster (e.g. curcumin) and optionally other antiinflammatory/antioxidant agents into the lipid membrane or beyond cytosol should stabilize the cells for storage, and convert the transfused cells into long lasting (circulating) anti-inflammatory agents that can slowly deliver these agents to endothelial linings in the capillaries and other small diameter vessels. Similarly, treatment of the cells with a formulation containing high concentrations of a NO precursor such as lipophilic S-nitrosothiol and the S-NO derivative of alkyl ester derivatives of NAC should be effective in transnitrosating thiols in and on the cells. Nitrosation of key thiols on and in the red blood cells (including beta 93 on Hb and the thiols of the Band 3 protein) has been shown to stabilize red blood cells against oxidative damage, microparticle formation and hemolysis. Such red blood cells can thus be used as a vehicle to deliver NO to thiols on the endothelium as well.

Another aspect provides a method of transfusing blood to a subject in need thereof. The method includes transfusing the blood sample disclosed herein, which is stored in a container or a kit as described above. The blood sample can be prepared in the same way as in the method disclosed herein for prolonging the viability of red blood cells ex vivo. Curcumin loaded red blood cells are ideally suited to deliver curcumin to capillary beds and smaller vessels such as the arterioles. Those are the appropriate sites for treating for example numerous vascular disorders stemming from endothelial dysfunction including for example ischemia/reperfusion injury and vaso-occlusive crises. A related aspect provides a method of treating diseases or conditions associated with endothelial dysfunction. The method includes administering to a subject in need thereof an effective amount of the blood sample disclosed herein. Because the red blood cells serve as a vehicle for an active agent (e.g. curcumin, other curcuminoid or flavonoid), therapeutic effect can be achieved when the agent is delivered to suitable sites including for example narrow blood vessels such as arterioles and capillary beds where curcumin could be released/repartitioned into the endothelial lining of the blood vessels due to the close proximity of the RBC's to vessel lining Release of curcumin would reduce or eliminate endothelial dysfunction and restore NO production from within the endothelium which is needed for normal function of the endothelium. Nonlimiting examples of diseases or conditions associated with endothelial dysfunction include those disclosed above in this patent document.

In some embodiments of any method disclosed herein, the active agent (e.g. curcuminoid or flavonoid) is loading into red blood cells and leucocytes (white blood cells) such as macrophages, monocytes, microglia and neutrophils. Uptake of curcuminoids and/or flavonoids by activated pro-inflammatory white blood cells may account for the rapid reversal of cytokine storm type phenomena in for example acute inflammation disease or conditions under the treatment methods disclosed herein.

Another aspect relating to the blood sample disclosed herein is a method of preserving or restoring microcirculation, or reducing or reversing the microcirculatory consequences of diseases or conditions (e.g. hemorrhagic shock) by administering to a subject in need thereof the blood sample. The blood sample can be treated with the formulation disclosed herein prior to transfusion (e.g. 1, 2, 3, 4, 6, or 8 hours before transfusion).

In some embodiments, the method is applicable for treating or preventing hemorrhagic shock (HS). Traumatic hemorrhage leads to HS. HS is a major cause of death in both civilian and military settings, accounting for one-third of all deaths from trauma, and 80% of potentially survivable battlefield injuries. Almost 50% of deaths due to hemorrhage occur within 3 to 6 h of injury. Studies performed in various species and models unequivocally established that the microvasculature is critical in the pathophysiology of HS and is linked to organ damage due to decreased tissue perfusion and oxygenation as well as damage from excess production of reactive oxygen species (ROS). The potent inflammatory response, associated with HS, results in decreased tissue perfusion, upregulation of interleukins/cytokines, microvascular endothelium and neutrophil activation, ROS generation, and increased permeability that is also caused by glycocalyx degradation. HS/trauma disrupts the balance between microvasculature and multiple blood components, sometimes leading to coagulopathy which also contributes to HS associated morbidity and mortality. The preservation and restoration of the microcirculation is involved in all therapeutic attempts to reverse or minimize the adverse consequences of HS. The blood sample disclosed herein can thus be transfused to deliver therapeutics that can improve Hemorrhagic Shock outcomes. Aged RBCs might be repurposed to treat combat casualties vulnerable to or suffering from HS. The ability to use RBCs, including aged/stored RBCs, as therapeutic agents effective in treating the underlying causative mechanisms driving HS represents a substantial advance for combat care treatment. In some embodiments, transfusion of the blood sample restores or improves one or more of important parameters such as microvascular blood flow, permeability, glycocalyx, and oxygenation.

A related aspect provides a method of enhancing tissue perfusion in a subject in need thereof by administering or transfusing to the subject the blood sample treated with the formulation disclosed herein, or administering to the subject (prior to or during blood transfusion) the transdermal formulation disclosed herein. Sufficient tissue perfusion and oxygenation are vital for all metabolic processes in cells and the major influencing factor of tissue repair and resistance to infectious organisms. Tissue perfusion has been aliked with blood flow, oxygen delivery or a combination of flow and nutritional supply including that of oxygen. The enhanced tissue perfusion can be determined by measuring levels of biomarkers including for example serum lactate, central venous oxygen saturation, reticulocytosis, lactate dehydrogenase, unconjugated bilirubin, haptoglobin, hematocrit, cellular adhesion molecules (CAMs), E-selectin, intercellular adhesion molecule 1 (ICAM-1), vascular cell adhesion molecule 1 (VCAM-1), syndecan-1. These biomarkers can be measure as a function of time after/or before and after transfusion. Biomarkers for untreated blood sample can also be collected as a reference to show the improved profile for the blood sample treated with the formulation disclosed herein. Monitoring of peripheral circulation also allows for evaluation in changes of tissue perfusion. Well known approaches such as near-infrared spectroscopy (NIRS) oximetry can be used for detection purposes.

In some embodiments, the amount of the curcuminoid in the formulation or in the treated blood sample is selected such that, in reference to a control or untreated sample (collected at the same time and/or from the same source), tissue perfusion is enhanced and/or one or more of the aforementioned biomarkers are increased or decreased by at least 2%, at least 5%, at least 8%, at least 10%, at least 15%, at least 20%, at least 25%, at least 30%, at least 40%, at least 50%, at least 60%, at least 70%, at least 80%, or any range between any two of the aforementioned percentage values.

Another aspect provides a method of improving the safety and/or efficacy of transfusion by, prior to, during or shortly after the transfusion procedure, administering to a subject in need thereof a transdermal formulation disclosed herein, transfusing to a subject the blood sample disclosed herein, or contacting the cells or fluid to be transfused with the formulation disclosed herein. For instance, the formulation containing NO booster or NO precursor can be administered transdermally (e.g. in a patch or a paste) to a subject prior to, during, or shortly after blood transfusion to protect the red blood cells and enhance the therapeutic effect. In some embodiments, the method includes administering the transdermal formulation to the subject or contacting the formulation with cells or fluid 10 minutes, 15 minutes, 30 minutes, 1 hour, 2 hours, or more than 4 hours before the transfusion takes place. In some embodiments, the method is directed to transfusion of the blood sample disclosed herein.

When directly contacting the cells or fluid ex vivo (e.g. a blood sample disclosed herein), the formulation enhances the viability of for example red blood cells and/or loads the therapeutic agent (e.g. curcuminoid) to the cells so that subsequent transfusion to a subject achieves better efficacy and safety. In some embodiments, the blood sample disclosed herein is transfused to a subject who is administered, prior to, during or after transfusion, a transdermal formulation disclosed herein.

A related aspect provides a method of delivering an active agent transdermally to a subject in need thereof. The method includes administering to the subject a transdermal formulation or the blood sample disclosed herein. By delivering an effective amount of the active agent locally or systemically, a rapid and extended therapeutic effect can be achieved. The scope of the target diseases or conditions is as described above. In some embodiments, the transdermal formulation includes, as an active agent or ingredient for treating the disease or condition, one or more curcuminoids and optionally one or more of polyphenol, flavonoid, stilbenoid, secosteroid, or natural products that promote NO production. In some embodiments, the transdermal formulation includes one or both of curcumin and quercetin, and optionally one or more of one or more of polyphenol, flavonoid, stilbenoid, and secosteroid. As a result, red blood cells, apart from its essential physiological oxygen delivery role in the body, may also act as a natural biological pharmacodynamic vehicle (e.g., release of curcumin in the vasculature) that is able to evade the normal mechanisms for elimination of drugs from the circulation. This finding has paradigm changing potential for drug delivery.

In any embodiment of the above described methods, the formulation of this patent document can be added to the blood sample at any suitable interval to slow the onset of storage lesion phenomena or achieve other desirable results (e.g. less inflammation, less hemolysis, less microparticle formation, or longer circulation time in comparison with a control or an untreated sample). For instance, after treatment of a blood sample on day 1, one, two, three, four or more treatment or additions of the formulation can be made. Each of the intervals between two successive treatments/additions independently is 1, 2, 4, 7, 8, 10, 14, 20, 25, or 30 days. In some embodiments, the formulation is administered on a single dose protocol including, for example, single dosing just on day one of storage and single dosing on any intermediate day between day 1 and day X (e.g. day 10, 20, 30, 40 or 50) inclusive of day X (or any to be determined final day of storage). In some embodiments, the formulation is administered on a multiple dosing schedule, including for example, sequential dosing starting at any time point during the storage process with the interval between dosing ranging from every 7 days, 14 days, 21 days, 28 days with the start date ranging from day 1 to any intermediate time point. Dosing on the last day of storage is also an option independent of the interval protocol.

Various means can be used for the delivery of the formulation. In some embodiments, a storage bag can be filled with the formulation disclosed herein for day 1 or day X single dose protocol. In some embodiments, the formulation is delivered into the storage bag via a syringe injecting into an injection port on the bag. In some embodiments, the formulation is delivered directly into the bag as needed. In some embodiments, a prefilled frangible pouch is incorporated into the wall of the storage bag that can be "popped" using finger pressure and thereby release the dose of the formulation.

Method of Manufacturing

Another aspect of the present disclosure provides a method of manufacturing the formulation or the blood sample disclosed herein. The method includes for example preparing a solution of the polyol solvent and the optional fatty acid permeation enhancer or additive, followed by addition of the agent (NO booster or NO precursor). If necessary, the solution can be heated to a suitable temperature to dissolve fatty acid and/or the agent. In some embodiments, the active agent (e.g. NO booster or NO precursor or the nitrite source) is saturated in the solution. After cooling down the solution, the formulation may turn into a gel and the precipitated excess active agent can be easily removed. Variations in condition or sequence of mixing or addition of different ingredients/components are also feasible as long as the NO booster or NO precursor is suitably distributed in the formulation to achieve desirable therapeutic effects.

In some exemplary embodiments, the agent dissolved in the solution is filled into a container (e.g., a sprayer or nebulizer; a permeable or frangible pouch as described above) or soaked into a dispensing vehicle (e.g., swab, sponge or absorbing layer of a patch). When the NO precursor mixture contains a nitrite source, an acid source can be stored for example in a separate pouch or a separate layer of a patch. The NO precursor mixture and the acid source can also be separated by a removable barrier disposed between two different compartments of a container or between two layers of a patch.

In some embodiments, the formulation is in the form of a gel or semisolid. A gelling agent or thickener can be added to adjust the form of the formulation. The formulation is then filled into a suitable container and then dispensed as gels, ointments, creams, emulsions, microemulsions, nanoemulsions, pastes, balms, or other suitable forms. The semisolid formulation can also be coated on a backing member (e.g., a support layer of a patch).

Depending on the amount and nature of the thickener, the formulation can also be prepared into a solid form. For example, a solution of the NO booster (e.g. curcumin, desmethoxycurcumin, bisdesmethoxycurcumin, quercetin, berberine) can be mixed with melted pure cocoa butter and then cooled. The resulting solid formulation melts when rubbed with pressure on to human skin.

General procedures for mixing the reagents and handling the manufacturing process are available through the common knowledge or pharmaceutical technology handbooks well known to a person skilled in the art, for example, Remington: The Science and Practice of Pharmacy, 20th edition, Lippincott, Williams & Wilkins, Philadelphia, 2000, or in the review article Souza et al, Topical ocular delivery of therapeutics: carrier systems and physical methods, J. Pharm. Pharmacol., 2013, 66, 507-530.

Administration Regimen

The effective amount of the agent (NO booster or NO precursor) in the formulation or kit described herein for effectively enhancing systemic NO level will depend on the route of administration, the type of subject, including human, being treated, and the physical characteristics of the specific subject under consideration. The dose or amount can be tailored to achieve a desired effect, but will depend on such factors as weight, diet, concurrent medication and other factors which those skilled in the medical arts will recognize. More specifically, an effective amount or therapeutically effective amount means an amount of the agent effective to increase the systemic NO to a level to prevent, alleviate or ameliorate symptoms of disease or prolong the survival of the subject being treated. The administration of the formulation may be adjusted to provide the optimal therapeutic response or prolonged beneficial effects. For example, the formulation may be topically administered more than two or more than three times a day. Alternatively, the amount or administration frequency may be reduced if necessary. Determination of an effective amount is well within the capability of those skilled in the art, especially in light of the detailed disclosure provided herein.

In non-human animal studies, applications of potential products are commenced at higher dosage levels, with dosage being decreased until the desired effect is no longer achieved or adverse side effects disappear. The dosage may range broadly, depending upon the desired effects and the therapeutic indication. Typically, the effective amount of the agent or dosage in the formulation may be about 10 microgram/kg to about 100 mg/kg body weight, preferably about 100 microgram/kg to about 10 mg/kg body weight. Alternatively, dosages may be based and calculated upon the surface area of the patient, as understood by those of skill in the art.

In exemplary embodiments, the formulation is administered once a day, twice a day, three times a day, once in two days, once in three days, once in a week, one every two weeks or once a month.

The exact formulation, route of administration and dosage for the pharmaceutical compositions can be chosen by the individual physician in view of the patient's condition. (see e.g., Fingl et al. 1975, in "The Pharmacological Basis of Therapeutics", which is hereby incorporated herein by reference in its entirety, with particular reference to Ch. 1, p. 1).

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administered dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

The formulation disclosed herein can be evaluated for efficacy and toxicity using known methods. For example, the toxicology of the formulation may be established by determining in vitro toxicity towards a cell line, such as a mammalian, and preferably human, cell line. The results of such studies are often predictive of toxicity in animals, such as mammals, or more specifically, humans. Alternatively, the toxicity in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of the active agents of the transdermal f in humans.

The formulation or kit described herein may, if desired, be presented in a pack or dispenser device which may contain one or more unit dosage forms containing the formulated agent. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert.

All references cited herein are incorporated herein by reference in their entireties.

EXAMPLES

Example 1

Preparation of Transdermal Formulation

Vehicles for loading the active ingredient were prepared as illustrated in samples 1-4. Myristic acid (solid flakes) was dissolved in PEG400 upon warming the mixture in a warm water bath. Shaking accelerated the formation of the resulting clear solution. The following four concentrations of myristic acid (MA) in PEG400 were prepared and evaluated. Samples 1, 2, 3 and 4 were all clear solutions when the samples were allowed to attain ambient temperatures.
  a. 30 ml of PEG400+1.5 grams of MA (Sample 1)
  b. 30 ml of PEG400+3 grams of MA (Sample 2)
  c. 30 ml of PEG400+0.75 grams of MA (Sample 3)
  d. 30 ml of PEG400+2.25 grams of MA (Sample 4)

The samples as vehicles were loaded with NO enhancing agent. The sample carrier formulations [or solvent systems] were loaded with 95% pure curcumin (Curcumin 95) as the NO boosting agent to test loading potential. 1.5 grams of Curcumin 95 was added to Samples 1, 2, 3. The resulting Curcumin 95 loaded samples were warmed and shaken until what appeared to be the maximum amount of dissolving of the curcumin occurred, and then were allowed to cool back to ambient temperature. All three samples allowed for the dissolving of almost all of the added curcumin resulting in an intensely colored dark solution. Sample 3 provided the higher solubility and remained liquid for weeks. Samples 1 and 2 were initially liquid but formed a solid uniform gel over a period of several hours. Sample 3 was prepared by dissolving 0.75 grams of MA in 30 ml's of PEG400 and heating in a water bath (~60-80 C) for ~15 minutes. Sample 4 was prepared by dissolving 2.25 grams of MA in 30 mls of PEG400 and heating in a water bath (~60-80 C) for ~15 minutes. Both sample 3 and sample 4 were uniform solutions when the heating cycle was finished. Upon cooling sample 3 remained liquid whereas sample 4 formed a uniform gel.

Once loading potential was established, sample transdermal formulations containing curcugen as the NO enhancing agent were made. Curcugen is a product containing curcumin, desmethoxycurcumin (DMC) and bisdesmethoxycurcumin (BDMC). The three curcuminoids account for about 50% by weight in curcugen. Sample formulations V3.3 and V4.3 were made by adding curcugen to Sample 3 and sample 4 vehicles, respectively (3 grams of curcugen in 30 mls of either solvent). The resulting mixtures were heated and shaken for ~15 minutes, after which both appeared as dark maroon uniform solutions. Upon cooling V3.3 (3 grams curcugen per 30 ml Sample 3 vehicle) remained liquid; whereas V4.3 (3 grams curcugen per 30 ml Sample 4 vehicle) became a uniform gel having the same dark maroon color (same color as V3.3 when heated).

No loss of color was observed over a period of at least three months for samples stored at ambient temperature. In marked contrast, the same volume of water with the same amount of added curcumin showed almost no color in the liquid phase and a substantial amount of undissolved material.

V4.3 was loaded into a syringe when warm and hence in the liquid state. The liquid in the syringe gelled when cooled to ambient temperatures but could be squeezed out of the syringe as a gel that slowly melted on the skin. The applied gel was easily be covered and trapped in a water proof and leakproof transparent bandage (e.g. Mepitel transparent film dressing). The dressing prevented loss of the applied formulation and could remain in place for several days without loss of formulation. When the Mepitel dressing was removed after several days there was no adhered formulation on the dressing and all the formulation was in the skin as reflected in an absence of staining on tissue that was aggressively wiped over the colored skin that was below the dressing. The color was fully lost after 7-8 days.

The addition of water to the PEG400/MA based formulation can create a nonuniform emulsion that poses difficulties for topical use. The presence of water limits solubility of curcumin, curcugen, quercetin and berberine in PEG. As a comparison, the same amount of curcumin was mixed with the same volume of water (i.e. 3 g. curcumin in 30 ml water). The resulting mixture showed almost no color in the liquid phase and contained a substantial amount of undissolved material.

The use of higher concentration MA solutions with PEG as the base solvent allowed for easy preparation of concentrated saturated solutions with low solubility NO enhancing actives such as curcumin, curcugen, quercetin, berberine and related molecules by simply adding an excess of the active agent to the heated high MA PEG/MA solvent system (e.g. V4.3) and allowing the mixture to cool. The resulting uniform gel was fully saturated with the active agent, while the undissolved excess remained as a solid at the bottom of the tube. The uniform saturated gel was thereafter easily removed and separated from the undissolved material.

The Sample 3 solvent system was also tested as a vehicle for loading potential with the following low solubility reagents using the above method: quercetin, berberine, N-acetyl cysteine amide (NACA) and N-acetyl cysteine ethyl ester (NAC-ethylester). In all cases, the solvent system allowed for substantial dissolution of these hard to solubilize agents. A comparison between an aqueous solution and Sample 3 solution loaded with quercetin and berberine revealed minimal dissolved material in the aqueous sample and a high degree of solubilization in Sample 3.

Similar results were obtained for quercetin in sample 3 and sample 4 as vehicle but the solubility of the quercetin in these solvents was less than for curcugen (~200-300 mg quercetin in 30 ml of either sample 3 or sample 4). As with curcumin and curcugen, quercetin loaded sample 3 and sample 4 do not and do form a gel at ambient temperatures respectively.

The PEG400/MA solutions were combined with other delivery vehicles (e.g. petroleum jelly). Sample 3 with curcumin was mixed with petroleum jelly resulting in a uniformly colored gel that remained stable (no loss of color) over a period of over two months. Sample 3 with the dissolved SNO derivative of NAC amide and of NAC was easily combined with petroleum jelly to produce a stable pink jelly. Stability is likely derived from the low water activity and high viscosity which inhibit the loss of NO from the thiol group. Different sized aliquots of Sample 3 (both with curcumin and with curcugen) were mixed with melted pure cocoa butter and then cooled. Optimized mixtures yielded solid uniformly yellow/orange colored blocks/tubes of cocoa butter that remained solid at ambient temperature. The solid material melted when rubbed with pressure onto human skin. Similar results were obtained with coconut oil but the lower melting point of coconut oil made it difficult to apply to human skin without smearing and dripping. Combinations of the two oils were also tested. The use of PEG400/MA with cocoa butter showed most promising properties as a topical delivery vehicle suitable for cosmetic and dermatological applications due to the more suitable hardness for the resulting curcumin loaded cocoa butter. Increasing the amount of added PEG400/MA solvent to the cocoa butter eventually resulted in a gel like substance that remained stable color wise.

The solutions of the two lipophilic NAC derivatives were prepared using sodium nitrite saturated PEG400, resulting in a clear solution. The lipophilic derivatives of NAC readily dissolved under conditions where NAC had limited solubility. NAC is water soluble and the two derivatives are marginally soluble in water. The two solutions were then treated with several drops of acetic acid to trigger the formation of nitrous acid from the nitrite which can then nitrosate the reactive thiol on both of the NAC derivatives. The solutions turned pink indicative of S-nitrosothiol formation. The solutions remained pink for several days. The corresponding aqueous solutions lost color within hours. The use of nitrite saturated PEG400 allows for formulations that can be used to generate NO and S-nitrosothiols through mixing with reagents that acidify the mixture. A double frangible pouch incorporated into a patch may be used for a sustained NO delivery vehicle suitable for topical and transdermal applications.

Example 2

Effects on blood pressure (BP) on rats of V2.3 formulation (2 g curcugen per 30 ml Sample 3 vehicle) were examined. The formulation was topically applied to the shaved abdomen of 5 Sprague Dawley rats. A Q tip saturated with V2.3 was rubbed onto the shaved rat belly. In all instances (N=5) the application of V2.3 produced a 20% drop in systemic blood pressure within 15 to 20 minutes of application. The reduced blood pressure was maintained for the three hour observation window with no indication of recovery. Results (N=6) from a second laboratory in which 6 rats were similarly tested showed a similar result (20% drop in blood pressure) Similar results with V3.3 were consistently obtained on a single human subject upon application of V3.3 to the forearm (~0.05 ml). A comparable drop in BP occurred within 15 to 20 minutes of application and the lowered BP persisted for many hours, only gradually returning to the higher initial values after 12 to 24 hours. Similar results on the same human subject were obtained using V4.3. The cocoa butter doped with Sample 3 (V1.3) also exhibited similar physiological consequences when applied to the single human test subject. The control Sample 3 without one or more curcuminoids or curcugen elicited no physiological consequences when applied to either rat or human.

V3.3 was applied to a skin flap with an optical window on healthy hamsters. The optical window allowed for the monitoring of blood vessels in the dermal layer below the site of administration of the V3.3. A dose dependent increase in vessel diameter at the site of the topical application was observed within several minutes of application.

Effects on NO Plasma levels. Plasma levels of NO degradation products (nitrite/nitrate) were measured subsequent to topical application of V3.3 in 4 rats. Plasma levels of NO degradation products (nitrite/nitrate) in two of the tested rats were shown to increase by 15% consistent with the drop in blood pressure originating from enhanced production of nitric oxide due to the known ability of curcumin to upregulate endothelial nitric oxide synthase (eNOS) and hence NO production. Two control animals showed no such increase under the same conditions. The results indicate that transdermal curcuminoids can elevate systemic NO levels.

The drop in blood pressure within 15 to 20 minutes after topical application of a curcumin containing sample indicates that the curcumin is being delivered transdermally and that therapeutically effective levels are present within that short time period. The drop in blood pressure and increase in nitrite/nitrate plasma levels are consistent with the known effect of curcumin with respect to upregulation of nitric oxide production in the endothelium by eNOS. The physiological response is persistent over many hours consistent with topically delivered curcumin/curcugen is being delivered into the circulation in a sustained manner. In contrast, curcumin delivered into the circulation either via oral route or IV has a circulation time of only 2 hours due to the liver rapidly converting curcumin to an inactive agent. Even large dosing of oral curcumin has not been observed to produce this pronounced and prolonged physiological response.

Physiological response transdermal curcuminoid formulation in animals was also examined for V3.3 (Curcugen 9 g, myristic acid 2.25 g, PEG 400 90 ml) and V4.3 (Curcugen 9 g, myristic acid 6.75 g, PEG 400 90 ml).

Blood pressure was measure in rodents subsequent to topical application of transdermal curcuminoid formulation. Both rats and mice show up to a 20% reduction in BP with V3.3 being more effective than V4.3 both in terms of time of onset and extent of BP drop.

It was also observed that topical application of either V3.3 or V4.3 resulted in increased levels of plasma nitrite and nitrate of the three hour monitoring window subsequent to a single topical dose. Over the same time period the BP underwent a sustained decrease (over the three hour window). A sustained build up in the detectable concentration of plasma curcuminoids was observed over a three hour window subsequent to topical application of V3.3 in rats (N=3). Oral curcumin plasma levels peak in an hour and drop to near undetectable levels within three hours.

Example 3

Control on systemic inflammation via transdermal delivery of NO booster or NO precursor.

Inhibition on development of severe vascular leakage in an acute inflammation rat model was examined with topically applied formulation V3.3. The study used the following lipopolysaccharide (LPS) induced cytokine storm protocol:
 a. LPS (10 mg/kg) was IP infused every 24 hours to initiate and sustain an acute inflammatory response.
 b. The LPS treated rats were subjected to topical application (0.1 ml) of formulation V3.3 starting at the time of the first LPS treatment and repeated every 24 hours for three days
 c. Physiological parameters derived from drawn blood were measured every 24 hours
 d. After three days the animals were anesthetized and surgically opened to allow for the intravital fluorescence imaging of the macro and micro vasculature.
   i. Formulations of fluorescent labeled albumin and dextran (500 kDa) were IV infused and fluorescence derived images of the vasculature and surrounding tissue were used to determine the rate of extravasation out of the vasculature and into the surrounding tissues for both albumin and dextran.

Topical application of the vehicle (PEG400/MA) on the LPS treated rats revealed a pattern of rapid and extreme leakage for both albumin and the much larger dextran consistent with what was observed under conditions of severe acute inflammation. However, topical daily application of V3.3 dramatically reduced the amount of leakage for albumin. The observed low level of leakage is approximately the same as what was observed for a control animal. Similar results were observed for dextran. Extensive vascular leakage is a potentially lethal consequence of the cytokine storm independent of cause (COVID-19, Ebola, Dengue fever, hemorrhagic shock, endotoxic shock, Rift valley fever etc). The transdermal formulation provided a dramatic positive intervention outcome with far reaching clinical implications.

Example 4

This study evaluated potential therapeutic efficacy of a transdermally delivered transdermal formulation according to the invention (V4.3: curcugen 9 g, myristic acid 6.75 g, PEG 400 90 ml) in an acute vascular inflammation mouse model. Three cohorts each with three subjects were studied and compared. In Cohort 1, the subjects were infused with LPS but without no topical treatments (untreated). In Cohort 2, the subjects were infused with LPS topical treatment (0.1 ml of V4.3). In Cohort 3, LPS infusion was followed by topical treatment (0.1 ml of V4.3) four hours after LPS infusion. Endotoxemia was induced by infusion of 10 mg/kg of LPS (Lipopolysaccharides from $E.$ $coli$ serotype 0128: B12, Sigma Aldrich St. Louis, MO). The procedures were the same as those described in earlier published studies (Williams A T, Muller C R, Govender K, Navati M S, Friedman A J, Friedman J M, Cabrales P. Control of systemic inflammation through early nitric oxide supplementation with nitric oxide releasing nanoparticles. Free Radic Biol Med. 2020; 161:15-22. Epub 2020/10/05. doi: 10.1016/j.freeradbiomed.2020.09.025. PubMed PMID: 33011274; PMCID: PMC7529593 and references therein).

It was observed that topically applied V4.3 (curcuminoids dissolved in a PEG400/myristic acid mix) acted both as a prophylactic and interventional treatment for lipopolysaccharide (LPS) induced cytokine storm. The results include the vascular consequences and cytokine profile as a function of time for three different groups of LPS treated mice: i) no topical treatment with V4.3; ii) pretreatment with topical V4.3 prior to the LPS treatment and iii) topical treatment with V4.3 after the onset of the LPS initiated cytokine storm. In terms of the response of the microvasculature to LPS treatment in the three groups, treatment with topical V4.3 both limited arterial dilation, which is indicative of shock induced vascular collapse, and maintained arterial blood flow. It was also observed that topical V4.3 prevented the steep drop in functional capillary density (FCD) that occurs with LPS induced endotoxemia. V4.3 was effective both as a prophylactic and as an interventional treatment in preventive steep decline in FCD relative to baseline (BL). FCD correlates with survival in that it reflects the ability to maintain tissue perfusion and deliver oxygen to tissues. Further, it was discovered that both pre-treatment and interventional treatment with topically applied V4.3 limited the production of pro-inflammatory cytokines. These results confirmed the efficacy of the transdermal formulation in limiting the inflammatory consequences when administered topically as a prophylactic or as an active therapeutic subsequent to onset of the inflammation.

Example 5

This study evaluated prevention of LPS induced vascular leakage via topically administered curcuminoids using a transdermal formulation according to the present invention in an LPS endotoxemia rat model. LPS ($E$ $coli$ O26:B6) was inoculated to rat model (10 mg/kg/day). A transdermal curcumin formulation (V3.3: curcugen 9 g, myristic acid 2.25 g, PEG 400 90 ml) or vehicle control was applied daily for three days (0.1 ml/dose). On day 3, the animals were surgically prepared for intravital and fluorescence microscopy. It was observed that treatment with the transdermal curcumin formulation prevented the LPS induced early phase leakage (first 4 hours). Vascular leakage is dramatically reduced subsequent to topical application of V3.3 in an LPS induced inflammation mode. Meanwhile, topical application of V4.3 (curcugen 9 g, myristic Acid 6.75 g, PEG 400 90 ml) both prior to and subsequent to LPS induced inflammation in mice (N=3) reduced the LPS induced increase in pro-inflammatory cytokine levels.

This experiment, combined with results from the earlier studies, indicates that topical transdermal curcumin formulation of this patent document can limit inflammation induced vascular leakage which is a characteristic of the cytokine storm and other inflammation inducing conditions.

Example 6

Skin permeation of transdermal formulations of the present invention was studied. Skin permeation of the following transdermal formulations according to the present invention were studied using confocal microscopy. The formulations differed only in the amount of myristic acid:
 a. Lot 43: V4.3 Curcugen 9 g, Myristic Acid 6.75 g, PEG 400 90 ml
 b. Lot 39: V3.3 Curcugen 9 g, Myristic Acid 2.25 g, PEG 400 90 ml
 c. Lot 38: V0.3 Curcugen 9 g, PEG 400 90 ml The formulations solidified as temperatures approached zero centigrade. The viscosity was visibly reduced in all samples as the temperature was raised above ambient. Viscosity of the formulations and their ingredients are as follows:
 Water 0.9 cP; PEG400 (100%) 99 cP; PEG400/water 90%, 80 cP; V3.3: 149.8 cP; PEG400+myristic acid, V3.3: 149.8 cP; PEG400+myristic acid, V4.3: 4220 cP.

Curcuminoids have a broad absorbance spectrum with a maximum absorbance at 425 nm. All human skin sample integrity was measured using TEWL data and all samples used had good integrity of the skin barrier. A DAPI filter was used to visualize the curcuminoid penetration. All images were taken at the same settings.

All three formulations showed penetration of the curcuminoids into the skin. At the earliest time point of one hour penetration of the curcuminoids into the stratum corneum with all three formulations was observed.

In the formulation of lot 38, in both donors, broadening of fluorescent band occurred from 3 to 6 hours. Broadening of band was not seen in the formulation of lot 39 and 43 until the 24th hour. The broadening suggests the permeation of the curcuminoids into the upper epidermal layers just below the stratum corneum. In the formulation of lot 39, in both donors, the amount of curcuminoids between 3 to 6 hours decreased in both donors. However, a decrease in the intensity for curcuminoids in the formulation of lot 38 and 43 was observed after 6 hours. In the formulation of lot 38, fluorescent spots were seen below the stratum corneum at the early time points. However, no fluorescent spots were seen above the stratum corneum with the formulation of lot 39 and 43. Transepidermal water loss (TEWL) values are comparable for all formulations and all time points suggesting that all human skin sample barrier integrity was the same.

The decrease in fluorescence over time in the three formulations is an indication of penetration of the curcuminoids into deeper layers of the skin. (Low amounts of penetration of the actives may have not be visualized and/or quantified due to the high autofluorescence of the untreated skin). Based on this, the formulation of lot 39 shows earliest penetration of the curcuminoids into the skin. The depth of fluorescence was also determined. This was measured at values between 5 microns to 25 microns. The formulation of lot 38 showed the fastest broadening of the fluorescent band suggesting faster skin penetration of the curcuminoids.

Example 7

The effect of the transdermal formulation of this patent on limiting or preventing the onset of cardiovascular inducing inflammation in a diabetic rat model was examined in ZDSD diabetic rat model. The 3 rats were on a normal diet for 60 days without symptoms of diabetes. Starting on ~day 65 the rats were started on a high fat diet that resulted in a slow increase in blood glucose. The animals were treated topically with formulation V4.3 every two days for the entire test period out to 80 days. Cytokine profile showed the onset of inflammation at ~day 75. The treatment with formulation V4.3 limited the increase in pro-inflammatory cytokines seen in the shams at day 75. In particular, the profile for IL-18 showed clear evidence of the formulation in preventing the increase in IL-18 which is a marker for propensity of developing cardiovascular consequences in diabetics.

Example 8

The effect of treatment of mice with severe advanced endothelial dysfunction was examined with Formulation V4.3. A total of 24 male C57BL/6J mice aged 6-8 weeks were used in the study. Mice were housed in an animal facility under a 12/12-h day/night cycle and access to food and water ad libitum. The study was carried out over a period of 4 weeks. Week 1 was used for adaptation as the animals were divided into experimental groups. Two groups received L-NAME (50 mg/kg) in their drinking water for two weeks (week 2 and 3) to chronically induce nitric oxide synthase (NOS) inhibition. One L-NAME treated group received topical formulation V4.3 at a dosing of 0.1 ml daily for the last 10 days before characterization. The L-NAME untreated group was used as Sham group.

Topical treatment was initiated after the onset of the condition. The results showed direct evidence of the treatment, which restores elements of normal endothelial function (decreased oxidative stress in plasma and RBCs, decreased leukocyte adhesion to the endothelium indicative of recovery of the glycocalyx, and improved functional capillary density). In comparison with the Sham group, the group treated with the transdermal formulation exhibited a lower level of TNF-α, TGFβ, MCP-1, IL-1α, IL-1β, IL-6, IL-10, and IL-10. Better results from the treated group were also observed in terms of microhemodynamic changes, cell adhesion, vascular response of isolated aortic vessels, changes in erythrocyte and plasma antioxidants, hypoxia, reoxygenation, and systemic hemodynamic changes.

TABLE 1

Changes in body weight, relative tissue weights and water intake at the end of the study.

|  | BW, g | Kidney relative to BW | Heart relative to BW | Daily Water intake, mL |
|---|---|---|---|---|
| Control | 25 ± 4 | 1.44 ± 0.07 | 1.16 ± 0.08 | 4.3 ± 0.6 |
| Curcumin | 24 ± 3 | 1.32 ± 0.08 | 1.08 ± 0.07 | 4.7 ± 0.8 |
| Sham | 26 ± 4 | 0.82 ± 0.04 | 0.87 ± 0.06 | 3.9 ± 0.4 |

TABLE 2

Changes in Erythrocyte and plasma antioxidants at the end of the study

|  | Erythrocyte SOD, unit/$g_{Hb}$ | Erythrocyte Catalase, unit/$g_{Hb}$ | Erythrocyte GSH, μmole/$g_{Hb}$ | Plasma GSH, μM |
|---|---|---|---|---|
| Control | 3.4 ± 0.2 | 23.1 ± 3.0 | 4.2 ± 0.6 | 2.1 ± 0.4 |
| Curcumin | 4.0 ± 0.4 | 28.3 ± 2.7 | 5.1 ± 0.6 | 2.7 ± 0.6 |
| Sham | 5.1 ± 0.5 | 36.9 ± 2.4 | 6.0 ± 0.7 | 3.4 ± 0.5 |

Example 9

This experiment shows that pretreatment with oral curcumin over several days prior to hemorrhage dramatically reduced the inflammatory and oxidative elements of HS. It is shown that transdermal delivery of curcumin (in the form of Formulation 4.3 restored vascular homeostasis in a septic shock guinea pig model. Additionally, transfusion studies indicate that red blood cells can act as a stealth pharmacological vehicle for transport and delivery of curcumin. Overall, these and multiple other published studies suggest that curcumin can mitigate the consequences of HS.

The experiment tested the hypothesis that packed RBCs loaded with curcumin can be used to enhance therapeutic efficacy in a guinea pig HS model. The capacity for resuscitation after the onset of HS was compared between fresh RBCs, aged RBCs and aged RBCs pretreated with Formulation 4.3 just prior to infusion. Formulation 4.3 restored i) functional capillary density (FCD), the parameter of microvascular functionality that most closely correlates with survival, ii) blood flow and iii) other measures of cardiovascular function. The R120 FCD results show that Formulation 4.3 treated RBCs had the best performance for most measures of vascular health, even exceeding that of fresh RBCs.

Example 10

The following procedure was used to evaluate the effect of the Formulation 4.3 formulation:
- Single dose treatment of RBCs (fresh packed) suspended in PBS-Glucose with Formulation 4.3 on day 1 of a 14 day storage period (resulting in 1 mM curcuminoids in the bag of stored RBCs)
- 24 hour survival of treated and untreated stored RBCs (7 and 14 days) with and without single dose treatment with Formulation 4.3 on day 1. Small aliquots of sample removed at days 1, 7 and 14 for analysis of markers of storage lesion.
- Multiple (3) dosing of stored RBCs (29 day storage period) starting with the first dose on day 28
- Evaluation of stability of circulating unstable RBCs (in a humanized sickle cell mouse model following topical application of Formulation 4.3

It was observed that a single dose of the formulation added at the onset of storage limits loss of ATP levels and oxidative damage.

ATP Levels Relative to Day 1
  Day 1: 100%
  Day 14: control 28%, Formulation 4.3 treated 45%
Oxidative Damage (Fold Increase Relative to Day One Values
  Intracellular ROS
    Day 14: 9 fold increase for control v. 5 fold increase for formulation treated samples
  Protein carbonyl content
    Day 14
      5 fold increase for control v. 3 fold increase for formulation treated samples
  Lipid hydroperoxide content
    Day 14
      7 fold increase for control v. 5 fold increase for formulation treated samples
  Ferryl hemoglobin formation at day 14 (Ferryl Hb is highly reactive triggering oxidative stress, ROS and peroxynitrite production) Ferryl Hb content is reflected in SulfHb concentration μM).

Vehicle control 4.9 v. Treated with formulation 3.8

Example 11

This experiment showed that transfused RBCs after storage with the addition of Formulation 4.3 at day 1 show enhanced circulation times compared to vehicle control following 14 and 21 days of storage.

Blood storage and treatment. Guinea pigs weighing between 350 and 400 g were used. Guinea pigs were fed regular chow (ND; Envigo TD.2040). Guinea pigs anesthetized and a femoral artery catheter was implanted. Animals bled freely into CP2D, AS-3 was added to the manufacturer's recommended concentration, and RBCs were passed through a neonatal leukocyte reduction filter. The RBCs units were stored for three weeks. Formulation 4.3 RBC were stored with the formulation at 1 mM.

Post transfusion 24 hour recovery. RBCs from each group was radiolabeled with Technetium-99 (Tc99) after 2 and 3 weeks of storage. 200 μL of Tc99 radiolabeled blood (approximately 2% of BV) was delivered via femoral vein catheter to anesthetized Guinea pigs and samples were drawn at 5 and 30 mins and 24-h postinjection via femoral artery catheter. Samples were all run for radioactivity on a Cobra II gamma counter. The following results regarding percent of 24 hour post transfusion recovery of transfused RBCs were observed: Fresh RBC's 88%; Two weeks 75% v. Two weeks treated with formulation 80%; Three weeks 67% v. Three weeks treated with Formulation 4.3 75%.

Therefore, addition of the formulation at the onset of the storage process enhances the circulation time of the aged transfused RBCs. In addition, circulation time is a reflection of the general status of the RBCs. These results are consistent with the direct stability studies showing that addition of the formulation limits the development of storage lesion in aged RBCs.

Example 12

This experiment examined the effect of Formulation 4.3 on human red blood cells (RBCs) starting after 28 days of storage. Significant enhancement of RBC profile and extension of refrigerated shelf life was observed at the end.

Human RBCs were collected and stored with standard additives (AS-3: alpha.-d-glucopyranose, trisodium citrate, sodium chloride, phosphoric acid, monosodium salt, citric acid, adenine). The experiment included the following steps:
1. 50 ml total whole blood was used for each set of experiments.
2. RBCs were separated from Leukodepleted blood after removing the buffy coat and plasma.
3. Packed RBCs were stored in standard RBC storage bags after mixing with AS-3 solution (11 ml).
4. On storage day 28, RBCs in AS-3 solution were divided in 3 equal parts and kept in separate storage bags (15 ml, 50 μM, in each bag).
5. Further additions repeated on Storage Day 35 and 42, respectively.
6. Samples were collected and analyzed following storage at 28, 35, 42 and 49 days, respectively.

On storage day 28, sample was divided into 3 separate storage bags (50 ml per bag), as follows:
  a. control—no other additives
  b. formulation 4.3—8 microliters formulation 4.3 added resulting in 50 micromolar curcuminoids in bag.
  c. vehicle—8 microliters of solvent system added resulting in 0 micromolar curcuminoids in bag.

|  | 35 Days | | | | 42 Days | | | | 49 Days | | | |
| --- | --- | --- | --- | --- | --- | --- | --- | --- | --- | --- | --- | --- |
|  | Hemolysis % | Met % | p50 | n | Hemolysis % | Met % | p50 | n | Hemolysis % | Met % | p50 | n |
| Control (AS3) | 1.42 | 0.78 | 18.16 | 2.13 | 1.62 | 0.87 | 18.28 | 2.32 | 1.75 | 0.06 | 18.16 | 2.3 |
| Cur (AS3 + Formulation 4.3) | 1.72 | 1.35 | 18.33 | 2.11 | 2.12 | 2.95 | 18.66 | 2.37 | 3 | 3.65 | 18.42 | 2.35 |
| Veh (AS3 + Vehicle) | 1.3 | 0.01 | 18.88 | 2.27 | 1.77 | 2.11 | 18.90 | 2.31 | 2.49 | 1.75 | 18.88 | 2.28 |

Results: Formulation 4.3 treated RBCs exhibited extended shelf life as reflected in statistically significant improvements in markers of storage lesions. Enhancement in ATP levels, reduction in Band 3 phosphorylation and reduction in oxidative damage were observed. The formulation showed compelling efficacy as a shelf-life extender for stored human RBCs which is one of the most commonly utilized transfusion materials.

Enhanced ATP Levels Compared to Control (Percent of Starting Control Value)
- Day 35: control 60, vehicle 50, Formulation 4.3 80
- Day 42: control 38, vehicle 40, Formulation 4.3 55
- Day 49: control 32, vehicle, 30, Formulation 4.3 45

Reduction in Band 3 Phosphorylation (Percent Increase Over Control at Starting Time)
- Day 35: control 3.5, vehicle 3.3, Formulation 4.3 2.0
- Day 42: control 4.8, vehicle 5.0, Formulation 4.3 3.0
- Day 49: control 5.8, vehicle 6.3, Formulation 4.3 5.5

Limiting Protein Oxidative Damage (Carbonyl Formation) in Nmoles Per ml of Rbc.
- Day 35: control 40, vehicle 40, Formulation 4.3 22.
- Day 42: control 60, vehicle 65, Formulation 4.3 45.
- Day 49: control 75, vehicle 75, Formulation 4.3 58

Example 13

Topically applied Formulation 4.3 can stabilize circulating red blood cells: Three week alternate day topical treatment with Formulation 4.3 (4 mg per dose) enhances RBC stability in a humanized sickle cell mouse model (highly unstable RBCs) compared to control (vehicle).

Briefly, topical application of either Formulation 4.3 or vehicle every other day for 21 days. RBCs isolated on day 21 and analyzed for ATP content and protein oxidation. Blood removed at day 21 and evaluated for marker of hemolysis (LDH, lactate dehydrogenase). PK data and the following were then obtained:
- ATP content (nmoles/ml rbc): Vehicle 30, Formulation 4.3 50
- Protein oxidation (carbonylation) nmoles/ml rbc: Vehicle 25, Formulation 4.3 25
- LDH levels (units/ml): Vehicle 2.2, Formulation 4.3 0.5
- Multiple PK studies on both rats and mice show that topical application of Formulation 4.3 results in the sustained appearance of curcumin in both plasma and blood cells Topical application of Formulation 4.3 therefore resulted in transdermal systemic stabilization of circulating RBCs with: i) evidence of improved redox status and enhanced ATP content of RBCs obtained from treated animals; and ii) in vivo evidence of transdermal enhancement of RBC stability as reflected in a decreased level of a key marker of hemolysis over the 21 day test period compared to vehicle alone control.

Example 14

This experiment used a hemorrhagic shock model (hamster) in which the therapeutic efficacy of transfused stored RBCs treated with a single dose of Formulation 4.3 at the start of the storage process (same protocol as in human RBC study) was compared to the outcome with either fresh RBCs or stored RBCs that were not treated. The treated stored RBCs out performed both the fresh and untreated stored with respect to maintaining functional capillary density which is the major determinant of tissue perfusion and clinical outcome.

In this preliminary study, the impact of transfusing aged red blood cells (RBCs) stored with Formulation 4.3 was assessed on systemic and microvascular parameters during resuscitation from severe hemorrhagic shock, comparing the outcomes with conventionally stored RBC. The experiments were conducted in unanesthetized hamsters equipped with a skinfold window chamber, allowing for real-time visualization of microvascular responses. The experimental protocol involved inducing hemorrhage equivalent to 50% of the hamsters' total blood volume, followed by 1 hour of hypovolemic shock. Subsequently, fluid resuscitation was administered, corresponding to 50% of the shed blood volume. The choice of this animal model and experimental design aimed to closely simulate the conditions of severe hemorrhagic shock and its clinical management.

The results revealed that resuscitation with aged RBCs treated with Formulation 4.3 is not inferior to using fresh RBCs and demonstrates superiority compared to conventionally stored aged RBCs. The assessment of systemic parameters, including blood pressure, indicated a favorable response to Formulation 4.3-treated RBCs, highlighting their effectiveness in restoring hemodynamic stability during the critical resuscitation phase. Moreover, the investigation into microvascular parameters, including microhemodynamics and functional capillary density, provided insights into the tissue-level responses to transfusion. Functional capillary density, a vital indicator of the balance between enhanced oxygen transport and tissue perfusion, showed notable improvements with Formulation 4.3-stored RBCs.

It will be appreciated by persons skilled in the art that the inventions described herein are not limited to what has been particularly shown and described. Rather, the scope of the invention is defined by the claims which follow. It should further be understood that the above description is only representative of illustrative examples of embodiments. The description has not attempted to exhaustively enumerate all possible variations. The alternate embodiments may not have been presented for a specific component of a composition, or a step of the method, and may result from a different combination of described constituents, or that other undescribed PEG alternate embodiments may be available for a formulation, kit or method, is not to be considered a disclaimer of those alternate embodiments. It will be appreciated that many of those undescribed embodiments are within the literal scope of the following claims, and others are equivalent.

The invention claimed is:

1. A method for preparing a blood sample with delayed onset or retarded progression of storage lesion of red blood cells ex vivo in the sample during storage, comprising mixing the sample with a solution comprising an effective amount of a curcuminoid, wherein concentration of the curcuminoid in the sample ranges from about 0.1 to about 1 mM.

2. The method of claim 1, wherein the effective amount is selected such that the red blood cells remain substantially viable for the period of at least about 60 days.

3. The method of claim 1, wherein the effective amount is selected such that inflammation, hemolysis or microparticle formation is reduced by at least 20% in comparison with an untreated reference over the same period of time.

4. The method of claim 1, wherein the solution further comprises myristic acid.

5. The method of claim 1, wherein adenosine triphosphate (ATP) and/or 2,3-diphosphoglycerate (2,3-DPG) levels in the sample decreases by less than 20% in a period of 50 days.

6. The method of claim 1, wherein the solution comprises a solvent selected from the group consisting of polyethylene glycol, ethanol, acetone, ethyl acetate, acetonitrile, DMF, THF, DMSO, isopropanol, 1-butanol, xylenes, n-hexane, n-heptane and any combination thereof.

7. The method of claim 1, wherein the solvent comprises polyethylene glycol (PEG).

8. The method of claim 1, wherein the solvent consists essentially of PEG.

9. The method of claim 8, wherein the solvent and the curcuminoid are in a ratio ranging from about 5:1 to about 20:1 by weight.

10. The method of claim 8, wherein the PEG has a molecular weight ranging from 200 to about 600.

11. The method of claim 8, wherein the PEG and the curcuminoid are in a ratio ranging from about 8:1 to about 30:1.

12. The method of claim 1, wherein the sample and the solution are in a ratio ranging from about 8000:1 to about 3000:1 by weight.

13. The method of claim 1, wherein the curcuminoid is curcumin.

14. The method of claim 1, wherein the curcuminoid ranges from about 3% to about 15% by weight in the solution.

15. The method of claim 1, wherein the solution is substantially free from water.

16. The method of claim 1, wherein the solution further comprises at least a flavonoid.

17. The method of claim 16, wherein the flavonoid is selected from quercetin, apigenin, fisetin, luteolin, and rapamycin.

18. An ex vivo blood sample prepared according to the method of claim 1.

19. A method of transfusing blood to a subject in need thereof, comprising transfusing the blood sample of claim 18 to the subject.

20. A method for preparing a blood sample with delayed onset or retarded progression of storage lesion of red blood cells ex vivo in the sample during storage, comprising mixing the sample with a solution comprising an effective amount of a curcuminoid, wherein the effective amount is selected such that the red blood cells remain substantially viable for the period of at least about 60 days.

* * * * *